United States Patent
Satoh et al.

(10) Patent No.: US 10,416,563 B2
(45) Date of Patent: Sep. 17, 2019

(54) RESIST UNDERLAYER FILM COMPOSITION, PATTERNING PROCESS, AND METHOD FOR FORMING RESIST UNDERLAYER FILM

(71) Applicant: SHIN-ETSU CHEMICAL CO., LTD., Tokyo (JP)

(72) Inventors: Hironori Satoh, Joetsu (JP); Hiroko Nagai, Joetsu (JP); Takeru Watanabe, Joetsu (JP); Daisuke Kori, Joetsu (JP); Tsutomu Ogihara, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/915,737

(22) Filed: Mar. 8, 2018

(65) Prior Publication Data

US 2018/0284614 A1   Oct. 4, 2018

(30) Foreign Application Priority Data

Mar. 31, 2017   (JP) .................................. 2017-71098

(51) Int. Cl.
*G03F 7/11*     (2006.01)
*G03F 7/09*     (2006.01)
(Continued)

(52) U.S. Cl.
CPC ................ *G03F 7/11* (2013.01); *C07C 39/14* (2013.01); *C07C 39/17* (2013.01); *C07C 69/94* (2013.01);
(Continued)

(58) Field of Classification Search
CPC ......... C07C 39/14; C07C 39/17; C07C 69/94; C07D 251/32; C07D 487/04;
(Continued)

(56) References Cited

U.S. PATENT DOCUMENTS 5,576,359 A    11/1996 Urano et al.
5,756,255 A *  5/1998 Sato ........................ G03F 7/091
                                                      430/158
(Continued)

FOREIGN PATENT DOCUMENTS

EP    0 636 941 A1   2/1995
JP    S61-180241 A   8/1986
(Continued)

OTHER PUBLICATIONS

Aug. 6, 2018 Extended Search Report issued in European Patent Application No. 18164824.7.
(Continued)

*Primary Examiner* — Zandra V Smith
*Assistant Examiner* — Andre C Stevenson
(74) *Attorney, Agent, or Firm* — Oliff PLC

(57) ABSTRACT

A resist underlayer film composition is excellent in resistance to a basic hydrogen peroxide aqueous solution in gap-filling and planarization characteristics having a dry etching characteristic; a patterning process and method for forming a resist underlayer film, wherein the resist underlayer film composition is used for a multilayer resist method, the composition comprising: (a1) one, or two or more, of a compound represented by following general formula (x); and (b) an organic solvent, (Continued)

wherein $n^{01}$ represents an integer of 1 to 10; when $n^{01}$ is 2, w represents a sulfinyl group, a sulfonyl group, an ether group, or a divalent organic group having 2 to 50 carbon atoms; when $n^{01}$ is an integer other than 2, w represents an $n^{01}$-valent organic group having 2 to 50 carbon atoms; and y represents a single bond or divalent connecting group having 1 to 10 carbon atoms and optionally having an oxygen atom.

21 Claims, 2 Drawing Sheets

(51) Int. Cl.

| | | |
|---|---|---|
| C07C 39/14 | (2006.01) | |
| C07C 39/17 | (2006.01) | |
| C07C 69/94 | (2006.01) | |
| C07D 251/32 | (2006.01) | |
| C07D 487/04 | (2006.01) | |
| C08F 220/28 | (2006.01) | |
| C08F 220/32 | (2006.01) | |
| G03F 7/16 | (2006.01) | |
| G03F 7/20 | (2006.01) | |
| G03F 7/32 | (2006.01) | |
| G03F 7/38 | (2006.01) | |
| H01L 21/266 | (2006.01) | |
| H01L 21/308 | (2006.01) | |
| H01L 21/311 | (2006.01) | |

(52) U.S. Cl.
CPC ......... *C07D 251/32* (2013.01); *C07D 487/04* (2013.01); *C08F 220/28* (2013.01); *C08F 220/32* (2013.01); *G03F 7/091* (2013.01); *G03F 7/094* (2013.01); *G03F 7/16* (2013.01); *G03F 7/168* (2013.01); *G03F 7/2041* (2013.01); *G03F 7/322* (2013.01); *G03F 7/38* (2013.01); *H01L 21/266* (2013.01); *H01L 21/3081* (2013.01); *H01L 21/3086* (2013.01); *H01L 21/31133* (2013.01); *H01L 21/31138* (2013.01); *H01L 21/31144* (2013.01); *C07C 2603/18* (2017.05); *C08F 2220/281* (2013.01); *C08F 2800/20* (2013.01)

(58) Field of Classification Search
CPC .. C08F 220/28; C08F 220/32; H01L 21/3081; H01L 21/3086; H01L 21/31133; H01L 21/31138
See application file for complete search history.

(56) References Cited

U.S. PATENT DOCUMENTS

| | | |
|---|---|---|
| 5,919,599 A | 7/1999 | Meador et al. |
| 7,094,708 B2 | 8/2006 | Kato et al. |
| 9,372,404 B2 | 6/2016 | Watanabe et al. |
| 10,039,858 B2* | 8/2018 | Sant ................. A61L 27/3804 |
| 2002/0106909 A1 | 8/2002 | Kato et al. |
| 2010/0099044 A1 | 4/2010 | Hatakeyama et al. |
| 2010/0221657 A1 | 9/2010 | Sakamoto et al. |
| 2012/0181251 A1 | 7/2012 | Minegishi et al. |
| 2016/0218013 A1 | 7/2016 | Ohashi et al. |
| 2016/0284559 A1 | 9/2016 | Kikuchi et al. |
| 2017/0017156 A1 | 1/2017 | Ogihara et al. |
| 2017/0153548 A1 | 6/2017 | Nishimaki et al. |
| 2017/0371242 A1* | 12/2017 | Wakayama ............... G03F 7/11 |

FOREIGN PATENT DOCUMENTS

| | | |
|---|---|---|
| JP | 3082473 B2 | 8/2000 |
| JP | 2002-334869 A | 11/2002 |
| JP | 2004-205685 A | 7/2004 |
| JP | 2005-128509 A | 5/2005 |
| JP | 2005-250434 A | 9/2005 |
| JP | 2006-227391 A | 8/2006 |
| JP | 2006-285095 A | 10/2006 |
| JP | 2006-293298 A | 10/2006 |
| JP | 2007-199653 A | 8/2007 |
| JP | 2008-158002 A | 7/2008 |
| JP | 4310721 B2 | 8/2009 |
| JP | 2009-269953 A | 11/2009 |
| JP | 2010-122656 A | 6/2010 |
| JP | 2013-253227 A | 12/2013 |
| JP | 2016-185999 A | 10/2016 |
| KR | 20170017888 A | 2/2017 |
| TW | 201634615 A | 10/2016 |
| TW | 201710795 A | 3/2017 |
| WO | 2004/066377 A1 | 8/2004 |
| WO | 2012/176767 A1 | 12/2012 |
| WO | 2015/030060 A1 | 3/2015 |

OTHER PUBLICATIONS

Dec. 20, 2018 Office Action issued in Taiwanese Application No. 107110584.

* cited by examiner (G)

(H)

(I)

(J)

(K)

RESIST UNDERLAYER FILM COMPOSITION, PATTERNING PROCESS, AND METHOD FOR FORMING RESIST UNDERLAYER FILM

TECHNICAL FIELD

The present invention relates to: a resist underlayer film composition to be used for fine patterning by a multilayer resist method in a semiconductor device manufacturing process; a patterning process using the resist underlayer film composition, and a method for forming a resist underlayer film.

BACKGROUND ART

As LSI advances to a higher integration and a further facilitation in speed, miniaturization of a pattern size is rapidly progressing. In accordance with this miniaturization movement, the lithography technology has achieved formation of a fine pattern by shifting the wavelength of a light source shorter and by proper selection of a resist composition responding to such shift in the light source. The main factor of this is a positive photoresist composition used in a monolayer. In this monolayer positive photoresist composition, a skeleton having an etching resistance to dry etching by a gas plasma of chlorine-based or fluorine-based is incorporated into a resist resin and a switching mechanism to dissolve an exposed part is constructed in a resist resin, and thereby a pattern is formed by dissolving the exposed part, and then, a substrate to be processed is dry-etched by using the remained resist pattern as an etching mask.

However, if miniaturization is pursued without changing a film thickness of the photoresist film to be used, namely, if the pattern width thereof is made further narrower, resolution of the photoresist film decreases; in addition, if the photoresist film is pattern-developed by using a developer, a so-called aspect ratio thereof becomes so large that a problem of the pattern fall occurs. In view of the above-mentioned, the thickness of the photoresist film has been made thinner in accordance with this miniaturization movement.

On the other hand, for processing of a substrate to be processed, the method wherein this substrate is dry-etched by using a photoresist film having a formed pattern as an etching mask has been usually used. However, practically there is no dry etching method having a complete etching selectivity between the photoresist film and the substrate to be processed. Because of this, during processing of the substrate, the resist film is also damaged to cause collapse of the resist film so that there has been a problem that the resist pattern cannot be precisely transcribed to the substrate to be processed. Because of this, the resist composition has been required to have a further higher dry etching resistance in accordance with the movement to a finer pattern. On the other hand, however, in order to increase a resolution, the resin used for the photoresist composition has been required to have a smaller light absorbance at the wavelength of the exposure light. Therefore, as the exposure light shifts to a shorter wavelength, i.e., shifting to i-beam, KrF, and ArF, the resin has also been shifting to a novolak resin, polyhydroxystyrene, and a resin having an aliphatic polycyclic skeleton. Realistically however, the etching rate under the dry etching condition during the substrate processing has been increased so that recent photoresist compositions having a high resolution tend to have rather a lower etching resistance.

In the situation as mentioned above, a substrate to be processed must be processed by dry etching by using a photoresist film having a thinner thickness and a lower etching resistance than ever; and thus, securement of a material and a process in this patterning process has become an acute imperative.

One means to solve the problems mentioned above is a multilayer resist method. In this method, an intermediate film having the etching selectivity different from that of a photoresist film (namely, a resist upper layer film) is put between the resist upper layer film and a substrate to be processed; and after a pattern is formed on the resist upper layer film, this pattern is transcribed to the intermediate film by dry etching using the pattern on the upper layer film as a dry etching mask, and then, the pattern is transcribed further to the substrate to be processed by dry etching using the intermediate film as a dry etching mask.

One of the multilayer resist methods is a three-layer resist method in which a general resist composition used in a monolayer resist method can be used. In this three-layer resist method, for example, an organic film formed of a novolak resin or the like is formed on the substrate to be processed as the resist underlayer film, on it a silicon-containing film is formed as the resist intermediate film, and further on it a usual organic photoresist film is formed as the resist upper layer film. Because the organic resist upper layer film can have a good selectivity relative to the silicon-containing resist intermediate film in dry etching by a fluorine-based gas plasma, the resist upper layer film pattern can be transcribed to the silicon-containing resist intermediate film by using dry etching by the fluorine-based gas plasma. According to this method, even if a resist composition with which a pattern having a sufficient film thickness to directly work on the substrate to be processed is difficult to be formed is used, or a resist composition whose dry etching resistance is insufficient to work on the substrate is used, the pattern can be transcribed to the silicon-containing film (the resist intermediate film), and then, by transcribing the pattern by the dry etching using an oxygen-based or a hydrogen-based gas plasma, the pattern of the organic film (resist underlayer film) formed of a novolak resin or the like having a sufficient dry etching resistance to the substrate processing can be obtained. Many of the resist underlayer films as mentioned above have already been in the public domain, such as, for example, those described in Patent Document 1.

On the other hand, in recent years, production of the semiconductor device having a novel structure such as a multi-gate structure is being actively investigated; and with this movement, requirements for better planarization and gap-filling characteristics than before are increasing more than before in the resist underlayer film. For example, when there is a very fine pattern structure such as a hole, a trench, or a fin in the underlayment substrate to be processed, the gap-filling characteristic to fill up inside the pattern by the resist underlayer film without a void becomes necessary. Further, when there are steps on the underlayment substrate to be processed, or when a dense pattern area and a scarce pattern area co-exist on the same wafer, the film surface needs to be planarized by the resist underlayer film. By planarizing the underlayer film surface, variance of the film thickness of the resist intermediate film and the resist upper layer film to be formed thereupon can be suppressed; and as a result, the decrease in a focus margin of the lithography as well as in a margin in the subsequent process step of the substrate to be processed can be suppressed. Alternatively, in order to remove, by dry etching, the resist underlayer film used for gap-filling and planarization without leaving the residue thereof after the substrate processing, the resist underlayer film having the dry etching characteristics different from those of the above-mentioned, for example, the resist underlayer film having the dry etching rate faster than that of the resist upper layer film, is sometimes required. Further, there is also a case that the substrate processing by wet etching using a chemical is required, wherein the resist underlayer film acting as the processing mask is required to have a resistance to a wet etching solution.

Meanwhile, the background for requirement of the material matching to the wet etching process in the multilayer resist method will be explained in detail. In order to improve the semiconductor device performance, technologies such as a three-dimensional transistor and a through wiring are being used in the most advanced semiconductor devices. The patterning by using the multilayer resist method is carried out also in the patterning process used for forming the inner structure of the semiconductor device as mentioned above. In the patterning like this, there is a case that after the patterning a process in which the silicon-containing resist intermediate film is removed without damaging the said pattern is required. If this removal is insufficient, namely if the wafer is sent to subsequent manufacturing process steps while still having residual substances to be cleaned, yield of the device manufacturing definitely decreases. With the miniaturization movement of the device as mentioned above, a higher cleanness is required in the cleaning step. In many cases, however, the main constituent element in the conventional silicon-containing resist intermediate film and in the semiconductor device substrate is silicon; and thus, even if the attempt is made to selectively remove the silicon-containing resist intermediate film by dry etching, the constituent ingredients are so similar with each other that it has been difficult to suppress the damage to the semiconductor device substrate. This problem cannot be solved even with the wet etching using a usual fluorine-based removing agent. Therefore, a basic hydrogen peroxide aqueous solution, which is called as SC1 (Standard Clean-1) that is generally used in the semiconductor manufacturing process, may be used as the removing solution (namely, wet etching solution) not damaging the semiconductor device substrate. In this case, conversely the resist underlayer film needs to have a resistance to the basic hydrogen peroxide aqueous solution.

Besides, the process is being studied in which the substrate to be processed such as titanium nitride is processed by wet etching using the basic hydrogen peroxide aqueous solution and the resist underlayer film as a mask. In this case, too, the resist underlayer film needs to have the resistance to the basic hydrogen peroxide aqueous solution.

As the resist underlayer film composition having a fast dry etching rate and being capable of planarizing the substrate having steps to be used for the semiconductor device manufacturing, for example, a composition containing a polymer compound such as polyglycidyl methacrylate is proposed in Patent Document 2. Also as the resist underlayer film composition having a fast dry etching rate to be used for the semiconductor device manufacturing, in Patent Document 3, a composition containing a copolymer that is produced by using monomers such as (meth)acrylic acid and glycidyl (meth)acrylate is proposed, and in Patent Document 4, a composition containing a crosslinking agent and a copolymer that is produced by using monomers such as hydroxypropyl methacrylate is proposed. However, in these heretofore known compositions there has been a problem that the resistance to the basic hydrogen peroxide aqueous solution is insufficient.

As the resist underlayer film composition having the resistance to the basic hydrogen peroxide aqueous solution, in Patent Document 5, a composition containing, among others, a polymer having an epoxy group and a carboxyl group protected by using a vinyl ether compound (acetal-protected ester) is proposed for a two-layer resist process not using the resist intermediate film. However, this composition is insufficient in the planarization characteristic, and thus, this is not suitable for patterning of the substrate to be processed having irregular surface or steps highly required especially in the most advanced process, and in addition, there has been problem that the resistance to the basic hydrogen peroxide aqueous solution is still insufficient in view of practical use.

As the resist underlayer film which is excellent in the dry etching characteristic, in the resistance to the basic hydrogen peroxide aqueous solution, and in the planarization characteristic, in Patent Document 6, a composition containing among others a polymer having an epoxy group and a carboxyl group protected by using a tertiary alkyl group is proposed. However, there has been a problem in this composition that the resistance to the basic hydrogen peroxide aqueous solution is still insufficient in view of practical use.

Therefore, there have been requirements of the resist underlayer film composition to be used for the semiconductor device manufacturing having a high conformity to a wet etching process (namely, high resistance to the basic hydrogen peroxide aqueous solution) and having at the same time good gap-filling and planarization characteristics and dry etching characteristic, as well as the patterning process using this composition.

PRIOR ART DOCUMENTS

Patent Documents

Patent Document 1: Japanese Patent Laid-Open Publication No. 2004-205685
Patent Document 2: Japanese Patent Laid-Open Publication No. S61-180241
Patent Document 3: Japanese Patent 3082473
Patent Document 4: Japanese Patent 4310721
Patent Document 5: International Patent Laid-Open Publication No. 2015/030060
Patent Document 6: Japanese Patent Laid-Open Publication No. 2016-185999

SUMMARY OF INVENTION

Technical Problem

The present invention was made in view of the situation mentioned above; and thus, it has an object to provide: a resist underlayer film composition which is excellent in a resistance to a basic hydrogen peroxide aqueous solution as well as in gap-filling and planarization characteristics while having a dry etching characteristic; a patterning process using this composition; and a method for forming a resist underlayer film.

Solution to Problem

To solve the problems as mentioned above, the present invention provides a resist underlayer film composition, wherein the resist underlayer film composition is used for a multilayer resist method, the composition comprising: (A1) one, or two or more, of a compound represented by following general formula (X); and (B) an organic solvent,

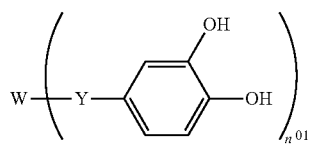

(X)

wherein "$n^{01}$" represents an integer of 1 to 10; when "$n^{01}$" is 2, W represents a sulfinyl group, a sulfonyl group, an ether group, or a divalent organic group having 2 to 50 carbon atoms; when "$n^{01}$" is an integer other than 2, W represents an $n^{01}$-valent organic group having 2 to 50 carbon atoms; and Y represents a single bond or a divalent connecting group having 1 to 10 carbon atoms and optionally having an oxygen atom.

The resist underlayer film composition as mentioned above can be excellent in the resistance to a basic hydrogen peroxide aqueous solution, in the gap-filling and planarization characteristics, and in the dry etching characteristic.

In this case, it is preferable that Y in the general formula (X) represents a single bond, a methylene group, or —OCH$_2$CH(OH)CH$_2$OC(=O)—.

The resist underlayer film composition including the structure like this can be further enhanced in the resistance to a basic hydrogen peroxide aqueous solution, in the gap-filling and planarization characteristics, and in the dry etching characteristic.

In this case, it is preferable that W in the general formula (X) represent a divalent to pentavalent heterocyclic ring group having 3 to 10 carbon atoms.

The resist underlayer film composition including the structure like this can be especially excellent in the dry etching characteristic.

In this case, it is preferable that the resist underlayer film composition further contain (A2) a polymer (1A) comprising one, or two or more, of a repeating unit represented by following general formula (1),

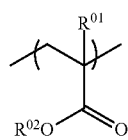

(1)

wherein $R^{01}$ represents a hydrogen atom or a methyl group; and $R^{02}$ represents a group selected from following formulae (1-1) to (1-3),

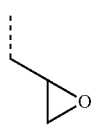

(1-1)

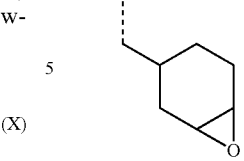

(1-2)

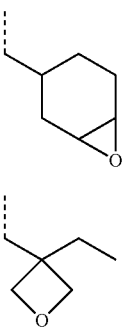

(1-3)

wherein dotted lines represent a bonding hand.

The resist underlayer film composition including the polymer like this can be further enhanced in the resistance to a basic hydrogen peroxide aqueous solution, in the gap-filling and planarization characteristics, and in the dry etching characteristic.

In this case, it is preferable that the polymer (1A) further contains one, or two or more, of a repeating unit represented by following general formula (2),

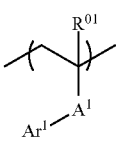

(2)

wherein $R^{01}$ represents the same as before; $A^1$ represents a single bond, —CO$_2$—, or a divalent connecting group having 2 to 10 carbon atoms and including —CO$_2$—; and $Ar^1$ represents a substituted or unsubstituted aryl group having 6 to 20 carbon atoms.

When the repeating unit as mentioned above is included in the polymer, the resist underlayer film composition containing this polymer can have suitable optical characteristics at the wavelength of 193 nm, so that especially when this composition is used in a multilayer ArF lithography, a reflected light upon exposure to a light can be suppressed; and thus, the resolution of the resist upper layer film at the time of lithography can be enhanced.

In this case, it is preferable that the polymer (1A) further contains one, or two or more, of a repeating unit represented by following general formula (3),

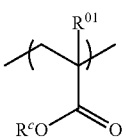

(3)

wherein $R^{01}$ represents the same as before; and $R^c$ represents a monovalent group having 3 to 20 carbon atoms and having an alicyclic structure.

When the repeating unit as mentioned above is included in the polymer, without deteriorating the optical characteristics of the resist underlayer film composition containing this polymer, the etching characteristics such as the etching rate and the pattern form after etching can be controlled in accordance with customer's requirements.

In this case, it is preferable that a weight average molecular weight of the polymer (1A) be in a range of 1,000 to 20,000.

When the molecular weight is in this range, film-formability of the resist underlayer film composition containing this polymer can be enhanced, and generation of sublimate during thermal curing can be decreased so that fouling of the equipment due to this sublimate can be suppressed. In addition, generation of coating defect can be suppressed so that the planarization and gap-filling characteristics can be further enhanced.

In this case, it is preferable that the resist underlayer film composition further contains one or more additives out of (C) an acid generator, (D) a surfactant, (E) a crosslinking agent, (F) a plasticizer, and (G) a pigment.

In the resist underlayer film composition of the present invention, if necessary, by adding thereto the additives as mentioned above, film-formability by spin coating, curing temperature, planarization and gap-filling characteristics, optical characteristic (absorption characteristic), and the like can be fine-tuned.

In this case, it is preferable that the resist underlayer film composition be the resist underlayer film composition which gives a resist underlayer film having a resistance to an ammonia-containing hydrogen peroxide aqueous solution.

In addition, it is preferable that the resist underlayer film be the resist underlayer film which does not show any peel-off of its own when a silicon substrate formed with the resist underlayer film is soaked into a 1.0% by mass hydrogen peroxide aqueous solution containing 0.5% by mass of ammonia at 70° C. for 5 minutes.

When the resist underlayer film composition as mentioned above is used, the resist underlayer film which is satisfactory in the resistance to the basic hydrogen peroxide aqueous solution can be obtained; and thus, this composition can increase the choice option with regard to the processable substrate to be processed, the resist intermediate film that is removable by wet etching, and the like.

In addition, the present invention provides a patterning process, wherein the patterning process is to form a pattern on a substrate to be processed and comprises steps of:
(I-1) forming a resist underlayer film on the substrate to be processed by using the resist underlayer film composition,
(I-2) forming a resist upper layer film on the resist underlayer film by using a photoresist composition,
(I-3) forming a pattern on the resist upper layer film by developing the resist upper layer film by using a developer after the resist upper layer film is pattern-exposed, and
(I-4) transcribing the pattern to the resist underlayer film by dry etching using as a mask the resist upper layer film formed with the pattern.

In addition, the present invention provides a patterning process, wherein the patterning process is to form a pattern on a substrate to be processed and comprises steps of:
(II-1) forming a resist underlayer film on the substrate to be processed by using the resist underlayer film composition,
(II-2) forming a resist intermediate film on the resist underlayer film,
(II-3) forming a resist upper layer film on the resist intermediate film by using a photoresist composition,
(II-4) forming a pattern on the resist upper layer film by developing the resist upper layer film by using a developer after the resist upper layer film is pattern-exposed,
(II-5) transcribing the pattern to the resist intermediate film by dry etching using as a mask the resist upper layer film formed with the pattern, and
(II-6) transcribing the pattern to the resist underlayer film by dry etching using as a mask the resist intermediate film transcribed with the pattern.

In addition, the present invention provides a patterning process, wherein the patterning process is to form a pattern on a substrate to be processed and comprises steps of:
(III-1) forming a resist underlayer film on the substrate to be processed by using the resist underlayer film composition,
(III-2) forming an inorganic hard mask intermediate film selected from a silicon oxide film, a silicon nitride film, and a silicon oxide nitride film on the resist underlayer film,
(III-3) forming an organic antireflective film on the inorganic hard mask intermediate film,
(III-4) forming a resist upper layer film on the organic antireflective film by using a photoresist composition,
(III-5) forming a pattern on the resist upper layer film by developing the resist upper layer film by using a developer after the resist upper layer film is pattern-exposed,
(III-6) transcribing the pattern to the organic antireflective film and the inorganic hard mask intermediate film by dry etching using as a mask the resist upper layer film formed with the pattern, and
(III-7) transcribing the pattern to the resist underlayer film by dry etching using as a mask the inorganic hard mask intermediate film transcribed with the pattern.

According to the patterning process of the present invention as mentioned above, fine patterning by the multilayer resist method (two-layer resist process, three-layer resist process, or the four-layer resist process) is possible; and in addition, by forming the resist underlayer film, the gap in the steps on the substrate to be processed can be filled, and the substrate to be processed can be planarized. In addition, the resist underlayer film formed by using the resist underlayer film composition of the present invention is excellent in the resistance to the basic hydrogen peroxide aqueous solution so that this can also be used in the wet etching process using the basic hydrogen peroxide aqueous solution.

In addition, after the (II-6) step, the patterning process of the present invention may be further added with a step in which the resist intermediate film transcribed with the pattern is removed by wet etching using a basic hydrogen peroxide aqueous solution.

Because the resist underlayer film formed by using the resist underlayer film composition of the present invention is excellent in the resistance to the basic hydrogen peroxide aqueous solution, the resist intermediate film can be removed by the wet etching using the basic hydrogen peroxide aqueous solution, as mentioned above.

In addition, after the (I-4) step, the (II-6) step, or the (III-7) step, the patterning process of the present invention may be further added with a step in which the pattern is transcribed to the substrate to be processed by wet etching using a basic hydrogen peroxide aqueous solution and the resist underlayer film transcribed with the pattern as a mask.

Because the resist underlayer film formed by using the resist underlayer film composition of the present invention is excellent in the resistance to the basic hydrogen peroxide aqueous solution, the pattern can be transcribed to the substrate to be processed by the wet etching using the basic hydrogen peroxide aqueous solution, as mentioned above.

In addition, after the (I-4) step, the (II-6) step, or the (III-7) step, the patterning process of the present invention may be further added with a step in which the substrate to be processed is pattern-processed by an ion implantation using as a mask the resist underlayer film transcribed with the pattern.

The patterning process as mentioned above is suitable especially for processing of the substrate having an irregular surface by the ion implantation.

In this case, after the step of the patterning process of the substrate to be processed by the ion implantation, a step in which the resist intermediate film transcribed with the pattern is removed by wet etching using a basic hydrogen peroxide aqueous solution may be added.

Because the resist underlayer film formed by using the resist underlayer film composition of the present invention is excellent in the resistance to the basic hydrogen peroxide aqueous solution, the resist intermediate film after the pattern processing by the ion implantation can also be removed by the wet etching using the basic hydrogen peroxide aqueous solution, as mentioned above.

In this case, it is preferable to use the resist underlayer film composition having a dry etching rate faster than a dry etching rate of the resist upper layer film.

When the resist underlayer film composition as mentioned above is used, the resist underlayer film used as a mask can be removed by dry etching without leaving a residual matter thereof, so that a semiconductor device having less defects can be manufactured.

In this case it is preferable that the resist underlayer film be formed by applying the resist underlayer film composition onto the substrate to be processed followed by heat-treatment thereof in a temperature range of 100° C. or more and 500° C. or less, and for a period of in a range of 10 to 600 seconds.

Under the conditions as mentioned above, the resist underlayer film having flat surface can be formed without forming voids even on the substrate having irregular surface; and in addition, the crosslinking reaction can be facilitated so that mixing with upper layer films can be prevented. In addition, when the heat-treatment temperature and the heat-treatment period are properly controlled within the above-mentioned ranges, the gap-filling and planarization characteristics as well as the curing characteristic, these characteristics matching with individual use, can be obtained.

In this case, it is preferable to use, as the substrate to be processed, a substrate having a structural body with a height of 30 nm or more, or having a step.

Because the resist underlayer film formed by using the resist underlayer film composition of the present invention is excellent in the gap-filling and planarization characteristics, the resist underlayer film having flat surface can also be formed without forming voids even on the substrate having the structural body with the height of 30 nm or more, or having the step.

In addition, the present invention provides a method for forming a resist underlayer film wherein the resist underlayer film composition mentioned above is applied onto a substrate to be processed, and then, the resist underlayer film composition is subjected to heat-treatment in a temperature range of 100° C. or more and 500° C. or less, and for a period of in a range of 10 to 600 seconds to form a cured film.

When the method for forming the resist underlayer film is the one as mentioned above, the resist underlayer film which is excellent in the resistance to the basic hydrogen peroxide aqueous solution as well as in the gap-filling and planarization characteristics while having the dry etching characteristic can be formed. In addition, when the baking temperature and the baking period are properly controlled within the above-mentioned ranges, the gap-filling and planarization characteristics as well as the curing characteristic, these characteristics matching with individual use, can be obtained.

In this case, it is preferable to use a substrate having a structural body with a height of 30 nm or more, or having a step as the substrate to be processed.

The method of the present invention for forming the resist underlayer film is useful especially for forming a planarized organic film without voids on the substrate having the structural body with the height of 30 nm or more, or having the step.

Advantageous Effects of Invention

As explained above, according to the resist underlayer film composition of the present invention, the resist underlayer film composition which is excellent in the resistance to the basic hydrogen peroxide aqueous solution, in the gap-filling and planarization characteristics, and in the dry etching characteristic can be obtained.

In addition, according to the patterning process of the present invention, a fine pattern can be formed by the multilayer resist method (two-layer resist process, three-layer resist process, or the four-layer resist process); and in addition, by forming the resist underlayer film, the steps on the substrate to be processed can be filled, and the substrate to be processed can be planarized. Therefore, the patterning process of the present invention can be favorably used in the wet etching process, in the planarization process by formation of the underlayer film, and in the removal process of the underlayer film by dry etching; and thus, this method is extremely useful as the patterning process used in the multilayer resist process used in the fine patterning for the semiconductor device manufacturing.

In addition, according to the method of the present invention for forming a resist underlayer film, the resist underlayer film which is excellent in the resistance to the basic hydrogen peroxide aqueous solution as well as in the gap-filling and planarization characteristics while having the dry etching characteristic can be formed.

DESCRIPTION OF EMBODIMENTS

Figure 1:
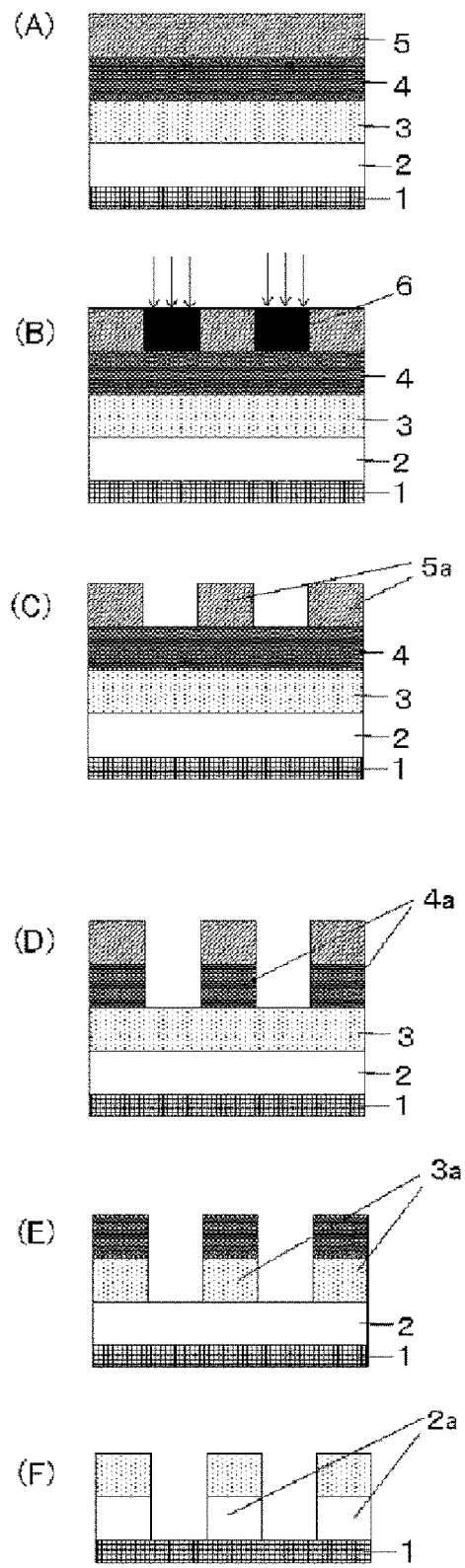
FIG. 1 is an explanatory drawing of one example of the patterning process by the three-layer resist process according to the present invention.

Hereunder, the present invention will be explained in more detail. As mentioned above, those having been wanted are: the resist underlayer film composition which is excellent in the resistance to the basic hydrogen peroxide aqueous solution as well as in the gap-filling and planarization characteristics while having the dry etching characteristic; the patterning process using this composition; and the method for forming a resist underlayer film.

In order to realize the wet etching processing in the multilayer lithography using a resist underlayer film, more desirably, in order to further realize gap-filling and planarization by formation of the underlayer film as well as removal of the underlayer film by dry etching, inventors of the present invention explored various resist underlayer film compositions and patterning processes. As a result, it was found that the resist underlayer film composition mainly comprising a compound having a certain structure as well as the patterning process is very effective for these purposes; and on the basis of these findings, the present invention could be completed.

Namely, the resist underlayer film composition of the present invention is a resist underlayer film composition to be used for a multilayer resist method, the composition comprising: (A1) one, or two or more, of a compound represented by following general formula (X); and (B) an organic solvent,

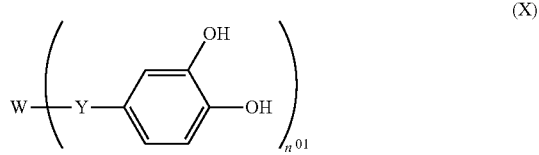

wherein "$n^{01}$" represents an integer of 1 to 10; when "$n^{01}$" is 2, W represents a sulfinyl group, a sulfonyl group, an ether group, or a divalent organic group having 2 to 50 carbon atoms; when "$n^{01}$" is an integer other than 2, W represents an $n^{01}$-valent organic group having 2 to 50 carbon atoms; and Y represents a single bond or a divalent connecting group having 1 to 10 carbon atoms and optionally having an oxygen atom.

Hereunder, the present invention will be explained in detail; however, the present invention is not limited to these descriptions.

<Resist Underlayer Film Composition>

The resist underlayer film composition of the present invention is a resist underlayer film composition to be used for a multilayer resist method, the composition comprising: (A1) one, or two or more, of a compound represented by following general formula (X); and (B) an organic solvent, whereby the resist underlayer film composition of the present invention contains the (A1) component as the base resin,

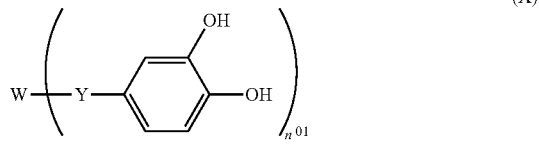

wherein "$n^{01}$" represents an integer of 1 to 10; when "$n^{01}$" is 2, W represents a sulfinyl group, a sulfonyl group, an ether group, or a divalent organic group having 2 to 50 carbon atoms; when "$n^{01}$" is an integer other than 2, W represents an $n^{01}$-valent organic group having 2 to 50 carbon atoms; and Y represents a single bond or a divalent connecting group having 1 to 10 carbon atoms and optionally having an oxygen atom. Hereunder, each component will be explained in more detail.

[(A1) Component]

The (A1) component is one, or two or more, of a compound represented by the general formula (X). The resist underlayer film composition of the present invention which contains the compound represented by the general formula (X) is excellent in adhesion with the substrate to be processed, especially with an inorganic substrate to be processed, so that delamination during wet etching by using the basic hydrogen peroxide aqueous solution can be suppressed, thereby it is presumed that excellent resistance to the basic hydrogen peroxide aqueous solution is resulted. Meanwhile, it is presumed that this excellent adhesion with the substrate to be processed is realized mainly by presence of a 3,4-dihydroxy phenyl group in the molecule thereof.

In the general formula (X), $n^{01}$ represents an integer of 1 to 10; when $n^{01}$ is 2, W represents a sulfinyl group, a sulfonyl group, an ether group, or a divalent organic group having 2 to 50 carbon atoms; when $n^{01}$ is an integer other than 2, W represents an $n^{01}$-valent organic group having 2 to 50 carbon atoms. Namely, W represents a sulfinyl group, a sulfonyl group, an ether group, or a monovalent to decavalent organic group having the structure that 1 to 10 hydrogen atom(s) is/are removed from an organic compound having 2 to 50 carbon atoms. The structure in which 1 to 10 hydrogen atoms(s) is/are added to W (namely, the organic compound having 2 to 50 carbon atoms) may contain a linear, branched, or cyclic, saturated or unsaturated hydrocarbon group, an aromatic group, a heteroaromatic group, an ether group, a hydroxy group, an ester group, a keto group, an amino group, a halogen group, a sulfide group, a carboxyl group, a sulfo group, an amide group, an imide group, a cyano group, an aldehyde group, an imino group, an urea group, a carbamate group, a carbonate group, a nitro group, or a sulfone group.

Especially, W is preferably a divalent to pentavalent heterocyclic group having 3 to 10 carbon atoms. By selecting a proper structure as W, characteristics such as etching resistance, heat resistance, optical constants, polarity, and flexibility can be controlled in accordance with the use. More specific examples of the structure of W are shown below, but the structure thereof is not limited to them. Meanwhile, in the following formulae, the dotted lines represent a bonding hand,

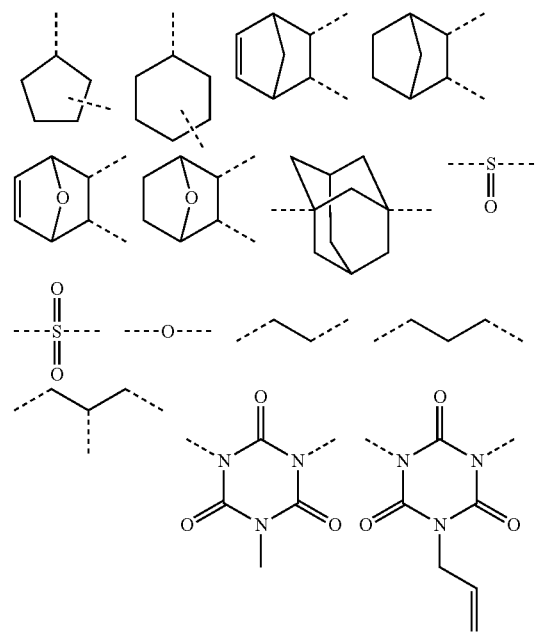

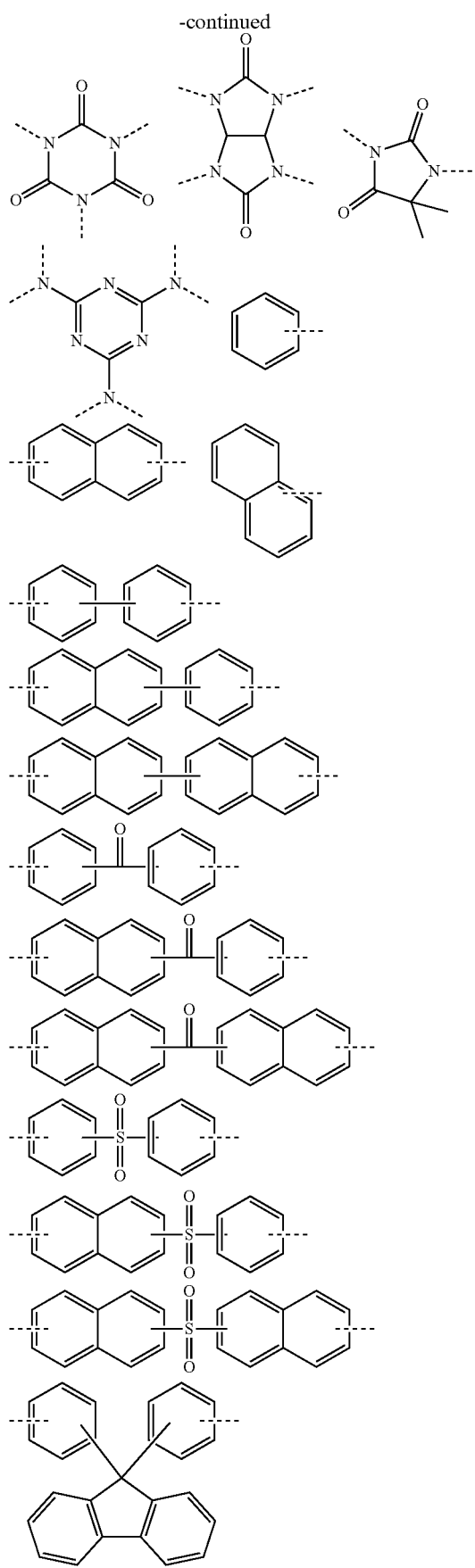

-continued
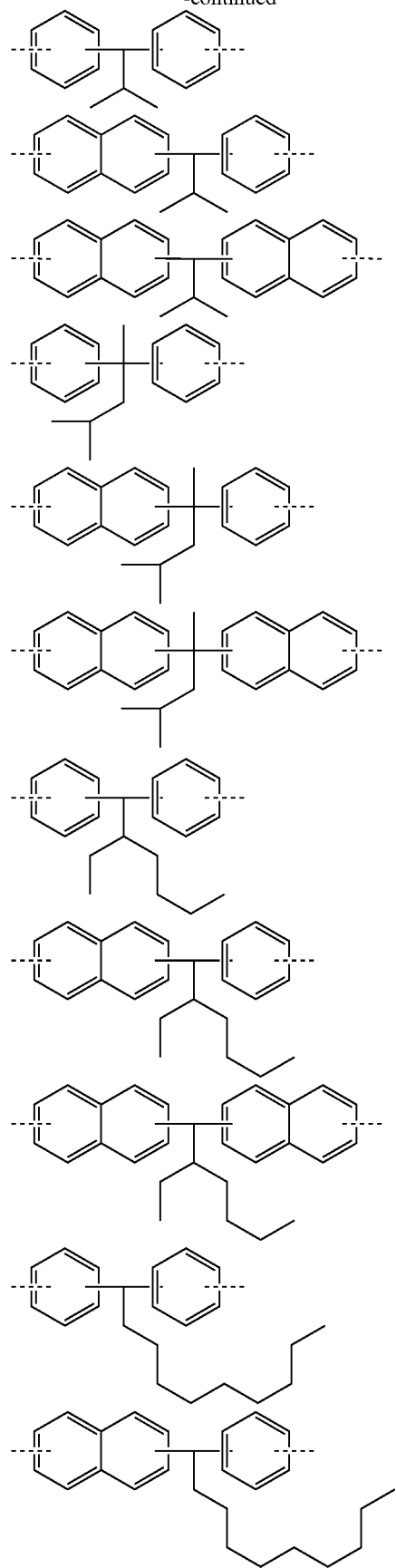
-continued
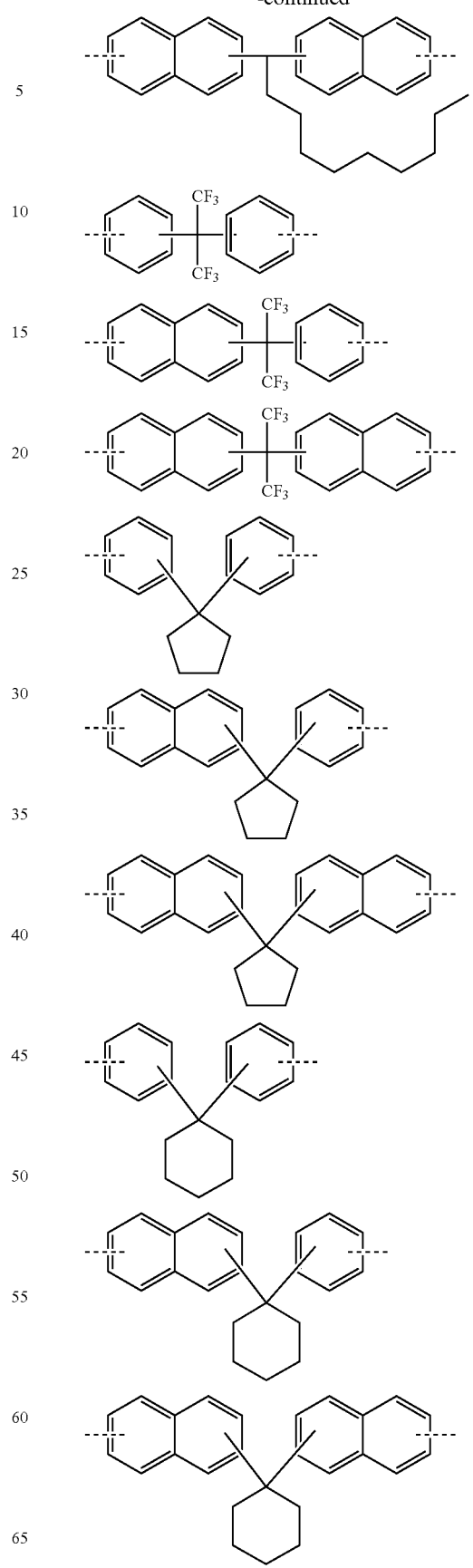

-continued
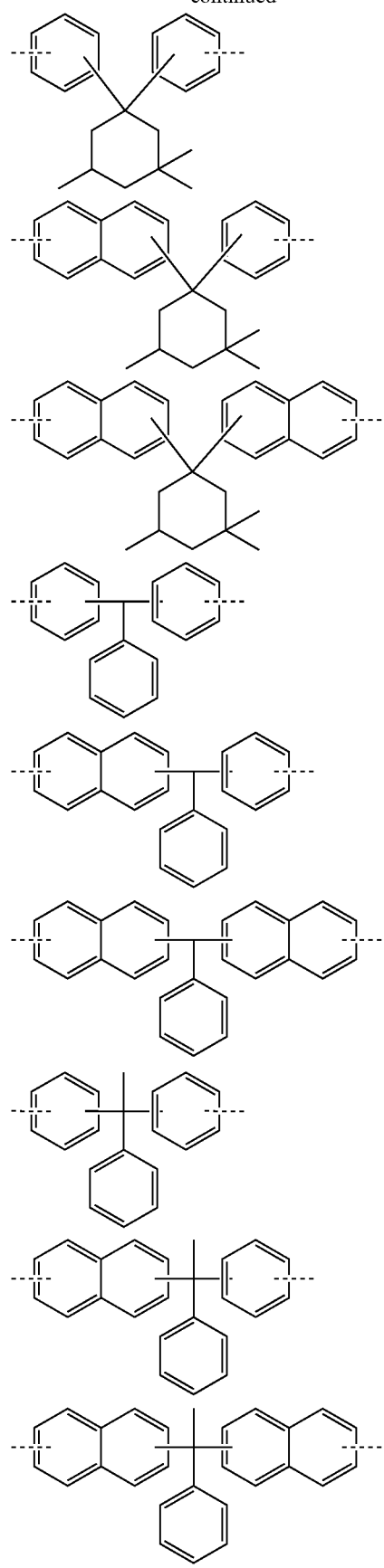
-continued
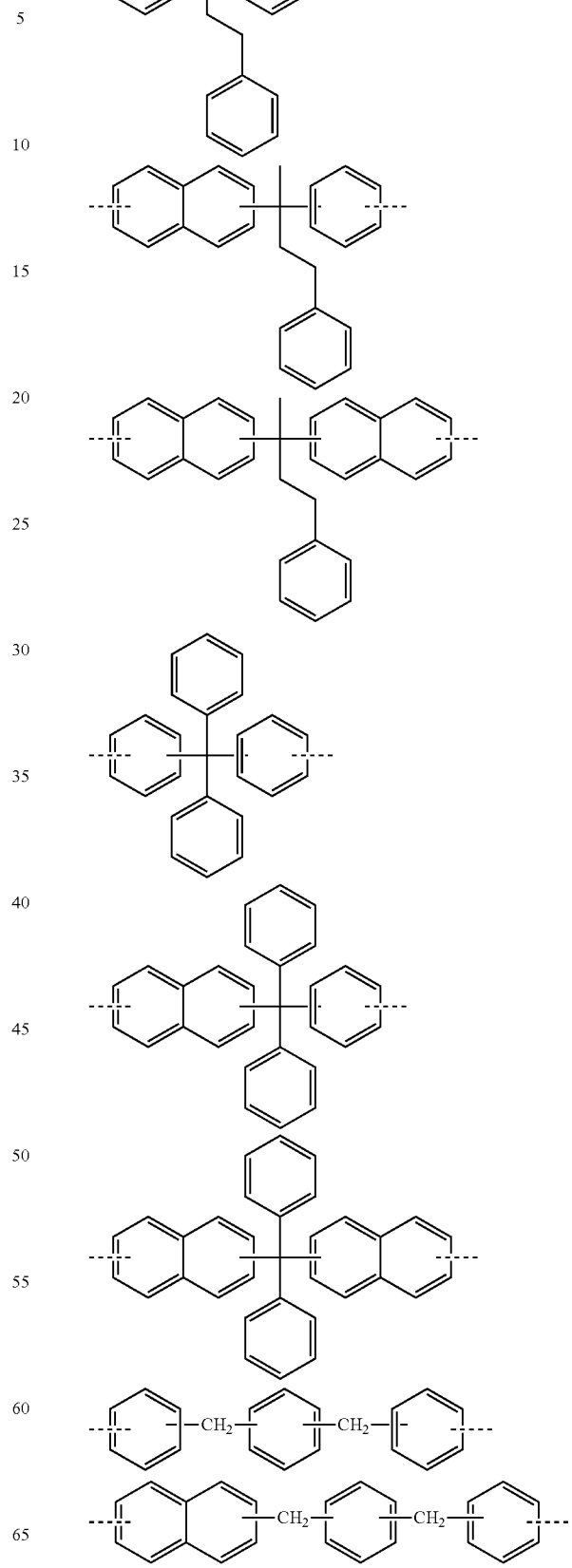

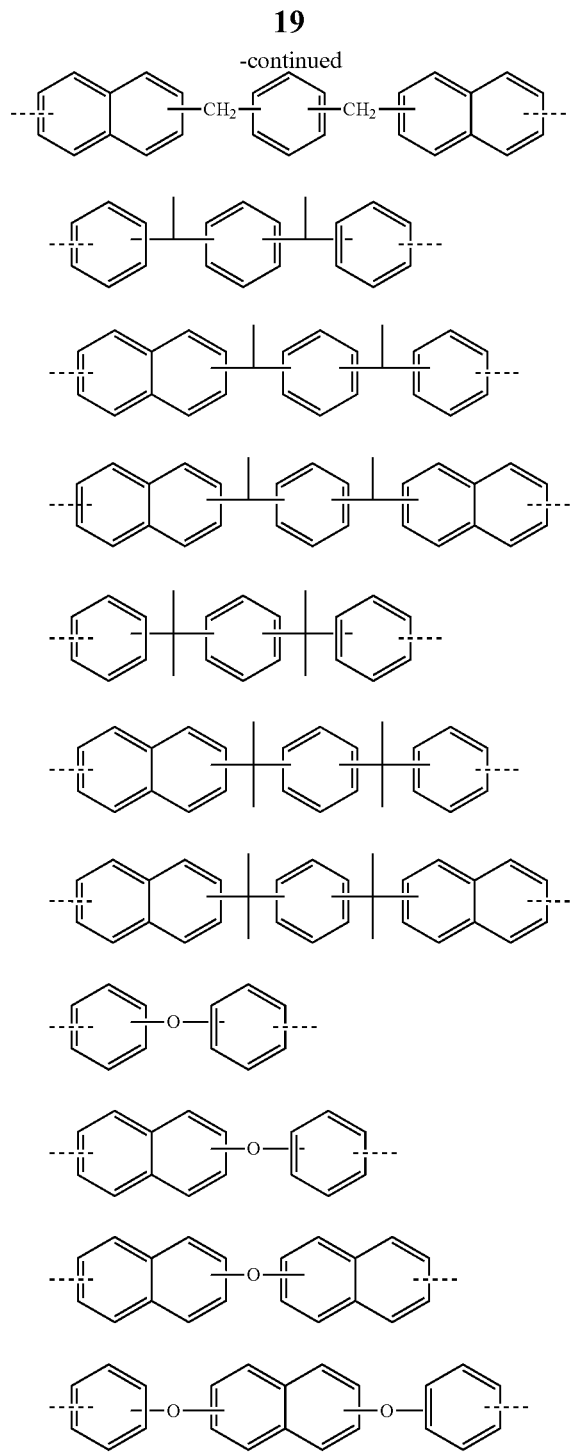

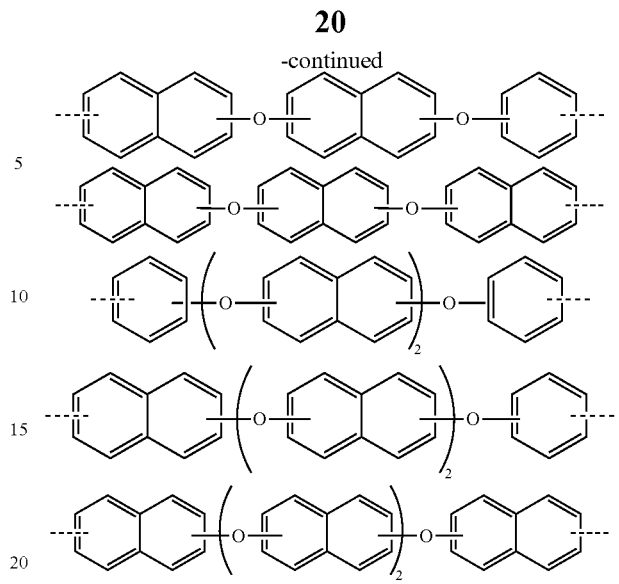

In the general formula (X), Y represents a single bond or a divalent connecting group having 1 to 10 carbon atoms and optionally having an oxygen atom. By selecting a proper structure as Y, characteristics such as heat resistance, polarity, and flexibility can be controlled in accordance with the use. Specifically, preferable example of Y includes a single bond, a methylene group, an ethylene group, a propylene group, a trimethylene group, a butylene group, an isopropylidene group, an ethylidene group, a carbonyl group, a tetramethylene group, a cyclohexanediyl group, a decanediyl group, a phenylene group, —$CO_2$—, —$OCO_2$—, —$CO_2CH_2$—, —$CO_2CH_2CH_2$—, —$CO_2CH_2CH_2CH_2$—, —$CO_2CH(CH_3)$—, —$CO_2CH_2CH_2CH_2CH_2$—, —$CO_2CH_2CH_2CH_2CH_2CH_2CH_2CH_2CH_2CH_2$—, —$CO_2CH_2CH_2O$—, —$CO_2CH_2CH_2OCH_2CH_2O$—, —$CO_2CH_2CH_2OCH_2CH_2OCH_2CH_2O$—, —$OCH_2CH(OH)CH_2O$—, —$OCH_2CH(OH)CH_2O_2C$— (namely, —$OCH_2CH(OH)CH_2OC(=O)$—), but not limited to them.

In the present invention, the compound of the (A1) component may be used singly or as a mixture of two or more of the compounds. The molecular weight (formula weight) of the compound of the (A1) component is preferably in the range of 300 to 5,000, while especially preferably in the range of 500 to 2,500. When the molecular weight is 300 or more, there is no risk of poor film-formability or fouling of the equipment due to increase in the sublimate during thermal curing. When the molecular weight is 5,000 or less, there is no risk of deterioration in the planarization and gap-filling characteristics.

Specific example of the compound of the (A1) component can be shown below; however, the compound is not limited to them,

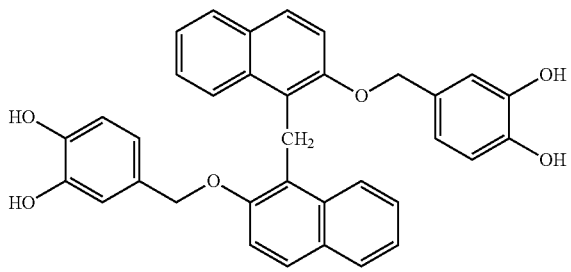

-continued
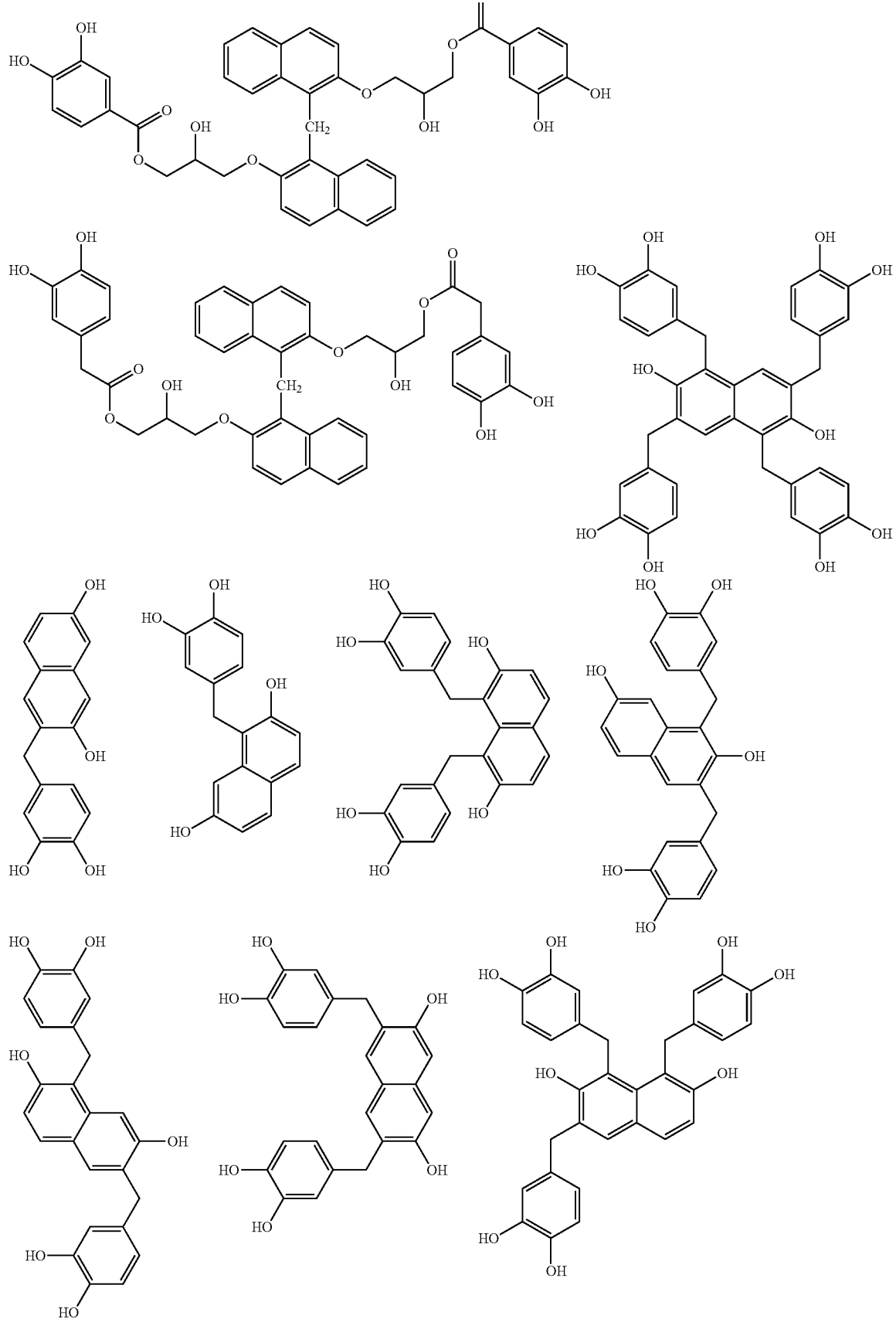

-continued
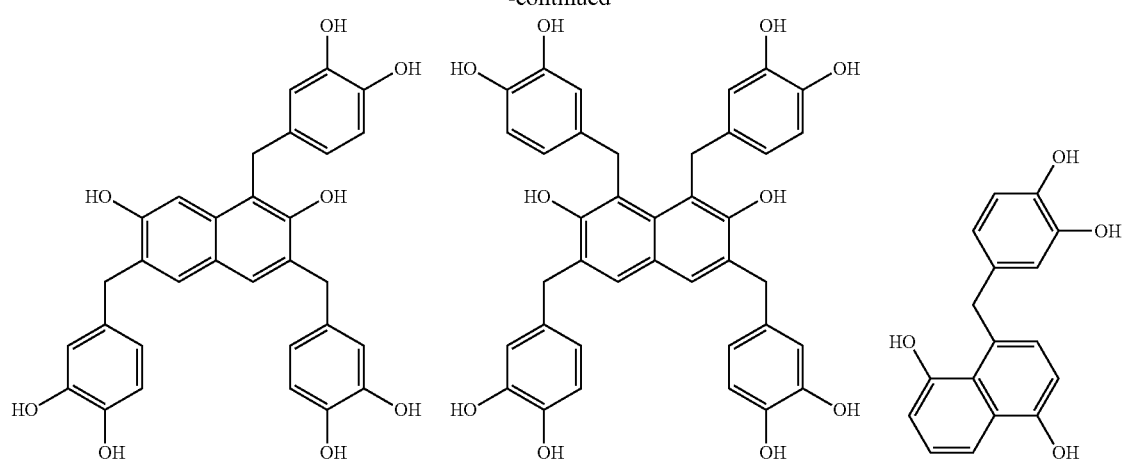
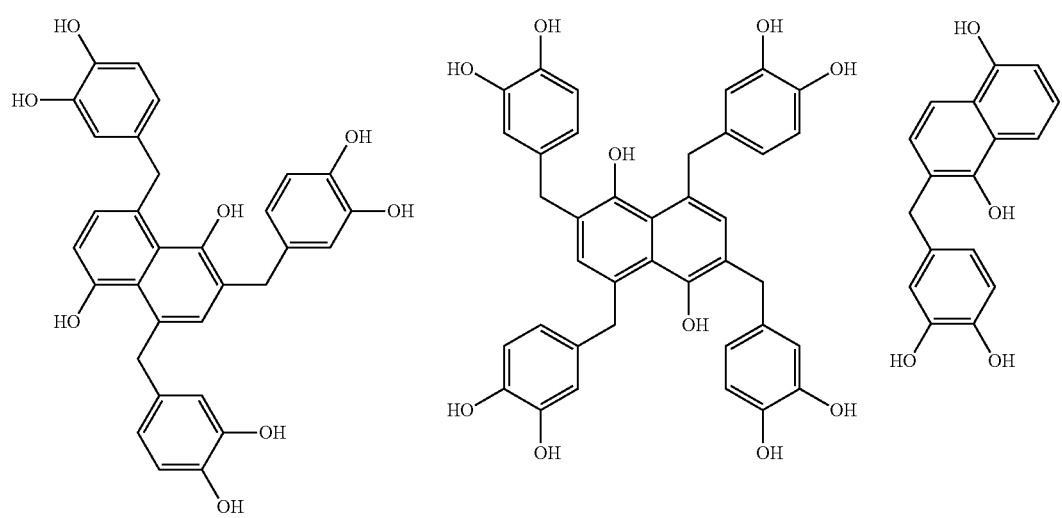
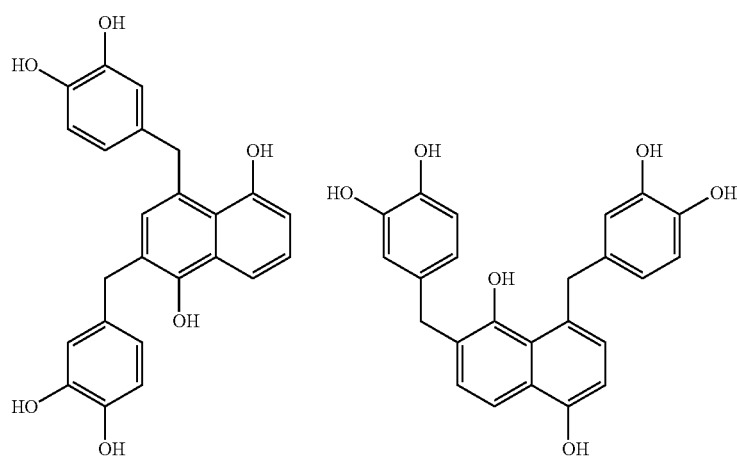

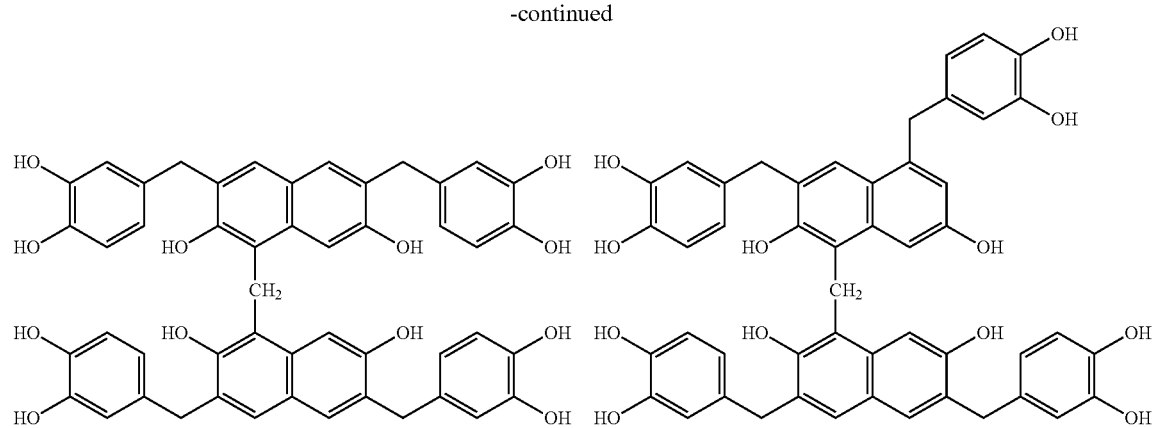
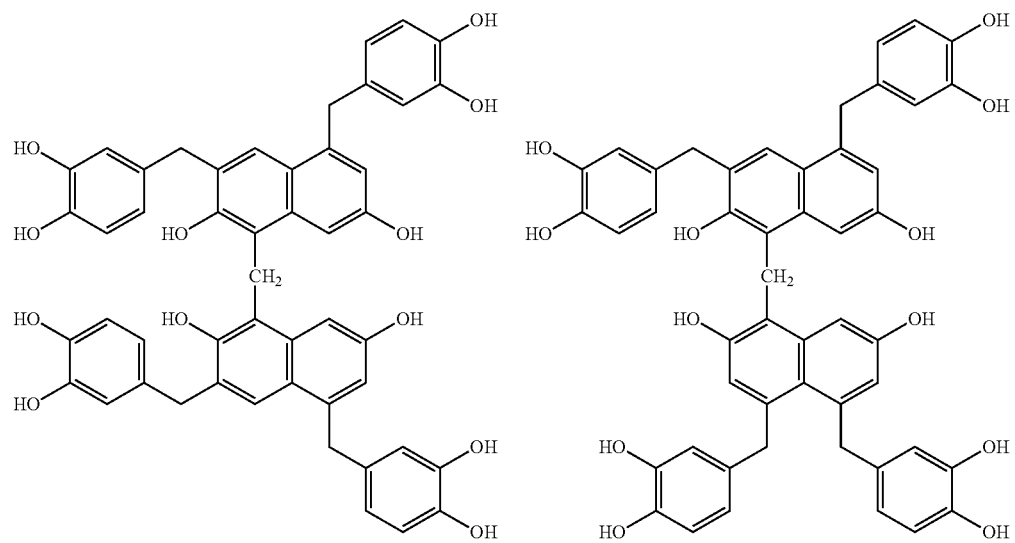
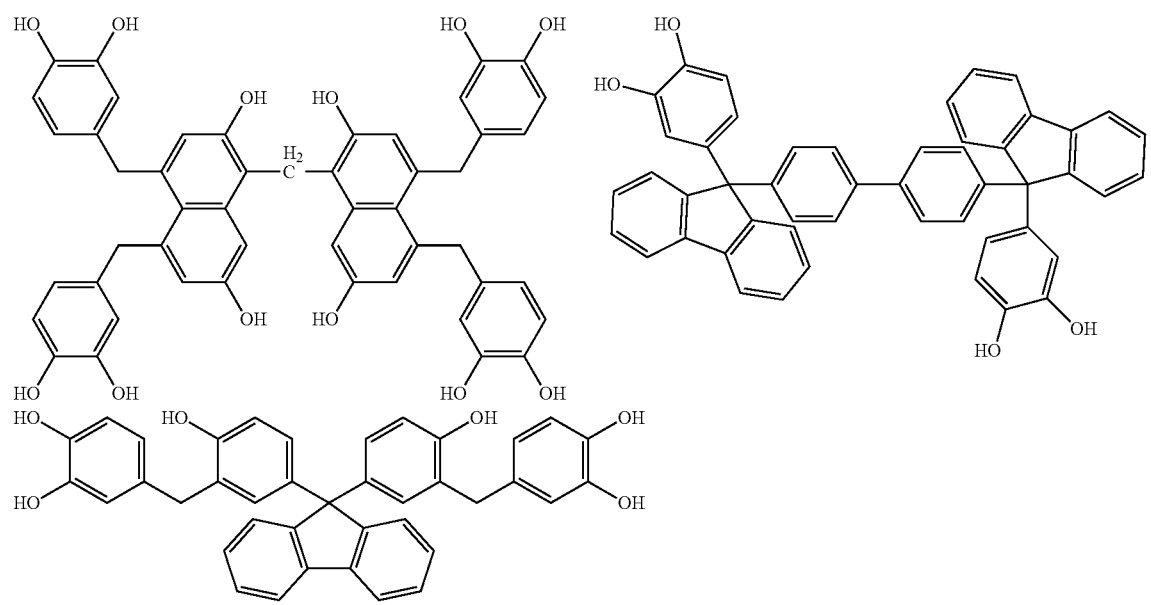

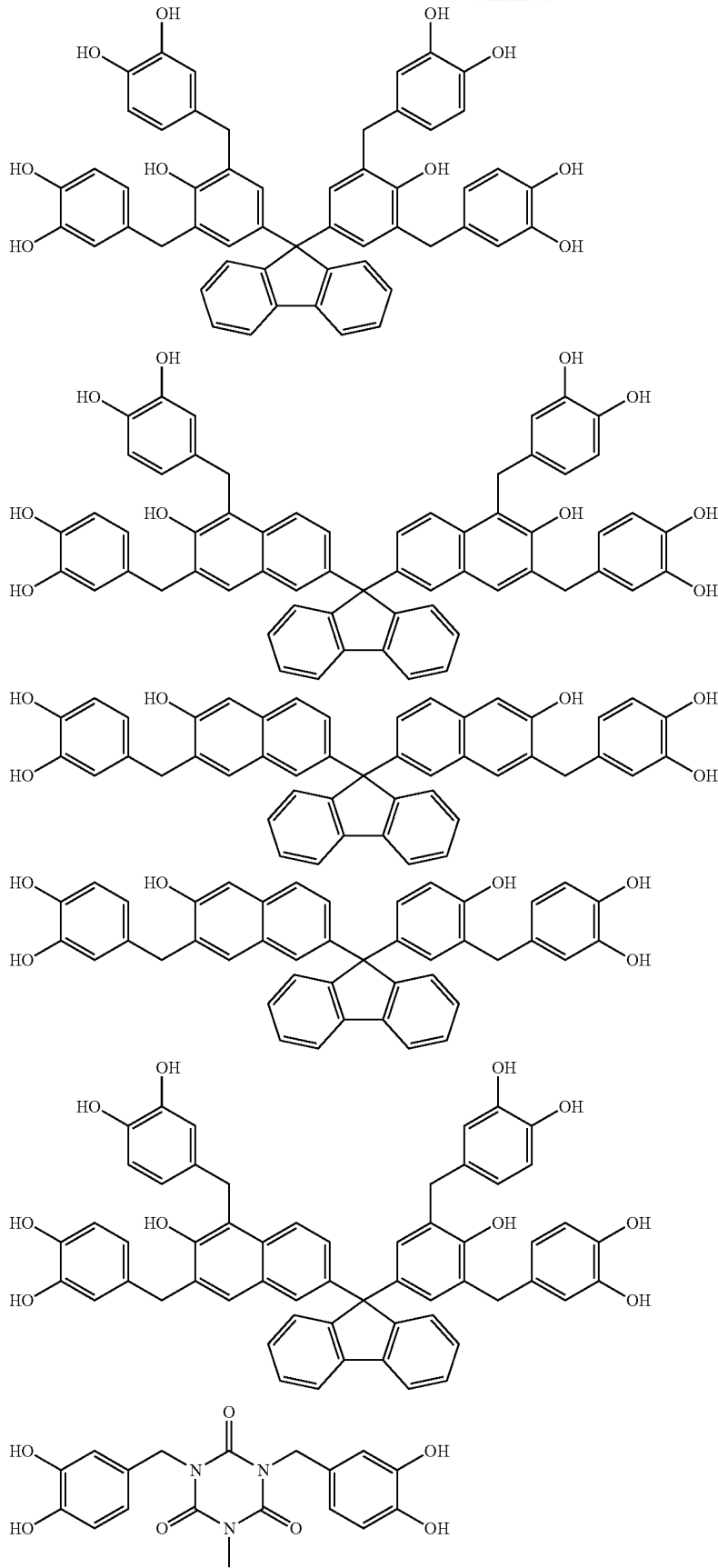

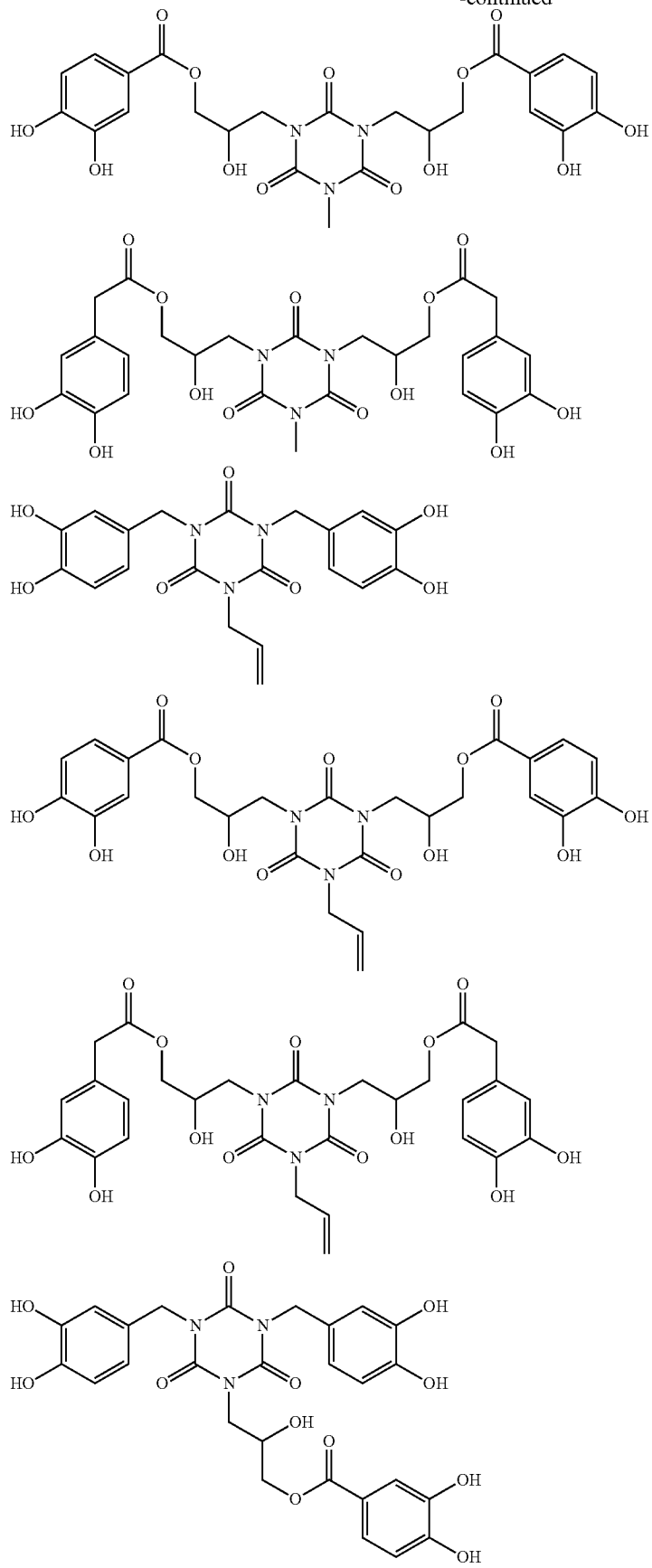

31
-continued
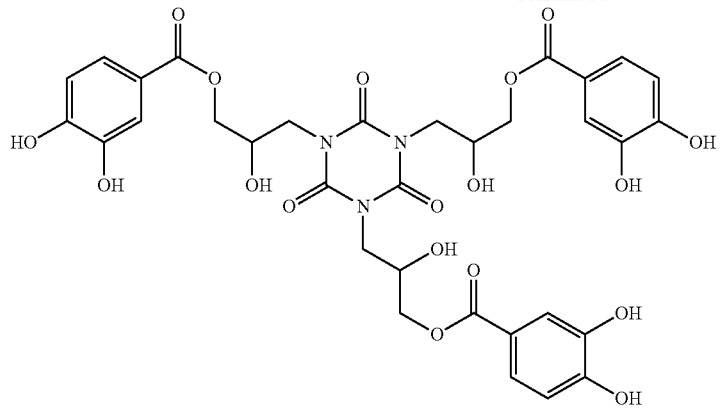
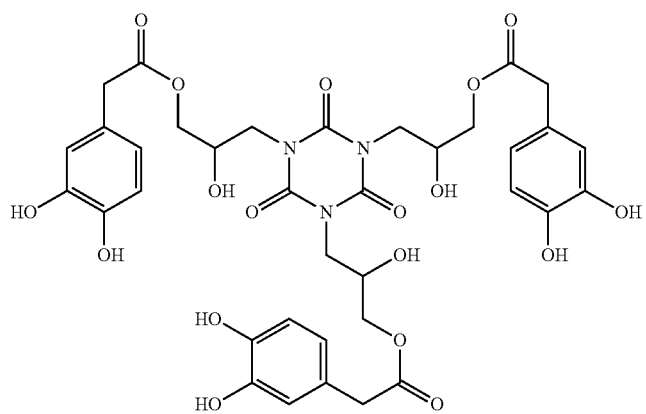
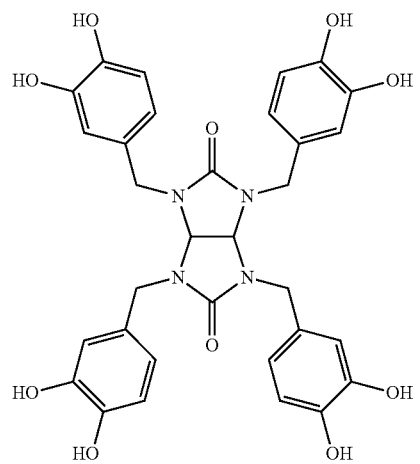
32
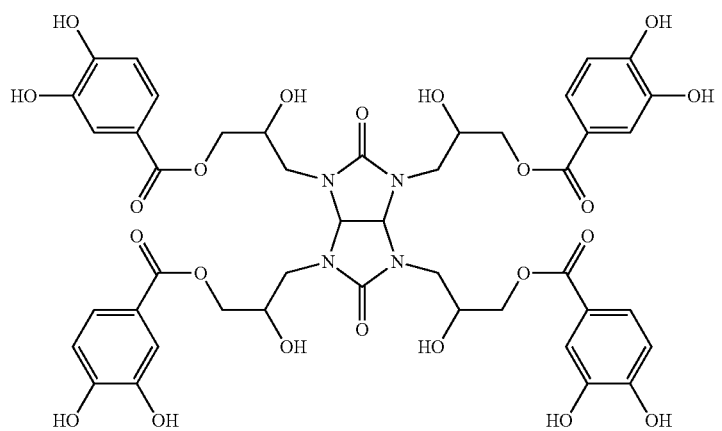
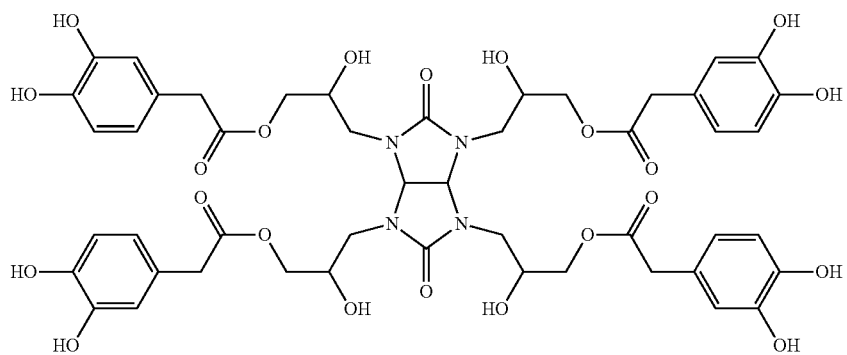

[(A2) Component]

It is preferable that the resist underlayer film composition of the present invention further contain, as the (A2) component, the polymer (1A) which contains one, or two or more, of the repeating unit represented by the following general formula (1),

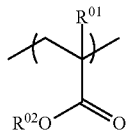

(1)

wherein $R^{01}$ represents a hydrogen atom or a methyl group; and $R^{02}$ represents a group selected from following formulae (1-1) to (1-3),

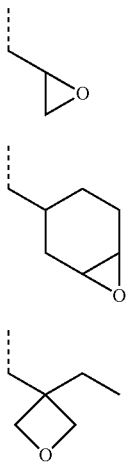

(1-1)

(1-2)

(1-3)

wherein the dotted lines represent a bonding hand.

By blending the polymer (1A), not only the film-formability by application can be increased but also the controllable range of the etching resistance can be expanded. When the polymer (1A) is blended, the blending amount thereof is preferably in the range of 5 to 2,000 parts by mass, while more preferably in the range of 20 to 1,000 parts by mass, relative to 100 parts by mass of the compound of the (A1) component. When the blending amount of the polymer (1A) is 5 or more parts by mass, the blending effect can be obtained sufficiently well; on the contrary, when the blending amount of the polymer (1A) is 2,000 or less parts by mass, sufficient resistance to the basic hydrogen peroxide aqueous solution can be obtained.

The polymer (1A) is characterized by that it contains one, or two or more, of the repeating unit represented by the general formula (1). The repeating unit represented by the general formula (1) provides the polymer (1A) with a sufficient thermal curability and with a preventive effect of intermixing with the upper layer films. In addition, it is presumed that this can contribute to the resistance to the basic hydrogen peroxide aqueous solution to a certain degree.

In the general formula (1), $R^{01}$ represents a hydrogen atom or a methyl group. When $R^{01}$ is a hydrogen atom, the polymer (1A) is excellent in its flowability, thereby sometimes contributing to enhancement of the planarization and gap-filling characteristics as well as enhancement of the etching rate because of small carbon content. On the other hand, when $R^{01}$ is a methyl group, there is a case that the resist underlayer film composition of the present invention has excellent film formability. $R^2$ represents the group selected from the above formulae (1-1) to (1-3).

The polymer (1A) may contain only one, or two or more, of the repeating unit represented by the general formula (1). Specifically, the repeating units represented by the general formula (1) are as follows,

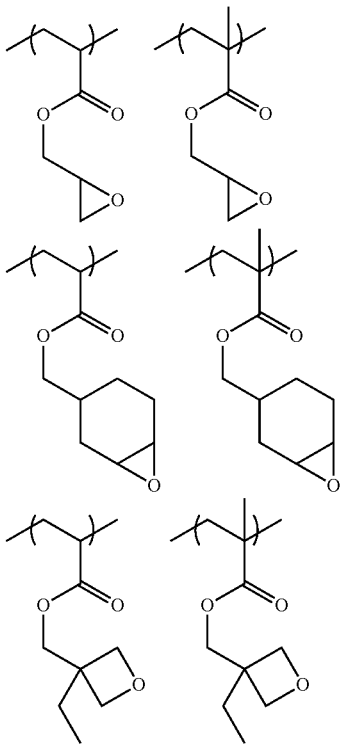

It is more preferable that the polymer (1A) further contain one, or two or more, of the repeating unit represented by the following general formula (2),

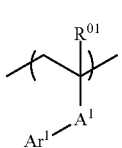

(2)

wherein $R^{01}$ represents the same as before; $A^1$ represents a single bond, —$CO_2$—, or a divalent connecting group having 2 to 10 carbon atoms and including —$CO_2$—; and $Ar^1$ represents a substituted or an unsubstituted aryl group having 6 to 20 carbon atoms.

The repeating unit represented by the general formula (2) can provide the base resin with suitable optical characteristics at the wavelength of 193 nm; and thus, the reflected light can be suppressed especially during the time of exposure to a light in the multilayer ArF lithography, and thereby excellent resolution can be obtained. Meanwhile, in order to suppress the reflected light, it is preferable that the refractive index "n" be in the range of 1.5 to 1.9 and the extinction coefficient "k" be in the range of 0.1 to 0.5 as the optical constants of the resist underlayer film composition.

In the general formula (2), $R^{01}$ represents a hydrogen atom or a methyl group. $A^1$ represents a single bond, —$CO_2$—, or a divalent connecting group having 2 to 10 carbon atoms and including —$CO_2$—. Specific example of $A^1$ includes a single bond, —$CO_2$—, —$CO_2CH_2$—, —$CO_2CH_2CH_2$—, —$CO_2CH_2CH_2CH_2$—, —$CO_2CH$ ($CH_3$)—, —$CO_2CH_2CH_2CH_2CH_2$—, —$CO_2CH_2CH_2CH_2CH_2CH_2$—, —$CO_2CH_2CH_2CH_2$—, —$CO_2CH_2CH_2O$—, —$CO_2CH_2CH_2OCH_2CH_2O$—, and —$CO_2CH_2CH_2OCH_2CH_2OCH_2CH_2O$—, but not limited to them. $Ar^1$ represents a substituted or unsubstituted aryl group having 6 to 20 carbon atoms. More specific example of the $Ar^1$ includes a phenyl group, a tollyl group, a xylyl group, a methoxyphenyl group, a tert-butoxyphenyl group, a hydroxyphenyl group, an acetylphenyl group, a naphthyl group, a methylnaphthyl group, an anthracenyl group, a phenanthrenyl group, and a pyrenyl group, wherein especially preferable groups are a phenyl group and a tert-butoxyphenyl group, though not limited to them.

It is more preferable that the polymer (1A) further contain one, or two or more, of the repeating unit represented by the following general formula (3),

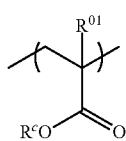

(3)

wherein $R^{01}$ represents the same as before; and $R^c$ represents a monovalent group having 3 to 20 carbon atoms and having an alicyclic structure.

When the repeating unit represented by the general formula (3) is appropriately introduced, without deteriorating optical characteristics of the base resin the etching characteristics such as the etching rate and the pattern form after etching can be controlled in accordance with the customer's requirement.

In the general formula (3), $R^{01}$ represents a hydrogen atom or a methyl group. $R^c$ represents a monovalent group having 3 to 20 carbon atoms and having an alicyclic structure. More specific example of $R^c$ includes a cyclopropyl group, a cyclobutyl group, a cyclopentyl group, a cyclohexyl group, a cycloheptyl group, a dicycloheptyl group, a dicyclooctyl group, a dicyclononyl group, a dicyclodecanyl group, a tricyclodecanyl group, an adamantyl group, a tetracyclododecanyl group, a cyclohexylmethyl group, a dicycloheptylmethyl group, an isobornyl group, a menthyl group, a hydroxycyclohexyl group, a hydroxydicycloheptyl group, a hydroxyadamantyl group, a 1-methylcyclopropyl group, a 1-methylcyclopentyl group, a 1-ethylcyclopentyl group, a 1-methylcyclohexyl group, a 1-ethylcyclohexyl group, a 1-cyclopentylcyclopentyl group, a 1-cyclohexylcyclopentyl group, a 1-methylcyclohexyl group, a 1-ethylcyclohexyl group, a 1-cyclopentylcyclohexyl group, a 1-cyclohexylcyclohexyl group, a 2-methyl-2-norbonyl group, a 2-ethyl-2-norbonyl group, a 8-methyl-8-tricyclo[$5.2.1.0^{2,6}$] decyl group, a 8-ethyl-8-tricyclo[$5.2.1.0^{2,6}$]decyl group, a 3-methyl-3-tetracyclo[$4.4.0.1^{2,5}.1^{7,10}$]dodecyl group, a 3-ethyl-3-tetracyclo[$4.4.0.1^{2,5}.1^{7,10}$]dodecyl group, a 2-methyl-2-adamantyl group, a 2-ethyl-2-adamantyl group, a 1-adamantyl-1-methylethyl group, a 1-methyl-3-oxo-1-cyclohexyl group, a 1-methyl-1-(tetrahydrofuran-2-yl)ethyl group, a 5-hydroxy-2-methyl-2-adamantyl group, a 5-hydroxy-2-ethyl-2-adamantyl group, a butyrolactonyl group, a valerolactonyl group, a 1,3-cyclohexanecarbolactonyl group, a 4-oxa-5-oxotricyclo[$5.2.1.0^{2,6}$]decyl group, a 2,6-norbornanecarbolactone-3-ylmethyl group, a 2,6-norbornanecarbolactone-5-yl group, a 3-methoxycarbonyl-2,6-norbornanecarbolactone-5-yl group, and a 7-oxa-2,6-norbornanecarbolactone-5-yl group. When an optimum structure is selected as $R^c$ in accordance with the use, properties of the entire polymer such as the carbon density and polarity can be optimally controlled so that the characteristics of the underlayer film which uses this polymer can be controlled as well.

In the present invention, the mole fraction of the repeating unit represented by the general formula (1) in the polymer (1A) is preferably in the range of 20% or more and 90% or less, while more preferably in the range of 25% or more and 70% or less. When the mole fraction thereof is 20% or more, sufficient curability can be obtained. When the mole fraction thereof is 70% or less, sufficient planarization and etching characteristics can be obtained. The mole fraction of the repeating unit represented by the general formula (2) is preferably in the range of 5% or more and 50% or less, while more preferably in the range of 5% or more and 40% or less. When the mole fraction thereof is 5% or more, the resolution at the time of performing a lithography of the upper layer film is satisfactory; and when the mole fraction thereof is 50% or less, the etching characteristic is satisfactory.

Meanwhile, when the sum of mole fractions of the repeating units represented by the general formulae (1) and (2) does not reach 100%, the base resin includes other repeating units. In this case, illustrative example of the other repeating unit includes the repeating unit represented by the general formula (3); α, β-unsaturated carboxylate esters such as other acrylate esters, other methacrylate esters, crotonate esters, maleate esters, and itaconate esters; α,β-unsaturated carboxylic acids such as methacrylic acid, acrylic acid, maleic acid, and itaconic acid; acrylonitrile; methacrylonitrile; α, β-unsaturated lactones such as 5,5-dimethyl-3-methylene-2-oxotetrahydrofuran; cyclic olefins such as norbornene derivatives and tetracyclo[$4.4.0.1^{2,5}.1^{7,10}$]dodecene derivatives; α, β-unsaturated carboxylic acid anhydrides such as maleic anhydride and itaconic anhydride; allyl ethers; vinyl ethers; vinyl esters; and vinyl silanes.

It is preferable that the polymer (1A) have the weight average molecular weight of in the range of 1,000 to 20,000. The weight average molecular weight is on the basis of the value measured by a gel permeation chromatography (solvent of tetrahydrofuran and the polystyrene standard). The weight average molecular weight of the polymer (1A) is preferably in the range of 1,000 to 20,000, more preferably in the range of 1,500 to 15,000, while still more preferably in the range of 2,000 to 10,000. When the weight average molecular weight is 1,000 or more, there is no risk of poor film-formability or fouling of the equipment due to increase in the sublimate during thermal curing. On the other hand, when the weight average molecular weight is 20,000 or less, there is no risk of formation of a coating defect or deterioration in the planarization and gap-filling characteristics due to decrease in the flowability.

In the resist underlayer film composition of the present invention, the glass transition temperature of the polymer (1A) is preferably 50° C. or less, while more preferably 25° C. or less. The resist underlayer film composition containing the polymer (1A) like this is excellent in the planarization and gap-filling characteristics due to formation of the resist underlayer film, so that this is especially desirable for processing of the substrate having an irregular surface.

In the resist underlayer film composition of the present invention, the GPC dispersibility of the polymer (1A) is preferably 2.0 or less, while more preferably 1.8 or less. In the resist underlayer film composition like this, generation of the sublimate during formation of the resist underlayer film is small, so that fouling of the equipment can be suppressed; and thus, this is excellent in the practical use.

Specific example of the polymer (1A) includes the polymers described below, but the polymer (1A) is not limited to them. In the formulae, Me represents a methyl group; Bu represents a butyl group; Ph represents a phenyl group; tBu represents a tert-butyl group; and Ac represents an acetyl group; and the same are applied hereinafter,

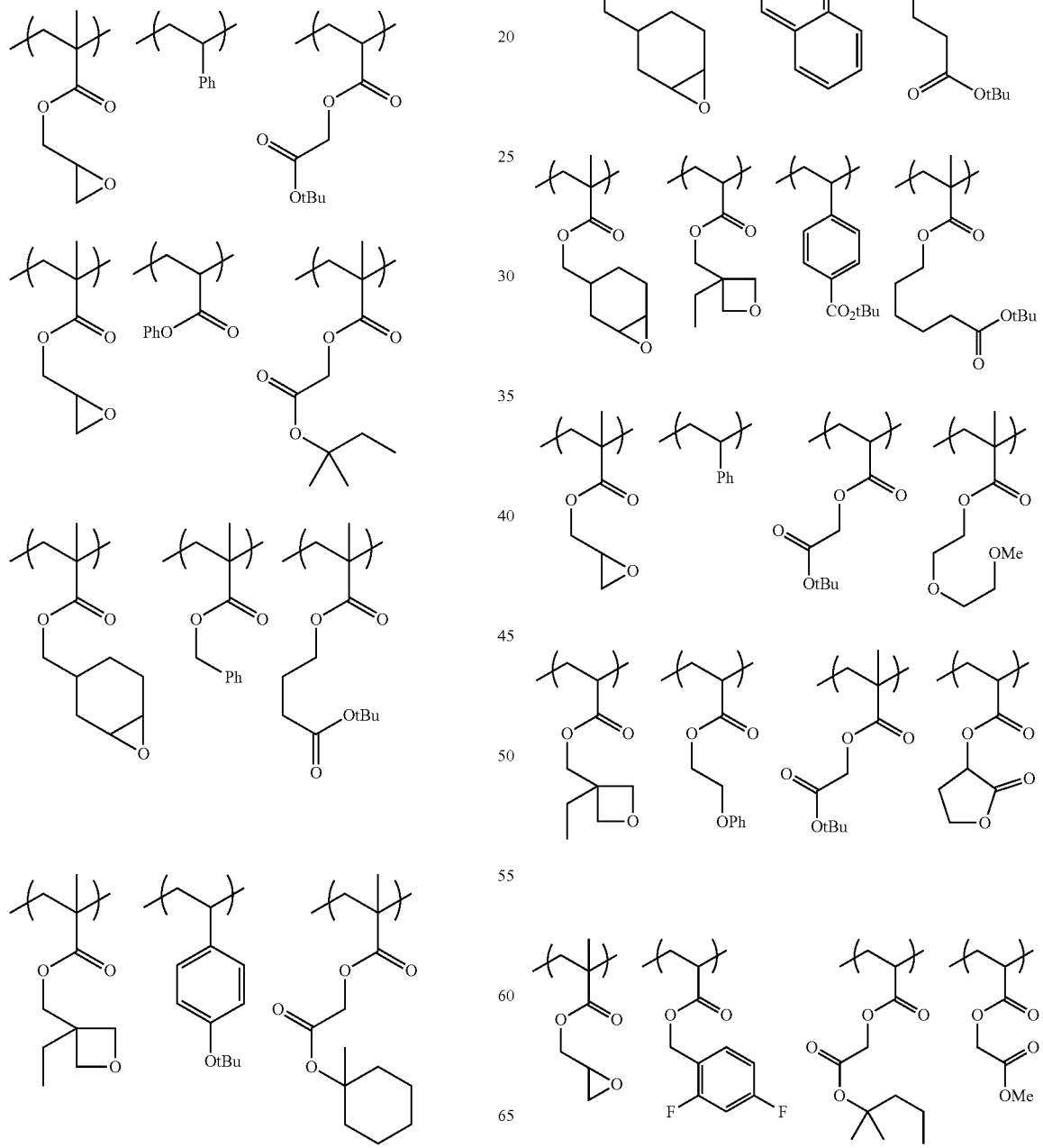

-continued
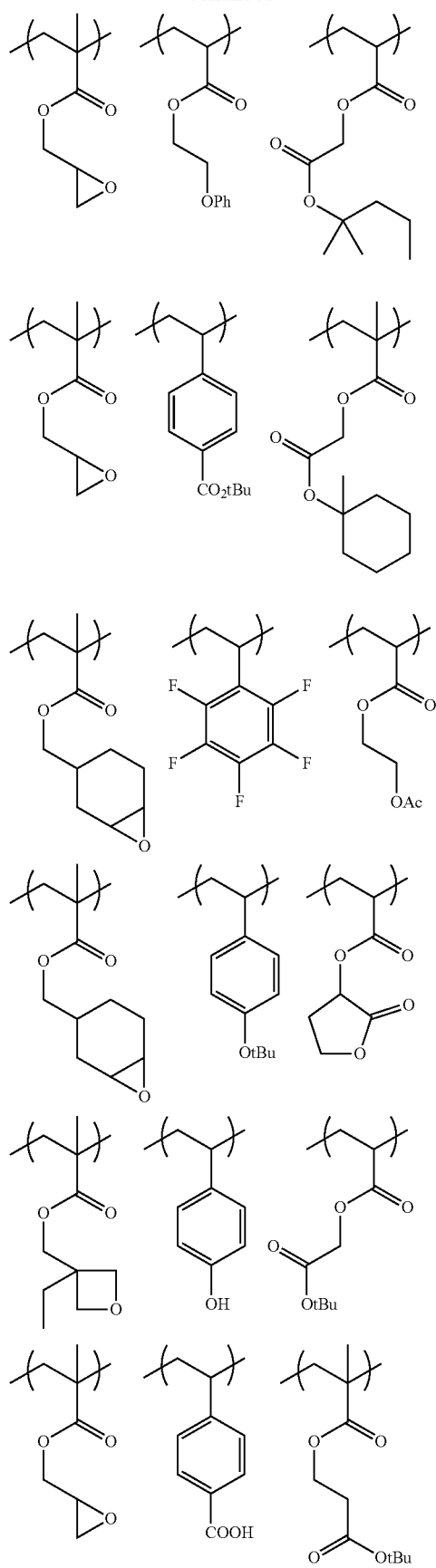
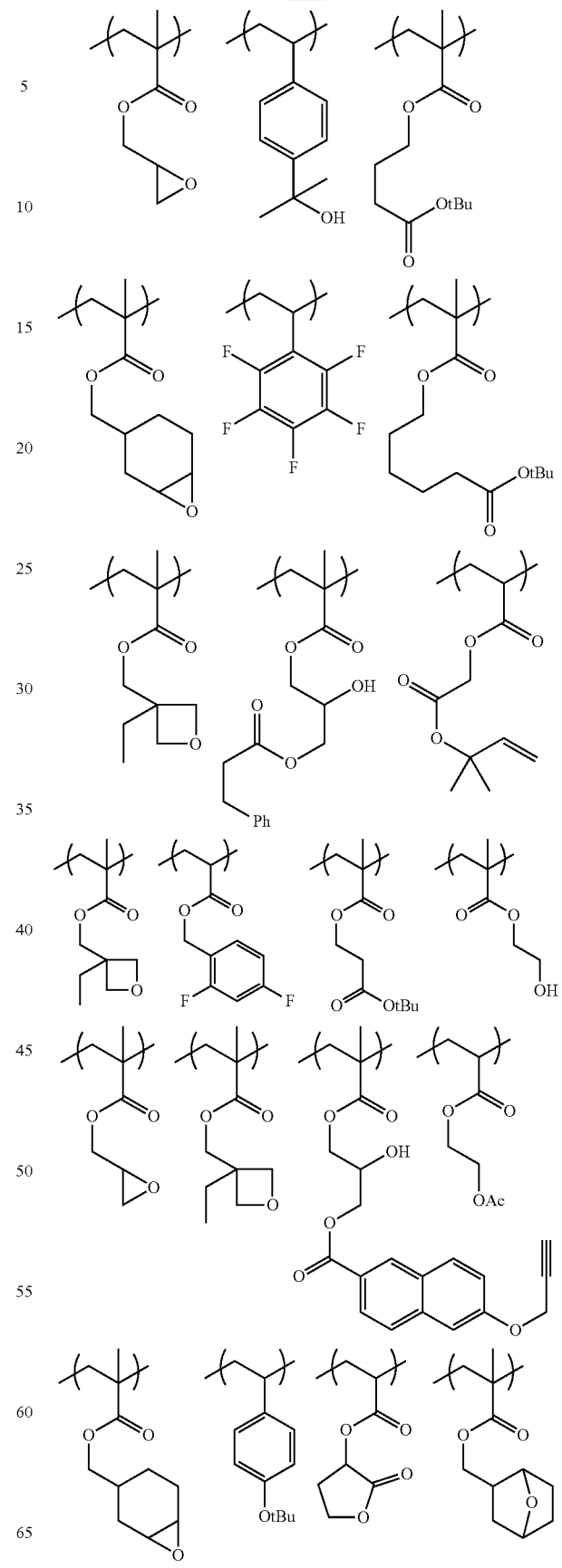

-continued
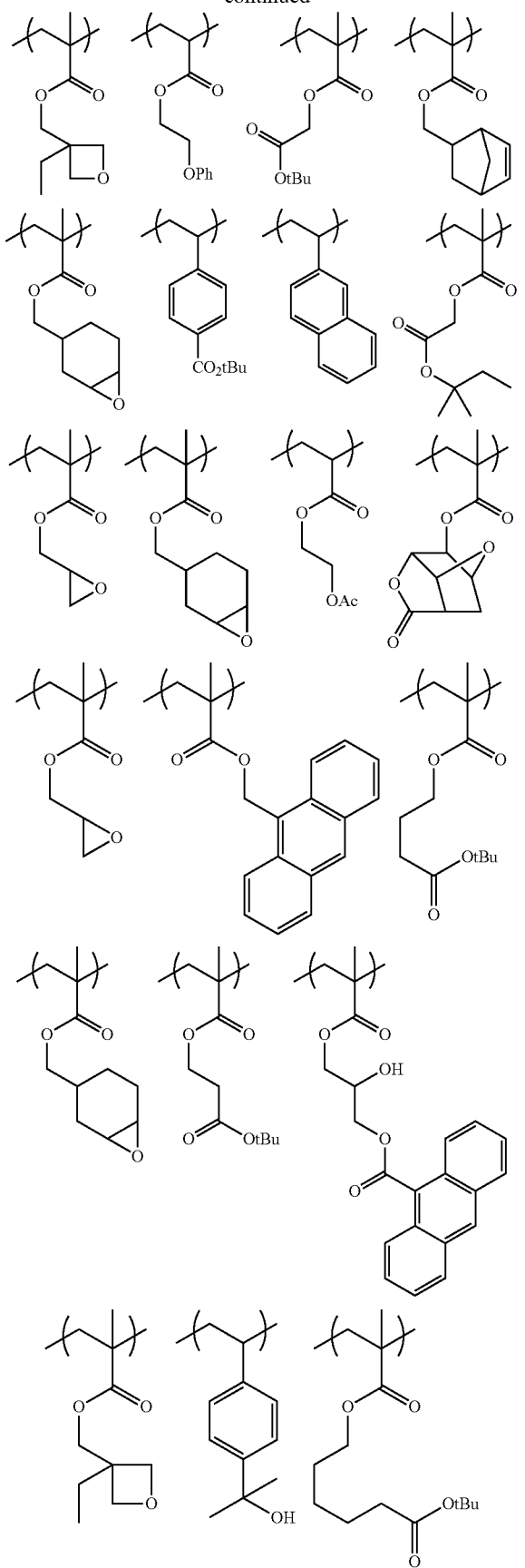
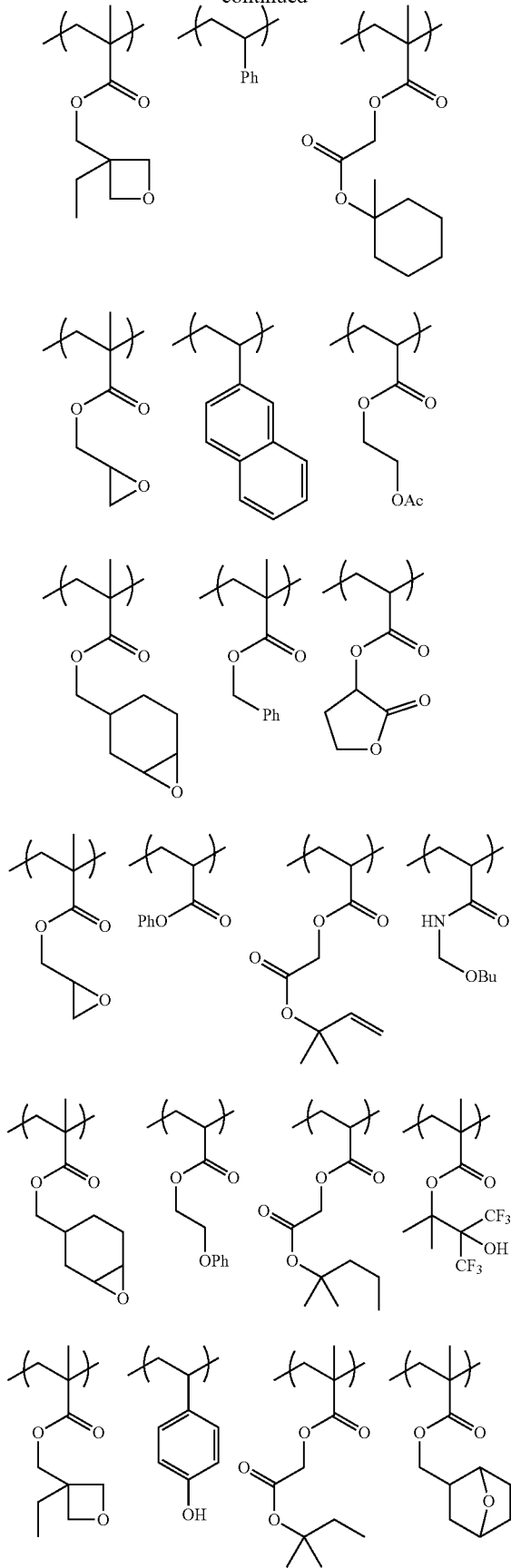

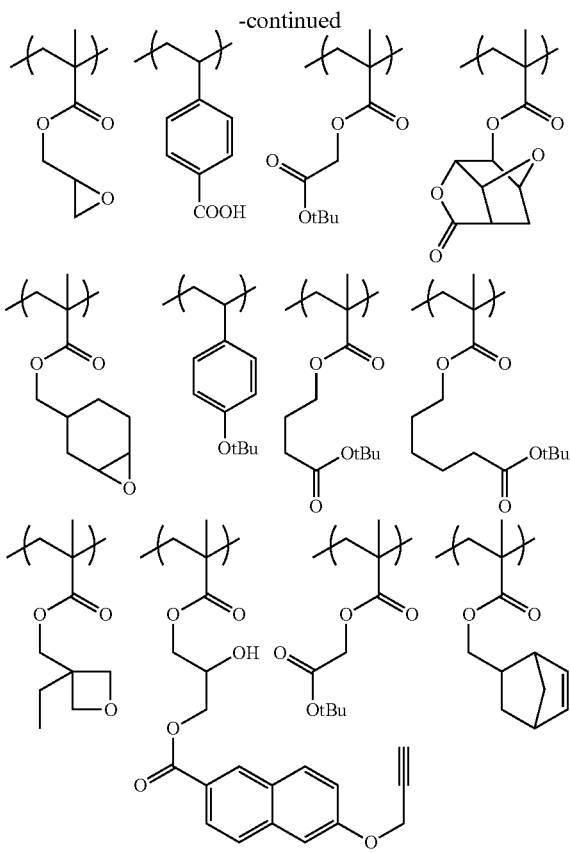

-continued

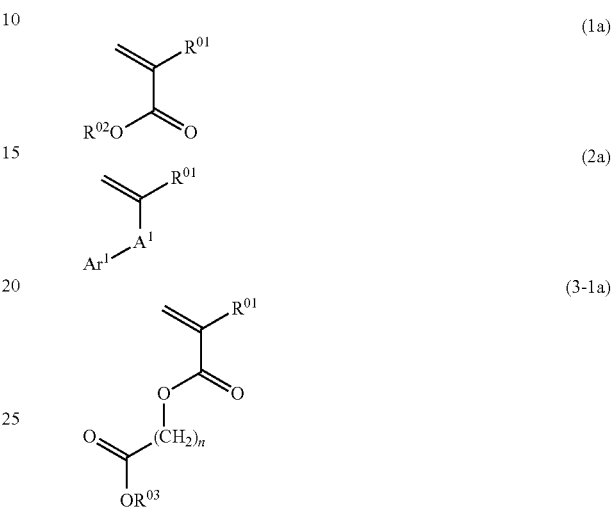

In the present invention, the polymer (1A) may be used singly or as a mixture of two or more of them. Alternatively, the polymer (1A) may be used as a mixture with a resin not containing the repeating units represented by the general formulae (1), (2), and (3). In this case, the resin allowed to be mixed therewith is not particularly restricted, so that heretofore known resins may be used. However, specifically an acrylic resin, a styrenic resin, a phenol resin, a polyether resin, and an epoxy resin are preferable.

Meanwhile, for synthesis of the polymer (1A), one method thereof is the way in which monomers having polymerizable unsaturated bonds corresponding to the respective repeating units are mixed, and then a thermal polymerization of the mixture is carried out in a solvent by addition of a radical polymerization initiator so as to obtain the polymer. The polymerization condition can be arbitrarily chosen in accordance with the monomers to be used, a target molecular weight, and so forth, so that the condition is not particularly restricted, while specific example of the solvent to be used in the polymerization includes toluene, benzene, tetrahydrofuran, diethyl ether, dioxane, 2-butanone, methyl isobutyl ketone, propylene glycol monomethyl ether acetate, cyclohexanone, γ-butyrolactone, ethyl acetate, and butyl acetate. Illustrative example of the polymerization initiator includes 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. As a chain transfer agent, a thiol such as octanethiol or 2-mercaptoethanol may be added at the time of polymerization. The polymerization reaction may be carried out by heating in the temperature range of preferably 40° C. to a boiling point of the reaction solvent. The reaction time is in the range of 0.5 to 100 hours, while preferably in the range of 1 to 48 hours.

For example, when the polymerization as mentioned above is carried out by using as the monomers the compounds having the polymerizable double bond represented by the following general formulae (1a), (2a), and (3-1a), the polymer (polymer compound) containing the repeating units represented by the general formulae (1), (2), and (3-1) can be synthesized, wherein in the general formulae (1a), (2a), and (3-1a), $R^{01}$, $R^{02}$, $R^{03}$, $A^1$, $Ar^1$, and n represent the same as before.

The polymerization may be carried out in such a way that heating is carried out after all the raw materials are mixed, or alternatively, after part of the raw materials is heated in advance, and then, the rest of the raw materials is separately added or mixed, all at once or gradually. For example, the polymerization method in which only the polymerization solvent is heated, and then into it, a monomer solution and an initiator solution are separately and gradually added may be employed. This method not only can give a relatively homogeneous polymer but also can avoid an abnormal reaction such as a runway reaction; and thus, this method is especially preferable.

The polymerization solution thus obtained may be blended into the resist underlayer film composition as it is, or alternatively, the polymer may be purified by using a usual method such as crystallization, phase separation, filtration, or concentration so as to remove residual monomers, residual solvent, reaction byproducts, and other impurities. When the polymer (1A) is purified, the preferable method for it is a crystallization method in which a poor solvent such as water, a water-containing alcohol, or a saturated hydrocarbon is added into the polymerization solution so as to collect the formed precipitate by filtration, or a phase separation method in which a poor solvent phase is removed by separation; but between them, the phase separation method is especially preferable. When the polymer is purified by the phase separation method, low molecular weight components in the polymerization solution can be efficiently removed, so that the generation of sublimate during the time of forming the resist underlayer film from the resist underlayer film composition that contains the polymer can be suppressed; and thus, this is preferable in view of prevention of fouling of the film-forming equipment.

In addition, the resist underlayer film composition of the present invention may be blended further with other compound or polymer. The compound for blending or the polymer for blending has a role to improve the film-formability by spin coating or the gap-filling characteristic on the substrate having steps when the resist underlayer film composition is mixed with the compound of the (A1) component and the polymer of the (A2) component. With regard to the compound for blending or the polymer for blending, a compound having a phenolic hydroxyl group is preferable.

With regard to the material as mentioned above, following materials may be mentioned; namely, novolak resins of phenol, o-cresol, m-cresol, p-cresol, 2,3-dimethylphenol, 2,5-dimethylphenol, 3,4-dimethylphenol, 3,5-dimethylphenol, 2,4-dimethylphenol, 2,6-dimethylphenol, 2,3,5-trimethylphenol, 3,4,5-trimethylphenol, 2-tert-butylphenol, 3-tert-butylphenol, 4-tert-butylphenol, 2-phenylphenol, 3-phenylphenol, 4-phenylphenol, 3,5-diphenylphenol, 2-naphthylphenol, 3-naphthylphenol, 4-naphthylphenol, 4-tolytylphenol, resorcinol, 2-methylresorcinol, 4-methylresorcinol, 5-methylresorcinol, catechol, 4-tert-butylcatechol, 2-methoxyphenol, 3-methoxyphenol, 2-propylphenol, 3-propylphenol, 4-propylphenol, 2-isopropylphenol, 3-isopropylphenol, 4-isopropylphenol, 2-methoxy-5-methylphenol, 2-tert-butyl-5-methylphenol, pyrogallol, thymol, isothymol, 4,4'-(9H-fluorene-9-ylidene)bisphenol, 2,2'dimethyl-4,4'-(9H-fluorene-9-ylidene)bisphenol, 2,2'diallyl-4,4'-(9H-fluorene-9-ylidene)bisphenol, 2,2'difluoro-4,4'-(9H-fluorene-9-ylidene)bisphenol, 2,2'diphenyl-4,4'-(9H-fluorene-9-ylidene)bisphenol, 2,2'dimethoxy-4,4'-(9H-fluorene-9-ylidene)bisphenol, 2,3,2',3'-tetrahydro-(1,1')-spirobiindene-6,6'-diol, 3,3,3',3'-tetramethyl-2,3,2',3'-tetrahydro-(1,1')-spirobiindene-6,6'-diol, 3,3,3',3',4,4'-hexamethyl-2,3,2',3'-tetrahydro-(1,1')-spirobiindene-6,6'-diol, 2,3,2',3'-tetrahydro-(1,1')-spirobiindene-5,5'-diol, 5,5'-dimethyl-3,3,3',3'-tetramethyl-2,3,2',3'-tetrahydro-(1,1')-spirobiindene-6,6'-diol, 1-naphthol, 2-naphthol, 2-methyl-1-naphthol, 4-methoxy-1-naphthol, 7-methoxy-2-naphthol, dihydroxy naphthalenes such as 1,5-dihydroxynaphthalene, 1,7-dihydroxynaphthalene, and 2,6-dihydroxynaphthalene, methyl 3-hydroxynaphthalene-2-carboxylate, indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, 5-vinylnoroborna-2-ene, α-pinene, β-pinene, and limonene; polyhydroxystyrene, polystyrene, polyvinyl naphthalene, polyvinyl anthracene, polyvinyl carbazole, polyindene, polyacenaphthylene, polynorbornene, polycyclodecene, polytetracyclododecene, polynortricyclene, poly(meth)acrylate, and their copolymers. Further, naphthol-dicyclopentadiene copolymer described in Japanese Patent Laid-Open Publication No. 2004-205685, a fluorene bisphenol novolak resin described in Japanese Patent Laid-Open Publication No. 2005-128509, an acenaphthylene copolymer described in Japanese Patent Laid-Open Publication No. 2005-250434, a fullerene containing a phenol group described in Japanese Patent Laid-Open Publication No. 2006-227391, a bisphenol compound and a novolak resin thereof described in Japanese Patent Laid-Open Publication No. 2006-293298, a novolak resin of an adamantane phenol compound described in Japanese Patent Laid-Open Publication No. 2006-285095, a bisnaphthol compound and a novolak resin thereof described in Japanese Patent Laid-Open Publication No. 2010-122656, a fullerene resin compound described in Japanese Patent Laid-Open Publication No. 2008-158002, or the like may also be blended.

Also, a phenol compound represented by the following general formula (2A) or (3A) may be blended. However, the phenol compounds represented by the following general formula (2A) or (3A) do not have the 3,4-dihydroxy phenyl group in the molecule thereof and are different from the compounds represented by the general formula (X),

$$R-(X')_{m2} \tag{2A}$$

wherein R represents a single bond or an organic group having 1 to 50 carbon atoms; X' represents a group represented by the following general formula (2B); and m2 represents an integer satisfying $1 \leq m2 \leq 5$,

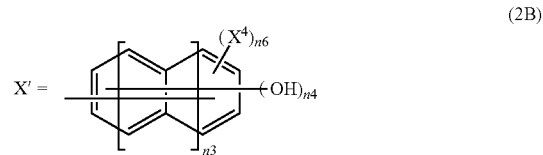

wherein n3 represents 0 or 1; "n4" represents 1 or 2; $X^4$ represents a group represented by following general formula (2C); and "n6" represents 0, 1, or 2,

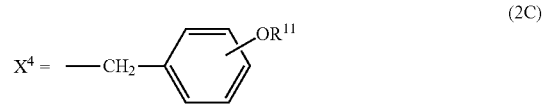

wherein $R^{11}$ represents a hydrogen atom or a saturated or unsaturated hydrocarbon group having 1 to 10 carbon atoms, and the hydrogen atom on the benzene ring in the formula may be optionally substituted by a methyl group or a methoxy group,

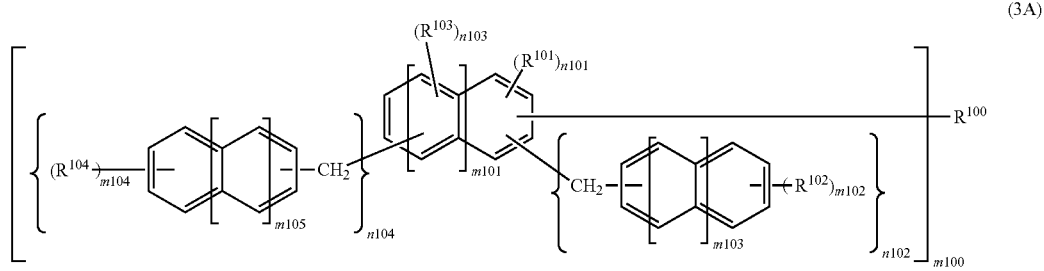

wherein $R^{101}$, $R^{102}$, $R^{103}$, and $R^{104}$ each represents independently a hydrogen atom or a hydroxyl group; m100 represent 1, 2, or 3; $R^{100}$ represents a hydrogen atom or a hydroxyl group when m100 is 1, or a single bond or a group represented by following general formula (3B) when "m100" is 2, or a group represented by following general formula (3C) when "m100" is 3, and the hydrogen atom on the benzene ring in the formula may be optionally substituted by a methyl group, a methoxy group, a hydroxymethyl group, or a methoxymethyl group; "m101" represents 0 or 1, "m102" represents 1 or 2, "m103" represents 0 or 1, "m104" represents 1 or 2, and "m105" represents 0 or 1; when "m101" is 0, "n101" and "n102" represent an integer satisfying $0 \leq n101 \leq 3$, $0 \leq n101 \leq 3$, $0 \leq n102 \leq 3$, and $1 \leq n101+n102 \leq 4$; when "m101" is 1, "n101", "n102", "n103", and "n104" represent an integer satisfying $0 \leq n101 \leq 2$, $0 \leq n102 \leq 2$, $0 \leq n103 \leq 2$, $0 \leq n104 \leq 2$, and $2 \leq n101+n102+n103+n104 \leq 8$;

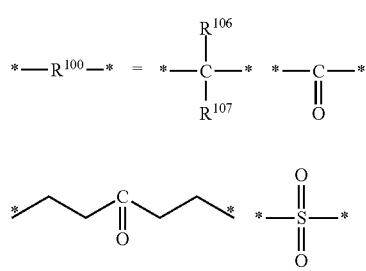

(3B)

wherein "*" represents a bonding site; $R^{106}$ and $R^{107}$ represent a hydrogen atom or an organic group having 1 to 24 carbon atoms; and $R^{106}$ and $R^{107}$ may be bonded to form a ring structure,

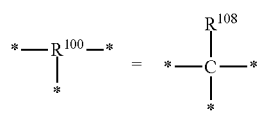

(3C)

wherein "*" represents a bonding site; and $R^{108}$ represents a hydrogen atom or an organic group having 1 to 15 carbon atoms.

Illustrative example of the phenol compound represented by the general formula (2A) and the phenol compound represented by the general formula (3A) includes the compounds described below. Meanwhile, an arbitrary hydrogen atom on the aromatic ring of the following compounds may be optionally substituted by a methyl group, a methoxy group, a hydroxymethyl group, or a methoxymethyl group,

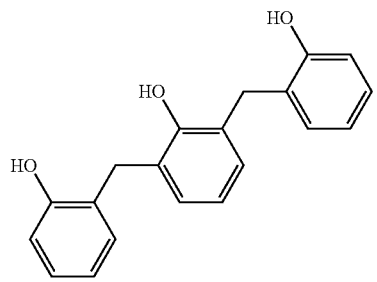

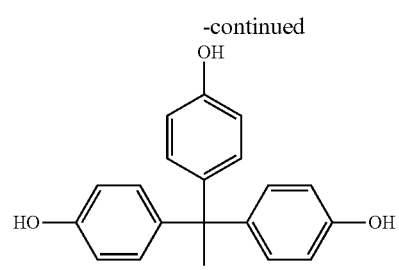

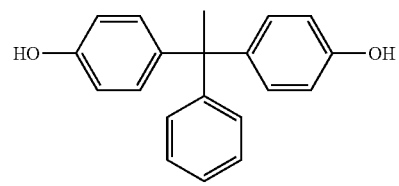

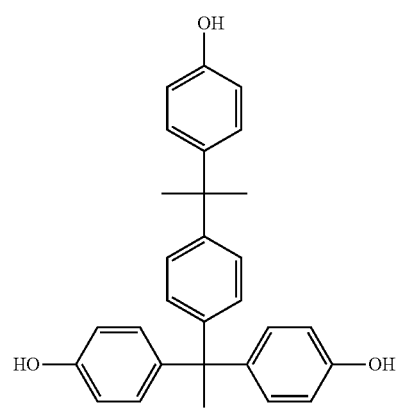

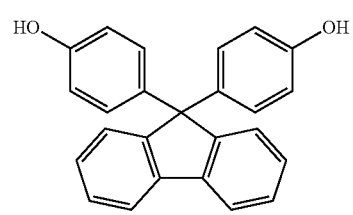

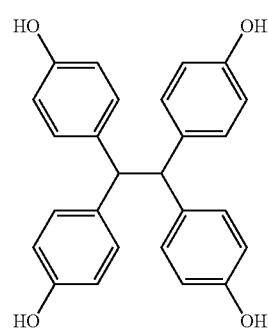

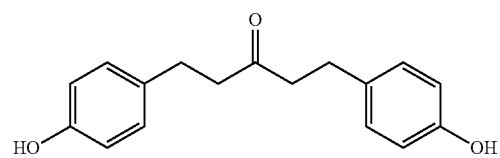

-continued
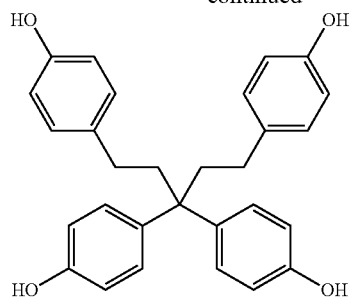
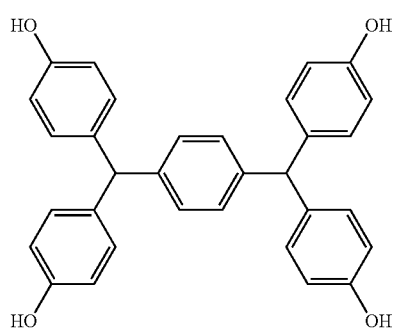
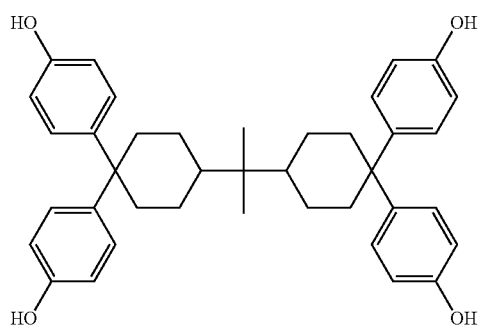
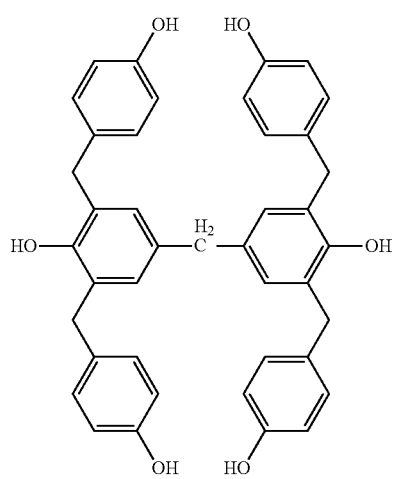
-continued
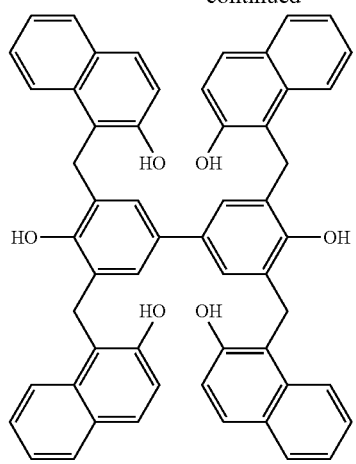
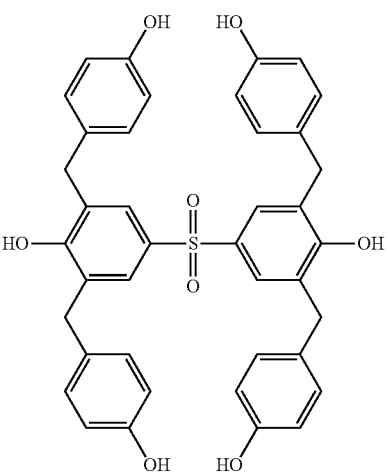
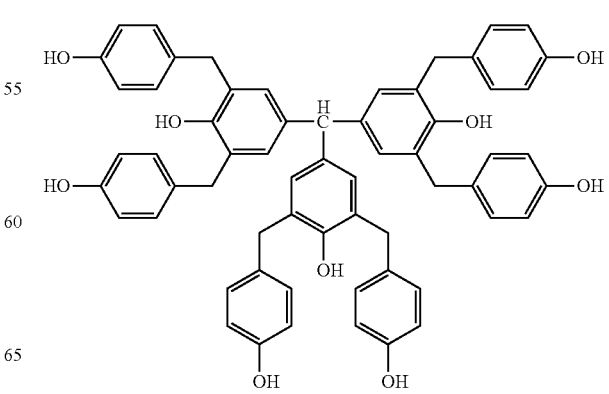

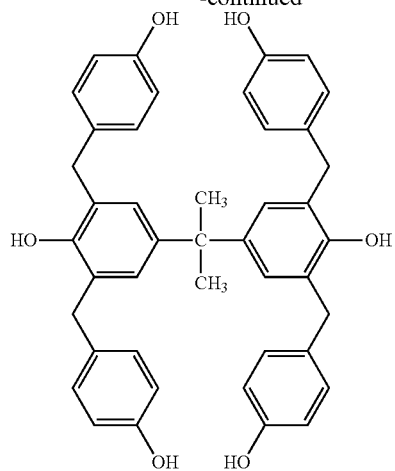
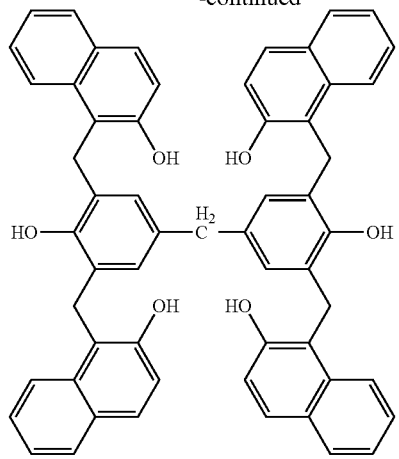
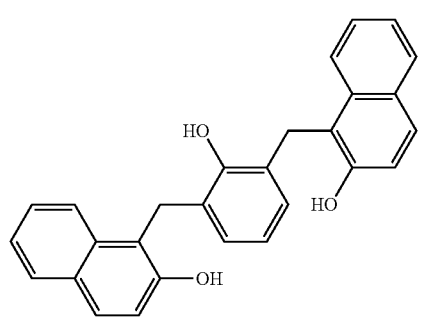
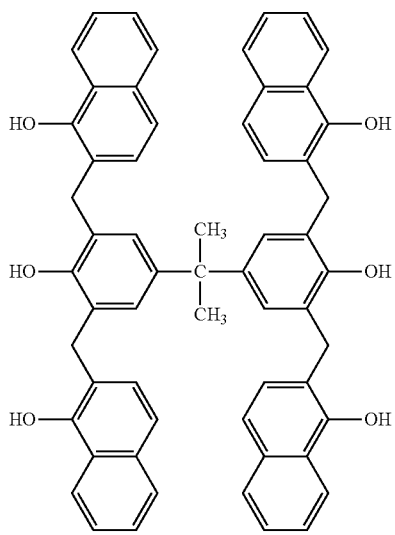
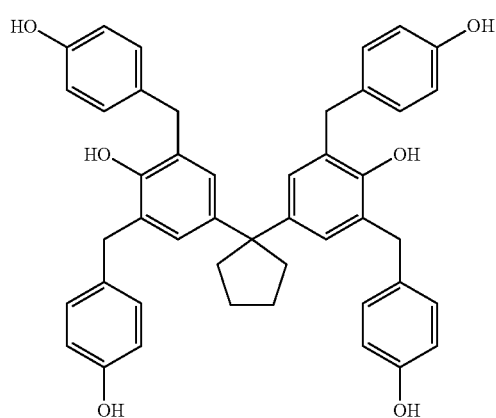
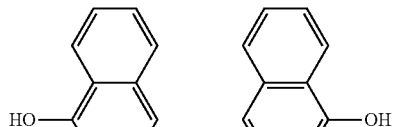
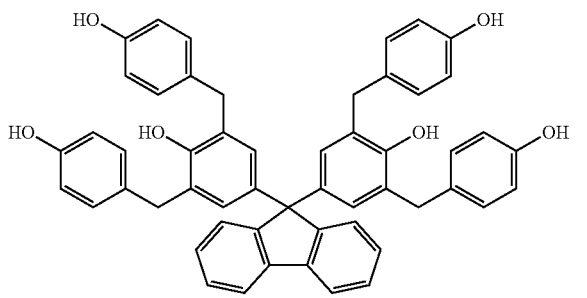
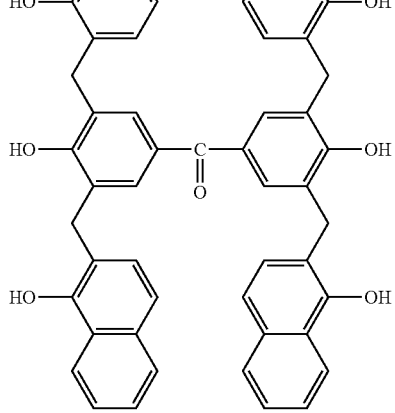

-continued
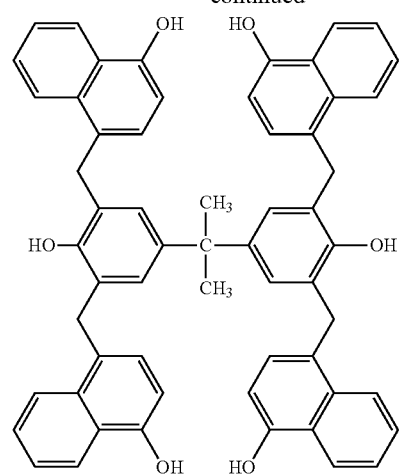
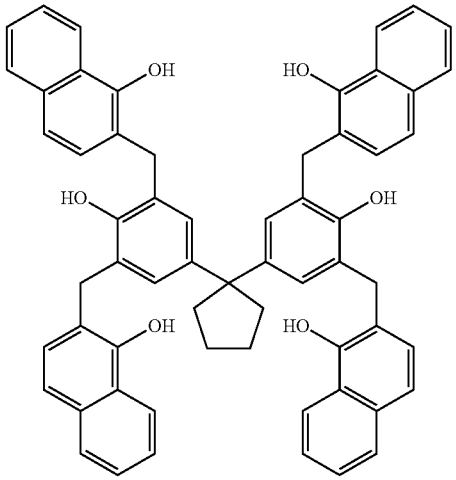
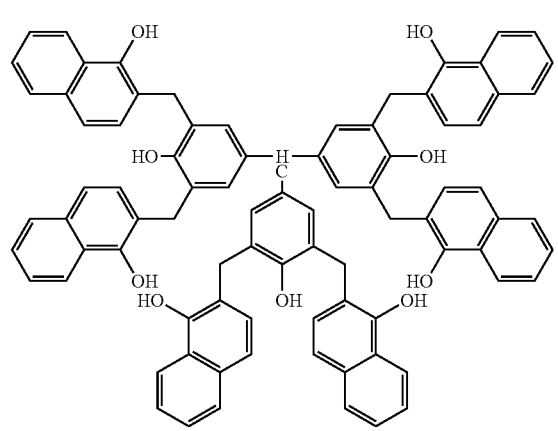
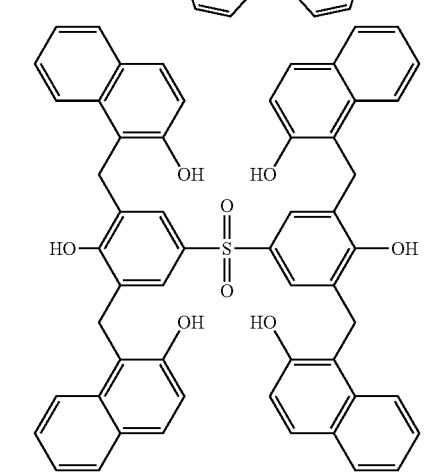
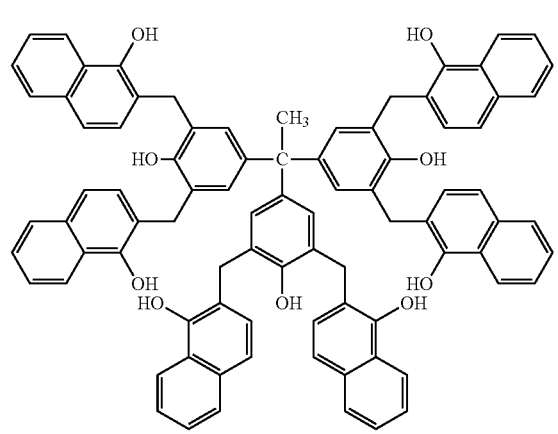
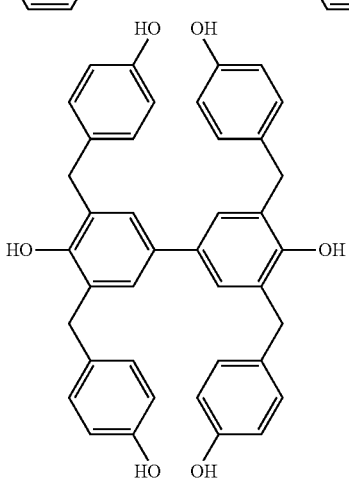

55
-continued
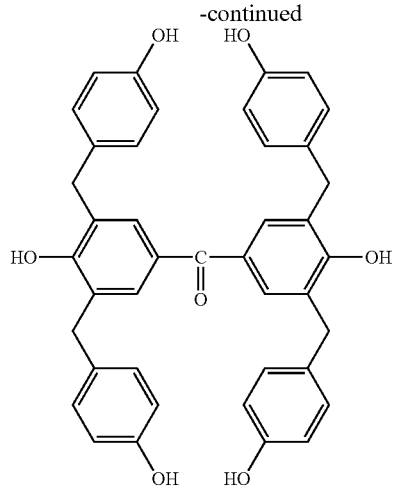
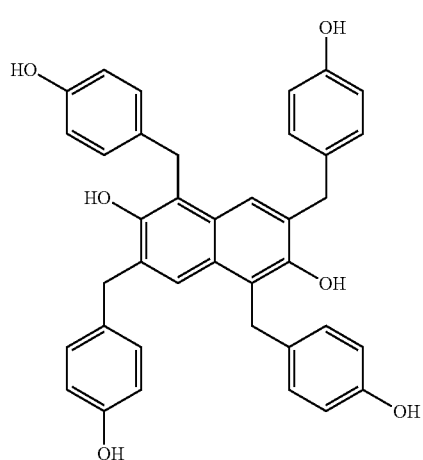
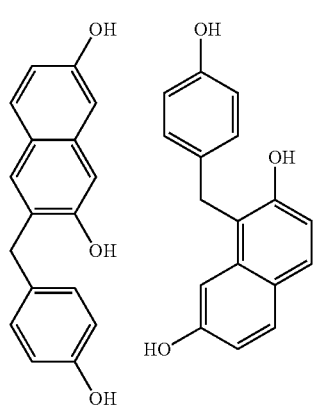
56
-continued
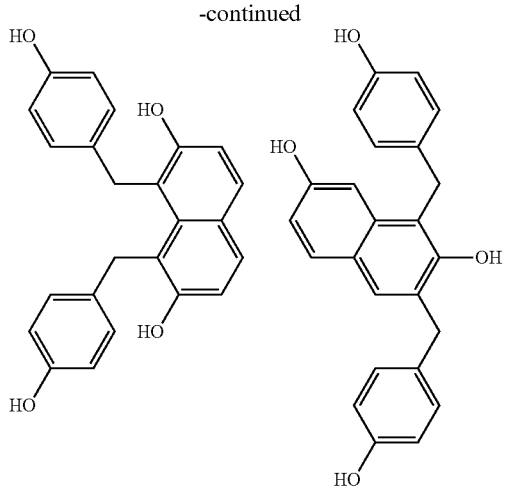
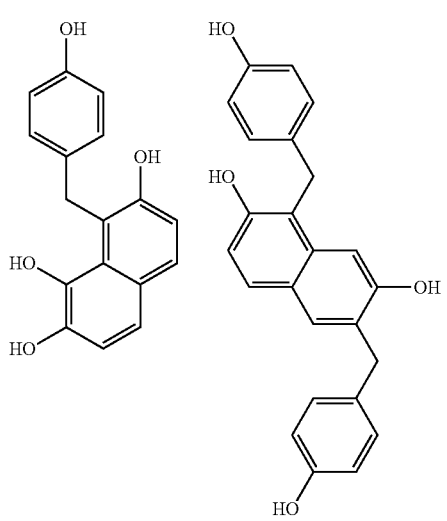
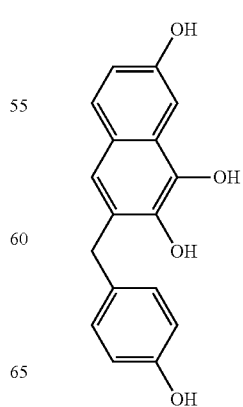

57
-continued
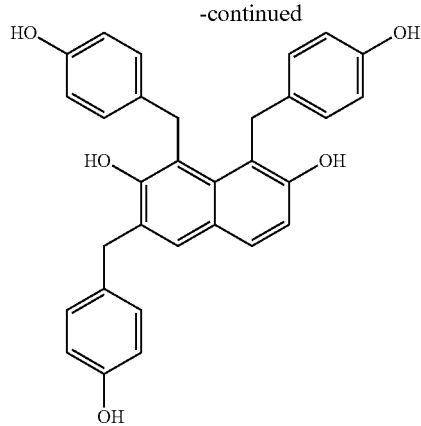
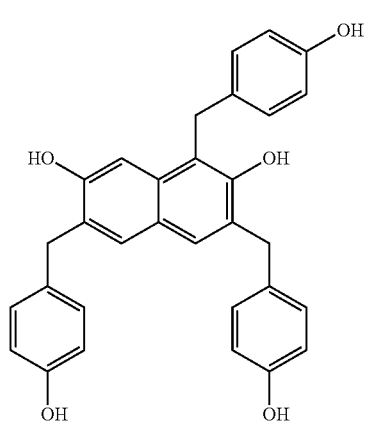
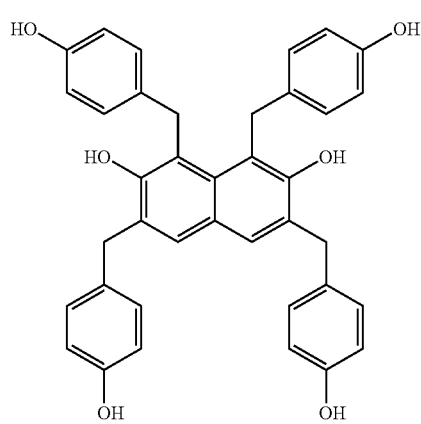
58
-continued
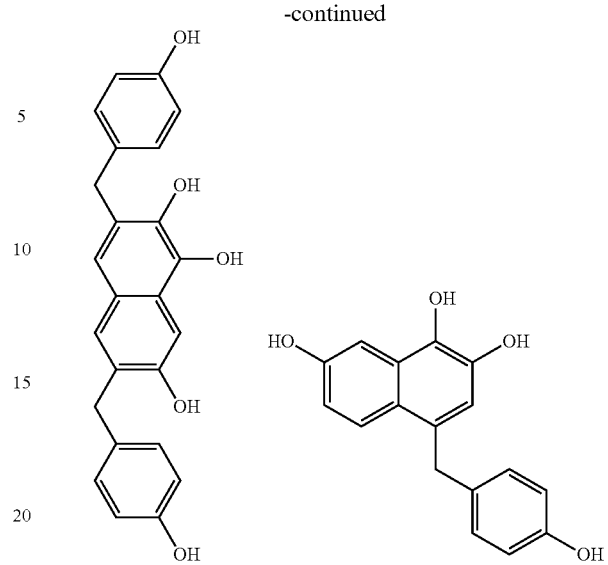
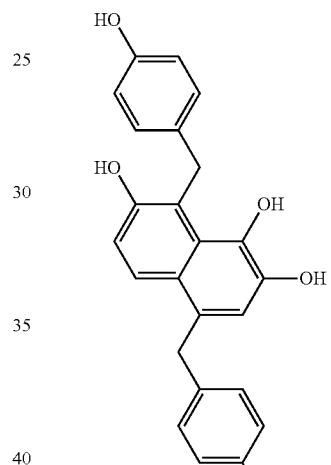
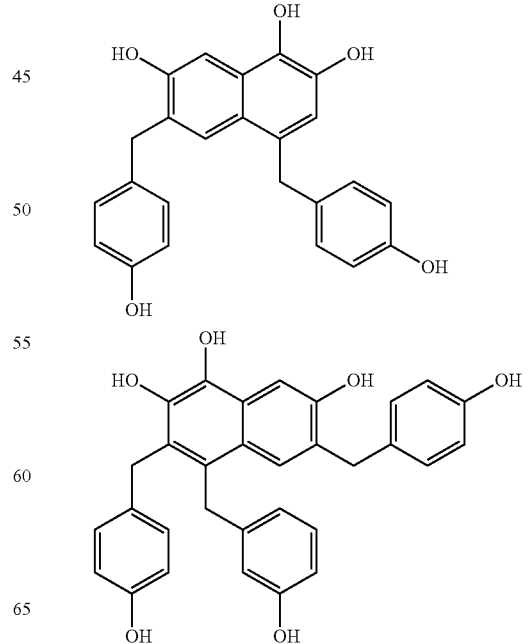

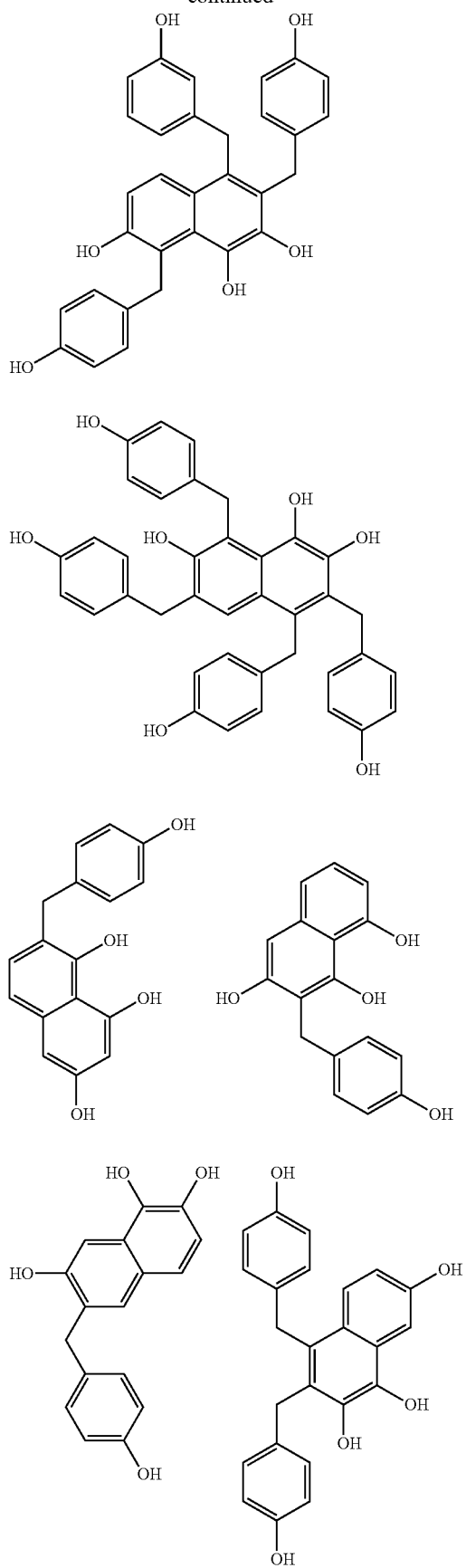
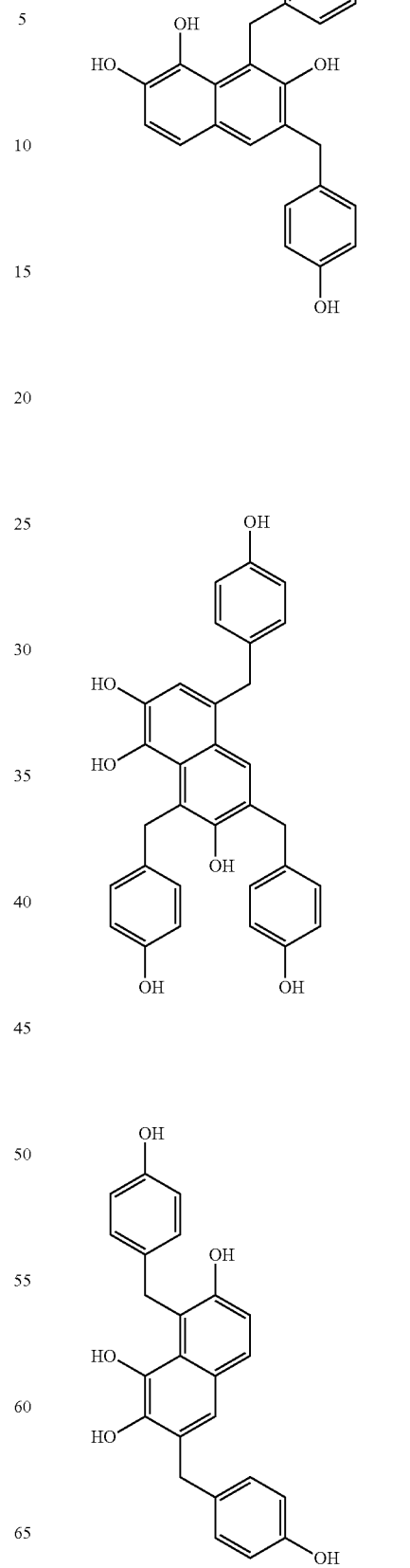

61
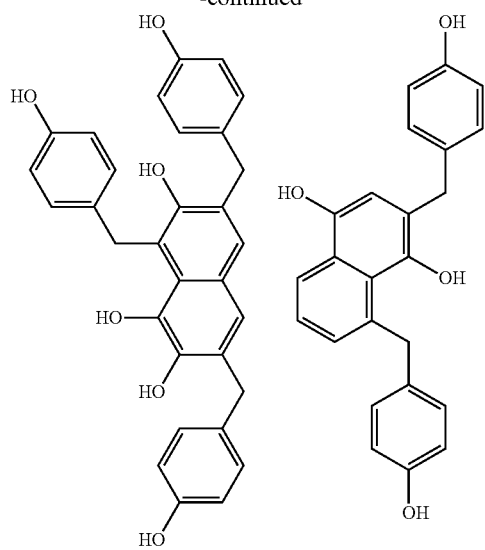
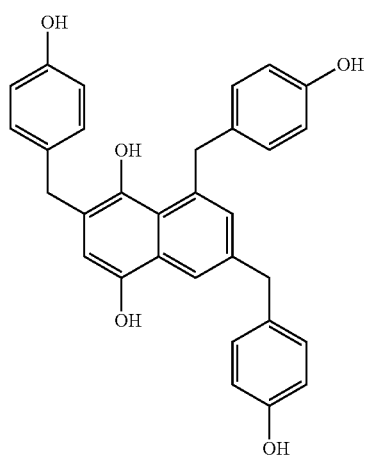
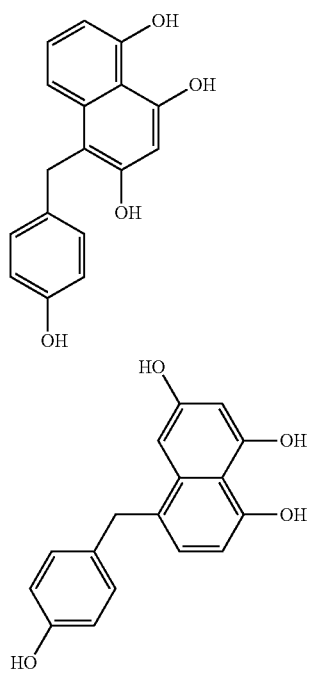
62
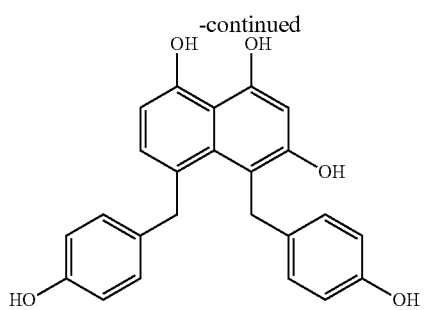
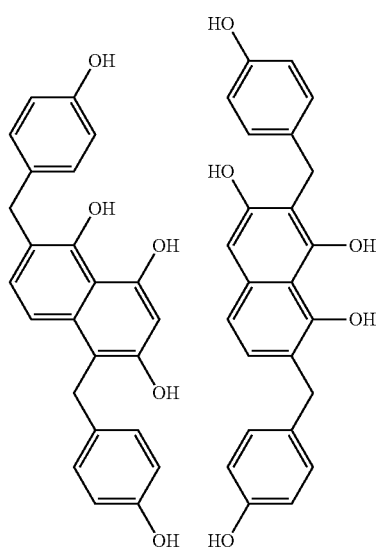
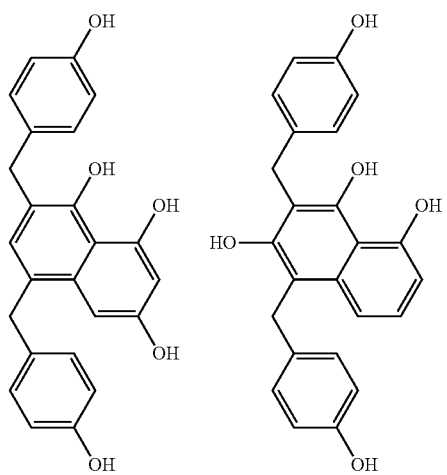

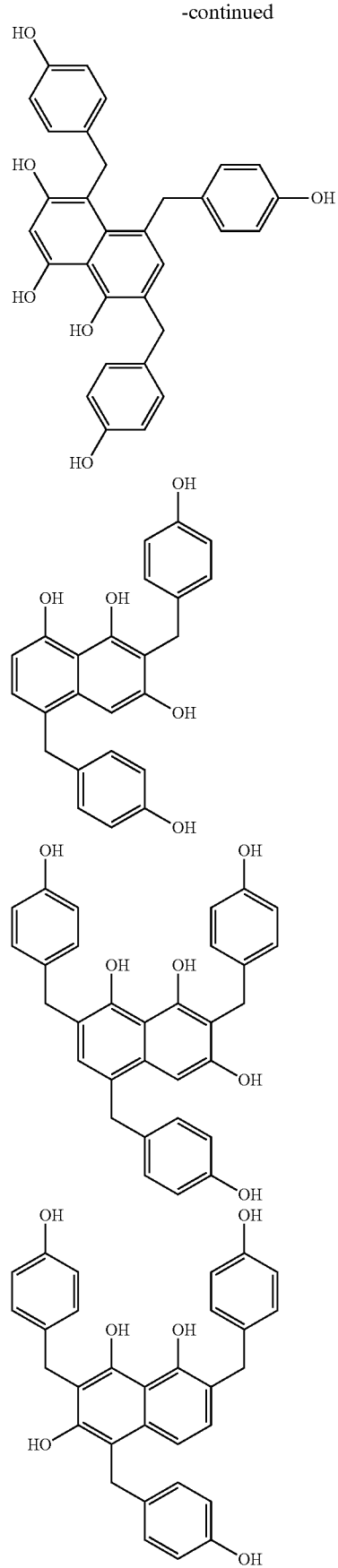
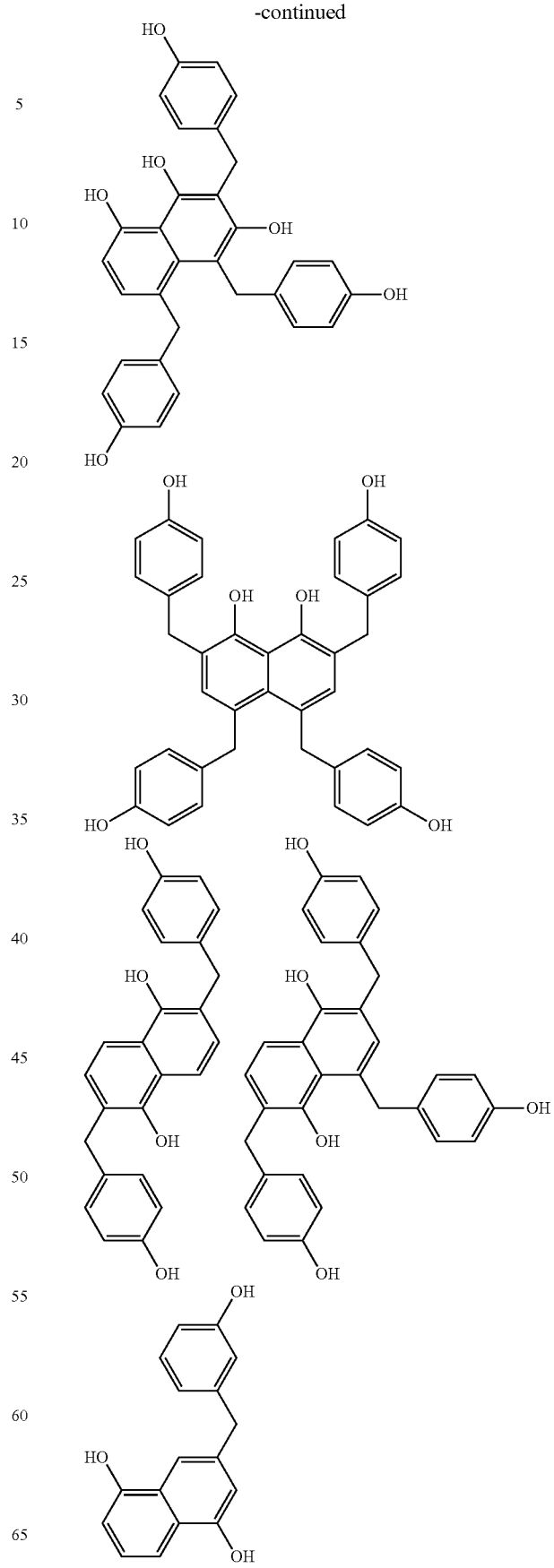

65
-continued
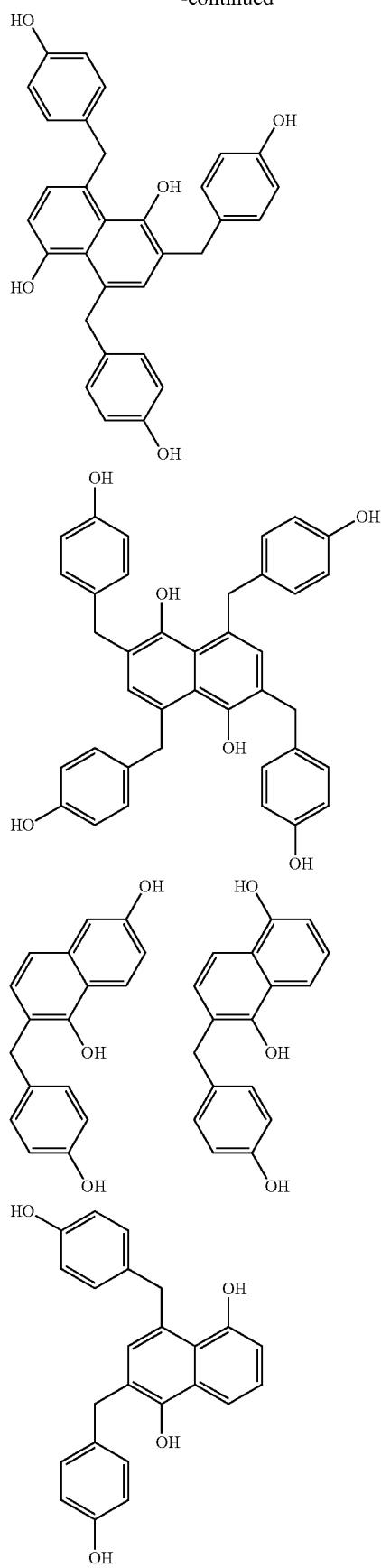
66
-continued
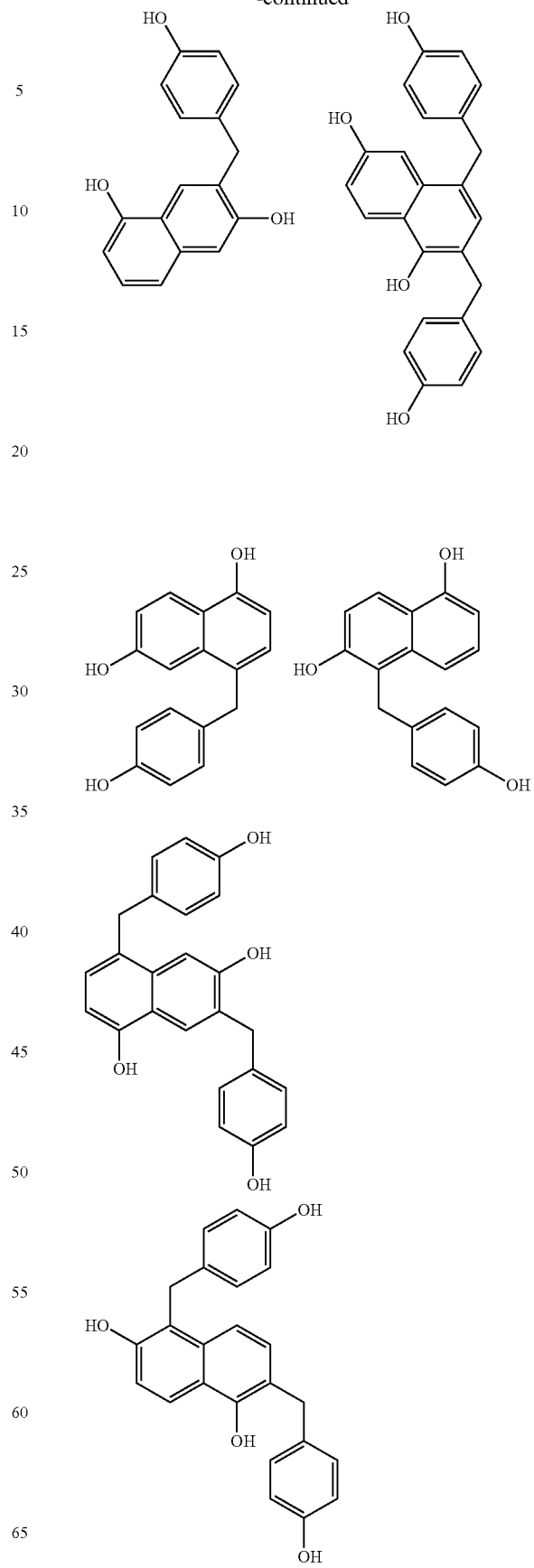

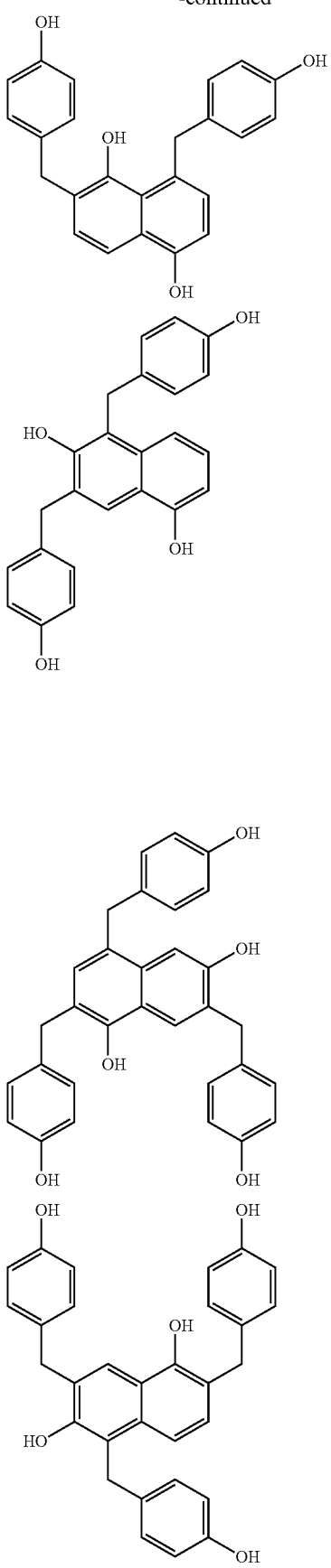
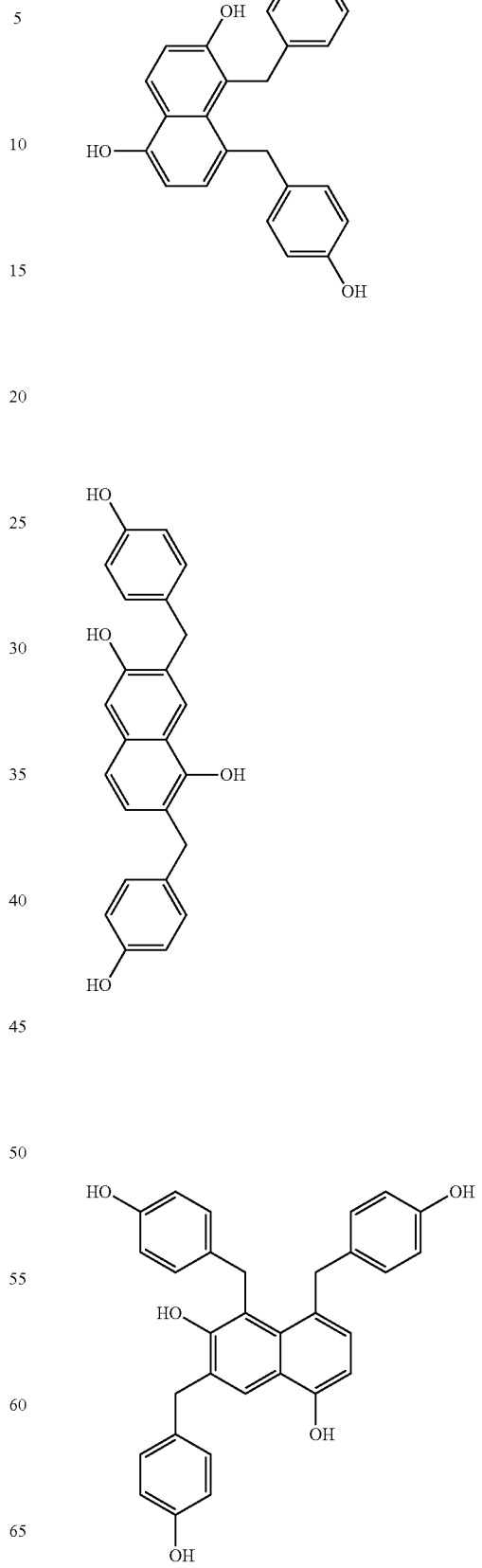

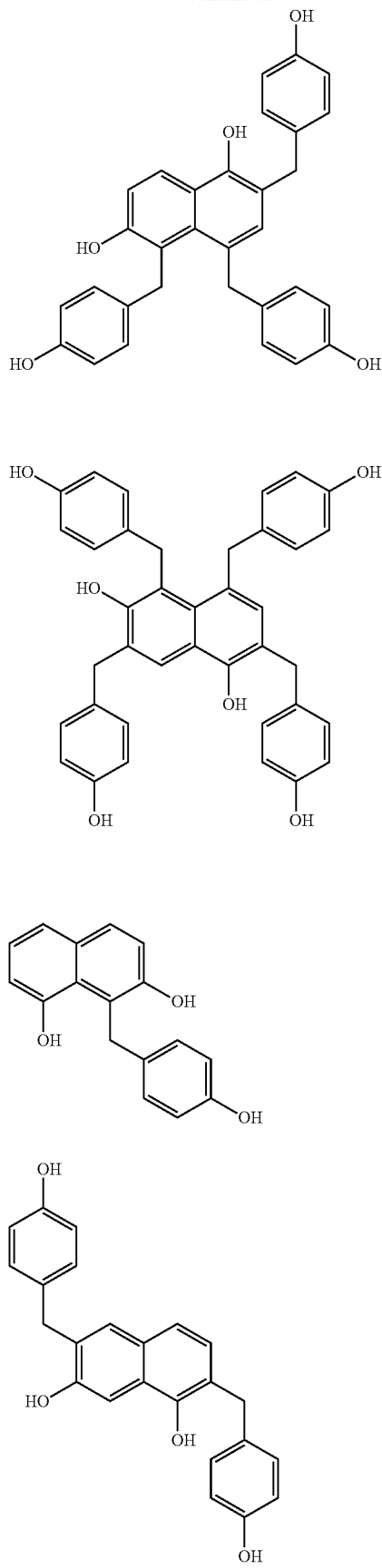
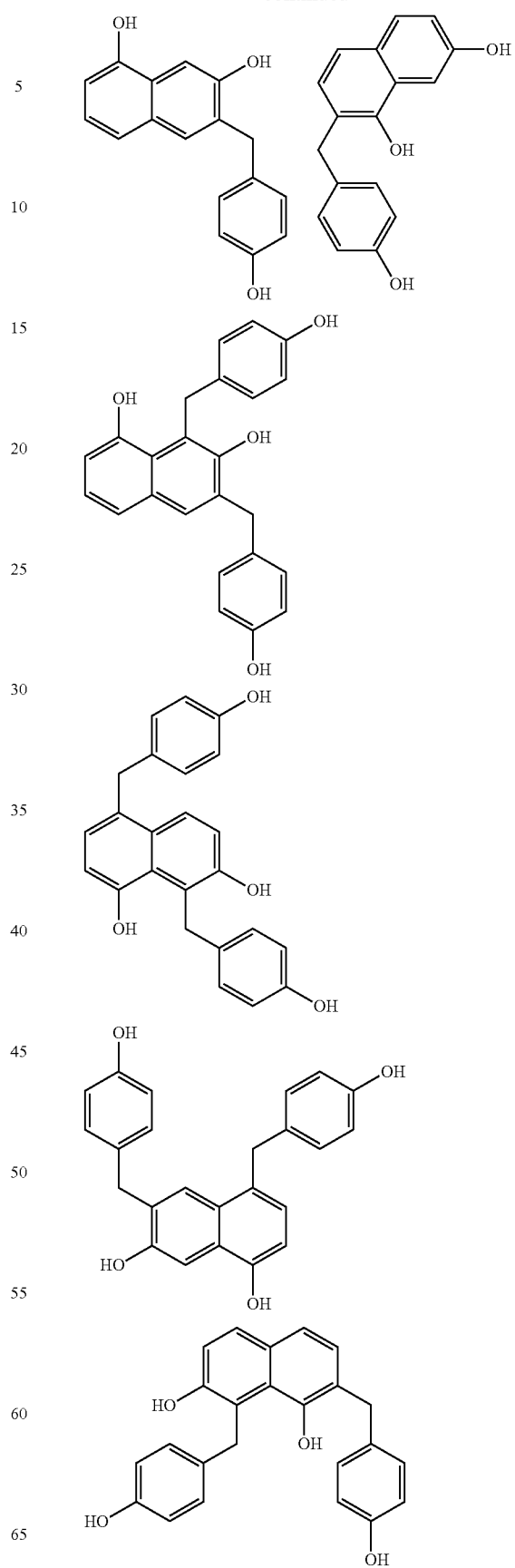

71
-continued
72
-continued
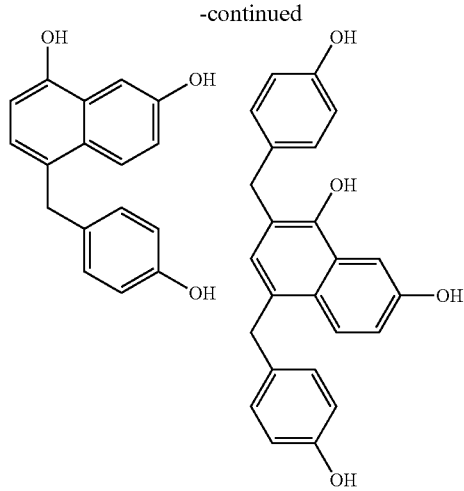
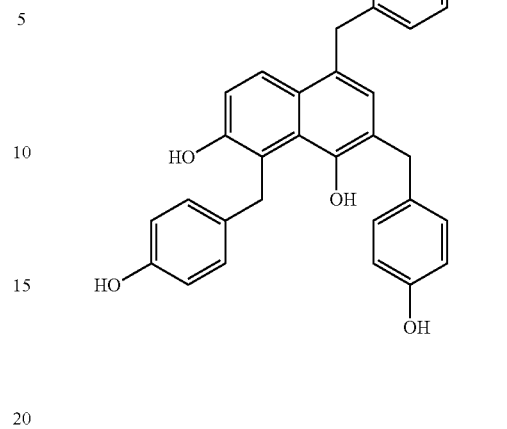
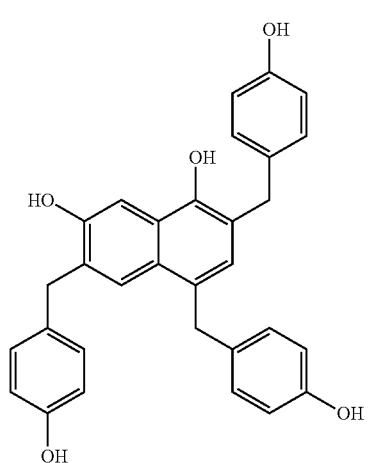
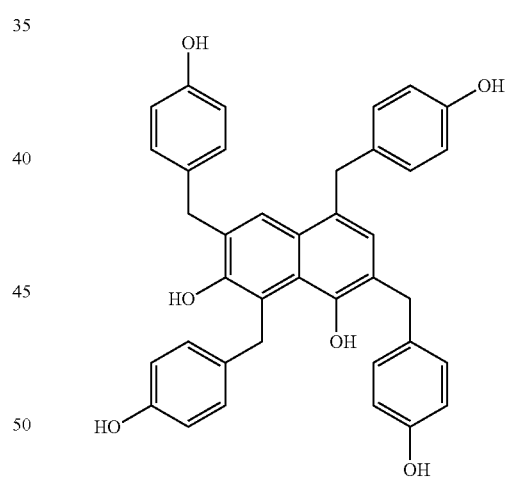
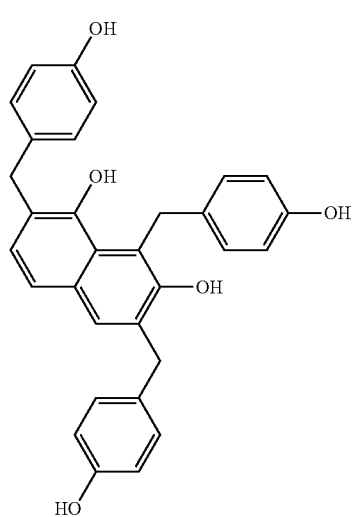
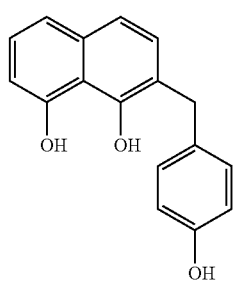 [SMILES: Oc1ccc(Cc2ccc3cccc(O)c3c2O)cc1]

-continued
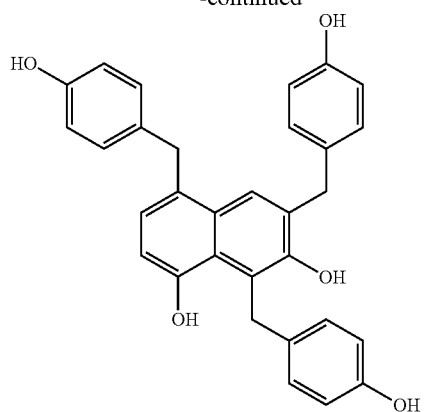
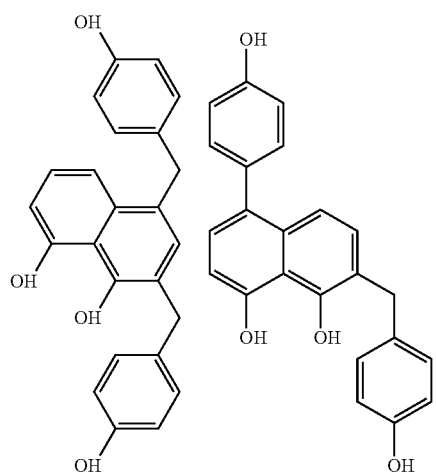
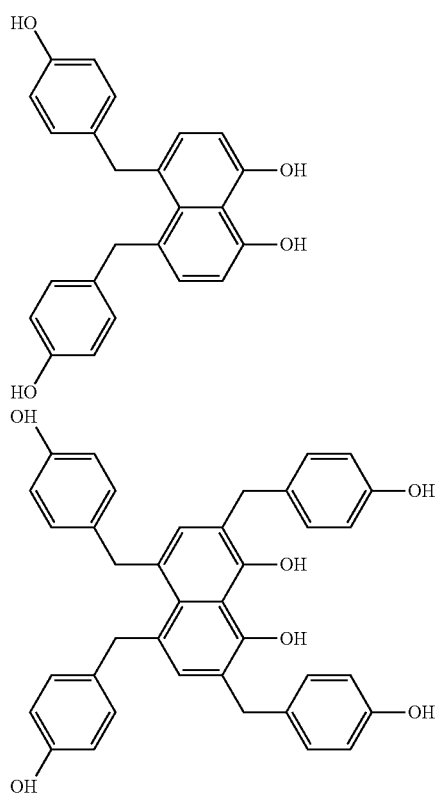
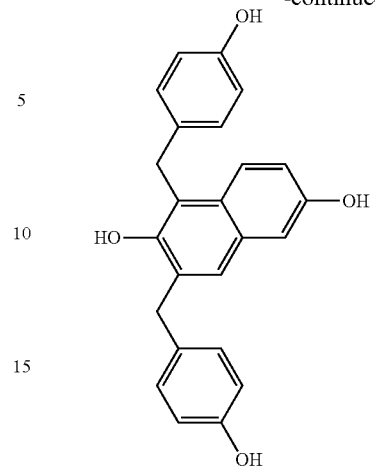
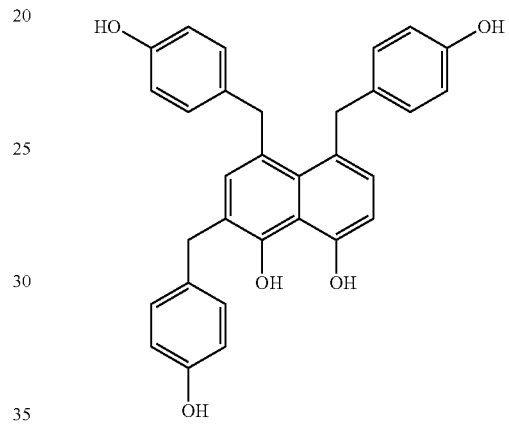
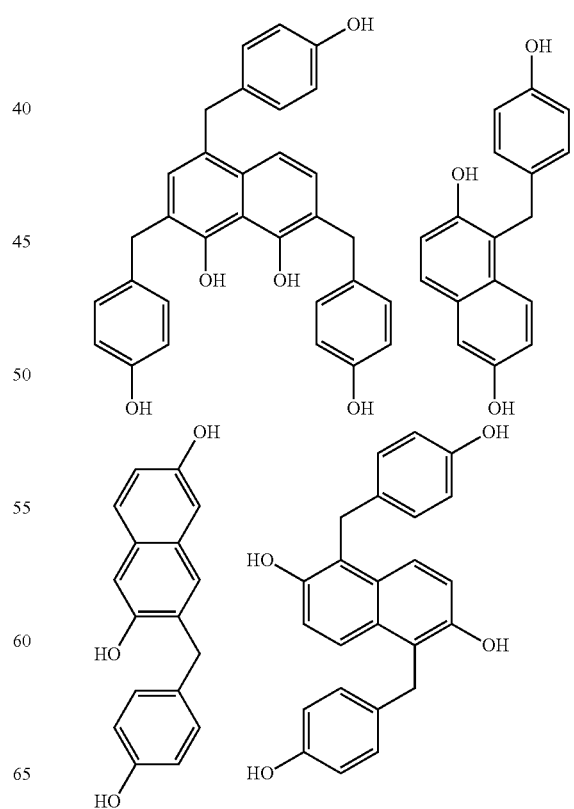

75
-continued
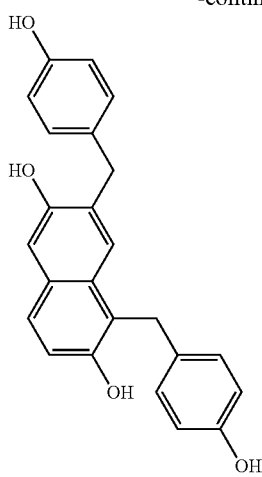
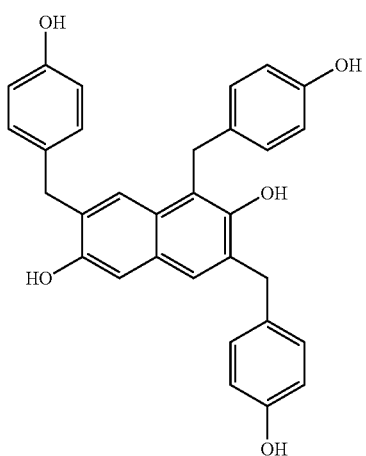
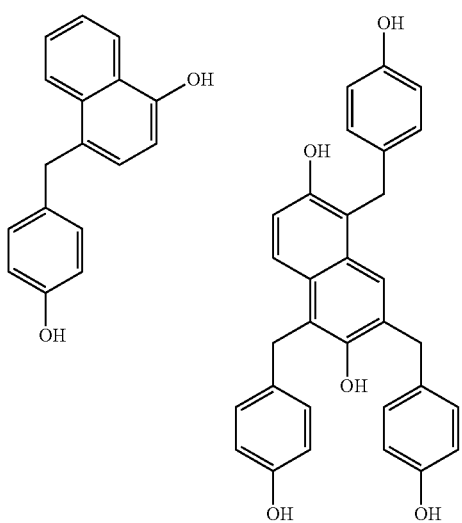
76
-continued
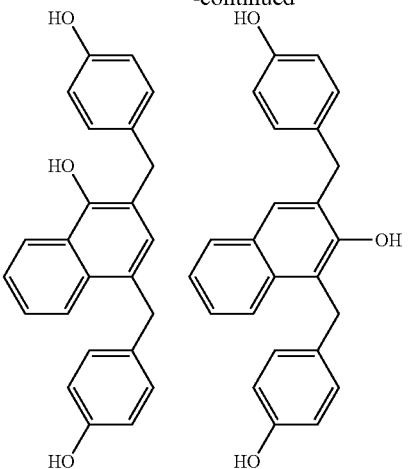
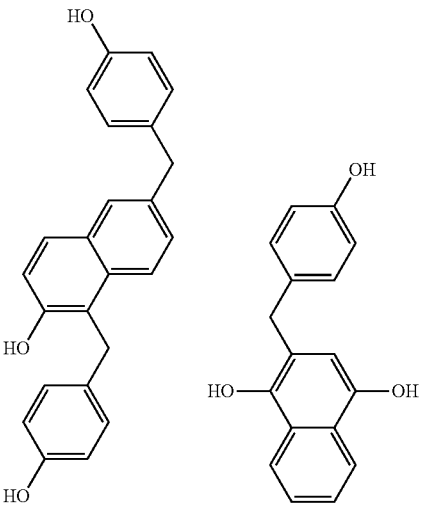
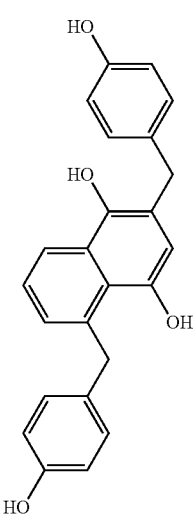

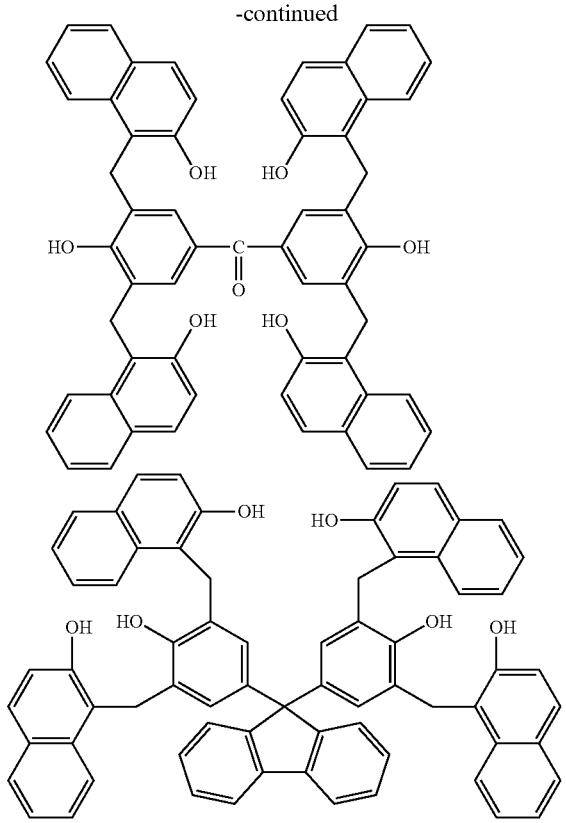

-continued

Blending amount of the compound for blending or of the polymer for blending is preferably in the range of 5 to 250 parts by mass, while more preferably in the range of 5 to 100 parts by mass, relative to 100 parts by mass of the compound of the (A1) component.

[(B) Component]

The (B) component in the resist underlayer film composition of the present invention is an organic solvent. The organic solvent (B) usable in the resist underlayer film composition of the present invention is not particularly restricted so far as it can dissolve the compound of the (A1) component; and in addition, it is preferable that the solvent can also dissolve the polymer (1A) of the (A2) component, (C) an acid generator, (D) a surfactant, (E) a crosslinking agent, (F) a plasticizer, and (G) a pigment, wherein the (C) to (G) additives will be discussed later. Specifically, the solvents described in the paragraphs [0091] to [0092] of Japanese Patent Laid-Open Publication No. 2007-199653 may be added. Among them, preferable solvents are as follows: propylene glycol monomethyl ether acetate, propylene glycol monomethyl ether, propylene glycol monoethyl ether, propylene glycol monopropyl ether, 2-heptanone, cyclopentanone, cyclohexanone, 1-octanol, 2-ethylhexanol, 1-nonanol, 1-decanol, 1-undecanol, ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, tripropylene glycol, glycerin, n-nonyl acetate, monohexyl ether, ethylene glycol mono-2-ethylhexyl ether, ethylene glycol monophenyl ether, ethylene glycol monobenzyl ether, diethylene glycol monoethyl ether, diethylene glycol monoisopropyl ether, diethylene glycol mono-n-butyl ether, diethylene glycol monoisobutyl ether, diethylene glycol monohexyl ether, diethylene glycol monophenyl ether, diethylene glycol monobenzyl ether, diethylene glycol diethyl ether, diethylene glycol dibutyl ether, diethylene glycol butyl methyl ether, triethylene glycol dimethyl ether, triethylene glycol monomethyl ether, triethylene glycol-n-butyl ether, triethylene glycol butyl methyl ether, tetraethylene glycol dimethyl ether, dipropylene glycol monomethyl ether, dipropylene glycol mono-n-propyl ether, dipropylene glycol mono-n-butyl ether, tripropylene glycol dimethyl ether, tripropylene glycol monomethyl ether, tripropylene glycol mono-n-propyl ether, tripropylene glycol mono-n-butyl ether, ethylene glycol monoethyl ether acetate, ethylene glycol monobutyl ether acetate, diethylene glycol monomethyl ether acetate, diethylene glycol monoethyl ether acetate, diethylene glycol monobutyl ether acetate, triacetin, propylene glycol diacetate, dipropylene glycol methyl-n-propyl ether, dipropylene glycol methyl ether acetate, 1,4-butanediol diacetate, 1,3-butylene glycol diacetate, 1,6-hexanediol diacetate, γ-butyrolactone, as well as mixtures of two or more of the above-mentioned solvents. It is preferable that the blending amount of the organic solvent be controlled in accordance with the prescribed film thickness of the resist underlayer film; however, the blending amount thereof is usually in the range of 500 to 10,000 parts by mass, relative to 100 parts by mass of the compound of the (A1) component.

[(C) Component]

The resist underlayer film composition of the present invention may be blended with (C) an acid generator in order to further facilitate a crosslinking reaction by heat or the like. There are acid generators generating an acid by thermal decomposition or by photo irradiation, wherein any of them may be blended.

Illustrative example of the acid generator (C) which can be used in the resist underlayer film composition of the present invention includes following compounds:

i onium salts represented by the following general formulae (P1a-1), (P1a-2), (P1a-3), or (P1b),
ii diazomethane derivatives represented by the following general formula (P2),
iii glyoxime derivatives represented by the following general formula (P3),
iv bissulfone derivatives represented by the following general formula (P4),
v sulfonate esters of N-hydroxyimide compounds represented by the following general formula (P5),
vi β-ketosulfonic acid derivatives,
vii disulfone derivatives,
viii nitrobenzylsulfonate derivatives, and
ix sulfonate ester derivatives,

wherein $R^{101a}$, $R^{101b}$, and $R^{101c}$ represents a linear, branched, or cyclic alkyl group, alkenyl group, oxoalkyl group, or oxoalkenyl group, each having 1 to 12 carbon atoms, an aryl group having 6 to 20 carbon atoms, or an aralkyl or aryl oxoalkyl group having 7 to 12 carbon atoms, and part or all of hydrogen atoms in these groups may be optionally substituted by an alkoxy group or the like; $R^{101b}$ and $R^{101c}$ may form a ring, and when they form the ring, $R^{101b}$ and $R^{101c}$ each represents an alkylene group having 1 to 6 carbon atoms; K represents a non-nucleophilic counter ion; $R^{101d}$, $R^{101e}$, $R^{101f}$, and $R^{101g}$ represent a hydrogen atom, or the groups whose definition is as same as that of $R^{101a}$, $R^{101b}$, and $R^{101c}$; $R^{101d}$ and $R^{101e}$, and $R^{101d}$, $R^{101e}$, and $R^{101f}$ may form a ring, and when they form the ring, $R^{101d}$ and $R^{101e}$, and $R^{101d}$, $R^{101e}$, and $R^{101f}$ represent an alkylene group having 3 to 10 carbon atoms, or a heteroaromatic ring having a nitrogen atom in the ring of the formulae thereof.

$R^{101a}$, $R^{101b}$, $R^{101c}$, $R^{101d}$, $R^{101e}$, $R^{101f}$, and $R^{101g}$ may be the same or different with each other, wherein specific example thereof includes, as the alkyl group, a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cycloheptyl group, a cyclopropylmethyl group, a 4-methylcyclohexyl group, a cyclohexylmethyl group, a norbornyl group, and an adamantyl group. Illustrative example of the alkenyl group includes a vinyl group, an allyl group, a propenyl group, a butenyl group, a hexenyl group, and a cyclohexenyl group. Illustrative example of the oxoalkyl group includes a 2-oxocyclopentyl group and a 2-oxocyclohexyl group, as well as a 2-oxopropyl group, a 2-cyclopentyl-2-oxoethyl group, a 2-cyclohexyl-2-oxoethyl group, and a 2-(4-methylcyclohexyl)-2-oxoethyl group. Illustrative example of the oxoalkenyl group includes a 2-oxo-4-cyclohexenyl group and a 2-oxo-4-propenyl group. Illustrative example of the aryl group includes a phenyl group, a naphthyl group, and the like; alkoxyphenyl groups such as a p-methoxyphenyl group, a m-methoxyphenyl group, an o-methoxyphenyl group, an ethoxyphenyl group, a p-tert-butoxyphenyl group, and a m-tert-butoxyphenyl group; alkylphenyl groups such as a 2-methylphenyl group, a 3-methylphenyl group, a 4-methylphenyl group, an ethylphenyl group, a 4-tert-butylphenyl group, a 4-butylphenyl group, and a dimethylphenyl group; alkylnaphthyl groups such as a methylnaphthyl group and an ethylnaphthyl group; alkoxynaphthyl groups such as a methoxynaphthyl group and an ethoxynaphthyl group; dialkylnaphthyl groups such as a dimethylnaphthyl group and a diethylnaphthyl group; and dialkoxynaphthyl groups such as a dimethoxynaphthyl group and a diethoxynaphthyl group. Illustrative example of the aralkyl group includes a benzyl group, a phenylethyl group, and a phenetyl group. Illustrative example of the aryl oxoalkyl group includes 2-aryl-2-oxoethyl groups such as a 2-phenyl-2-oxoethyl group, a 2-(1-naphtyl)-2-oxoethyl group, and a 2-(2-naphtyl)-2-oxoethyl group. Illustrative example of the non-nucleophilic counter ion $K^-$ includes halide ions such as a chloride ion and a bromide ion; fluoroalkyl sulfonates such as triflate, 1,1,1-trifluoroethane sulfonate, and nonafluorobutane sulfonate; arylsulfonates such as tosylate, benzene sulfonate, 4-fluorobenzene sulfonate, and 1,2,3,4,5-pentafluorobenzene sulfonate; alkylsulfonates such as mesylate and butane sulfonate; imidic acids such as bis(trifluoromethylsulfonyl)imide, bis(perfluoroethylsulfonyl)imide, and bis(perfluorobutylsulfonyl)imide; methidic acids such as tris(trifluoromethylsulfonyl)methide and tris(perfluoroethylsulfonyl)methide; and sulfonates such as the sulfonate whose α-position is substituted by fluorine as illustrated in the following general formula (K-1) and the sulfonate whose α-position and β-position are substituted by fluorine as illustrated in the following general formula (K-2).

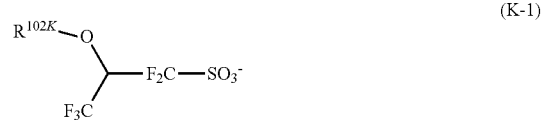

(K-1)

(K-2)

In the general formula (K-1), $R^{102k}$ represents a hydrogen atom, or a linear, branched, or cyclic, alkyl or acyl group, each having 1 to 20 carbon atoms, or an alkenyl group having 2 to 20 carbon atoms, or an aryl group or aryloxy group, each having 6 to 20 carbon atoms. In the general formula (K-2), $R^{103k}$ represents a hydrogen atom, or a linear, branched, or cyclic alkyl group having 1 to 20 carbon atoms, or an alkenyl group having 2 to 20 carbon atoms, or an aryl group having 6 to 20 carbon atoms.

Illustrative example of the heteroaromatic ring in which $R^{101d}$, $R^{101e}$, $R^{101f}$, and $R^{101g}$ have a nitrogen atom in the formula in the ring includes imidazole derivatives (for example, imidazole, 4-methylimidazole, and 4-methyl-2-phenylimidazole), pyrazole derivatives, furazan derivatives, pyrroline derivatives (for example, pyrroline and 2-methyl-1-pyrroline), pyrrolidine derivatives (for example, pyrrolidine, N-methylpyrrolidine, pyrrolidinone, and N-methylpyrrolidone), imidazoline derivatives, imidazolidine derivatives, pyridine derivatives (for example, pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (for example, quinoline and 3-quinoline carbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

(P1a-1) and (P1a-2) have both effects of the acid generator by light and the acid generator by heat; but (P1a-3) acts as the acid generator by heat.

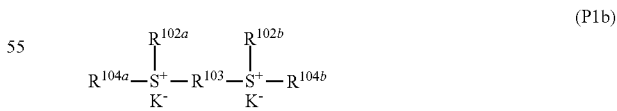

(P1b)

In the above general formula, $R^{102a}$ and $R^{102b}$ each represents a linear, branched, or cyclic alkyl group having 1 to 8 carbon atoms. $R^{103}$ represents a linear, branched, or cyclic alkylene group having 1 to 10 carbon atoms. $R^{104a}$ and $R^{104b}$ each represents a 2-oxoalkyl group having 3 to 7 carbon atoms. The ion K represents a non-nucleophilic counter ion.

Specific example of the alkyl group of $R^{102a}$ and $R^{102b}$ includes a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cyclopropylmethyl group, a 4-methylcyclohexyl group, and a cyclohexylmethyl group. Specific example of the alkylene group of $R^{103}$ includes a methylene group, an ethylene group, a propylene group, a butylene group, a pentylene group, a hexylene group, a heptylene group, an octylene group, a nonylene group, a 1,4-cyclohexylene group, a 1,2-cyclohexylene group, a 1,3-cyclopentylene group, a 1,4-cyclooctylene group, and a 1,4-cyclohexane dimethylene group. Specific example of the 2-oxoalkyl group in $R^{104a}$ and $R^{104b}$ includes a 2-oxopropyl group, a 2-oxocyclopentyl group, a 2-oxocyclohexyl group, and a 2-oxocycloheptyl group. Illustrative example of $K^-$ includes the same ions as those explained in the formulae (P1a-1), (P1a-2), and (P1a-3).

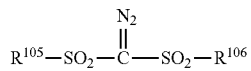

(P2)

In the above general formula, $R^{105}$ and $R^{106}$ represent a linear, branched, or cyclic, alkyl or halogenated alkyl group having 1 to 12 carbon atoms, or an aryl or halogenated aryl group having 6 to 20 carbon atoms, or an aralkyl group having 7 to 12 carbon atoms.

Illustrative example of the alkyl group of $R^{105}$ and $R^{106}$ includes a methyl group, an ethyl group, a propyl group, an isopropyl group, a n-butyl group, a sec-butyl group, a tert-butyl group, a pentyl group, a hexyl group, a heptyl group, an octyl group, an amyl group, a cyclopentyl group, a cyclohexyl group, a cycloheptyl group, a norbornyl group, and an adamantyl group. Illustrative example of the halogenated alkyl group includes a trifluoromethyl group, a 1,1,1-trifluoroethyl group, a 1,1,1-trichloroethyl group, and a nonafluorobutyl group. Illustrative example of the aryl group includes a phenyl group; alkoxyphenyl groups such as a p-methoxyphenyl group, a m-methoxyphenyl group, an o-methoxyphenyl group, an ethoxyphenyl group, a p-tert-butoxyphenyl group, and a m-tert-butoxyphenyl group; alkylphenyl groups such as a 2-methylphenyl group, a 3-methylphenyl group, a 4-methylphenyl group, an ethylphenyl group, a 4-tert-butylphenyl group, a 4-butylphenyl group, and a dimethylphenyl group. Illustrative example of the halogenated aryl group includes a fluorophenyl group, a chlorophenyl group, and a 1,2,3,4,5-pentafluorophenyl group. Illustrative example of the aralkyl group includes a benzyl group and a phenetyl group.

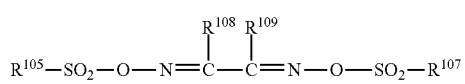

(P3)

In the above general formula, $R^{107}$, $R^{108}$, and $R^{109}$ represent a linear, branched, or cyclic, alkyl or halogenated alkyl group, each having 1 to 12 carbon atoms, or an aryl or halogenated aryl group having 6 to 20 carbon atoms, or an aralkyl group having 7 to 12 carbon atoms. $R^{108}$ and $R^{109}$ may be bonded to each other to form a cyclic structure; and when the cyclic structure is formed, $R^{108}$ and $R^{109}$ represent a linear or branched alkylene group having 1 to 6 carbon atoms. $R^{105}$ represents the same as those in the formula (P2).

The alkyl group, the halogenated alkyl group, the aryl group, the halogenated aryl group, and the aralkyl group of $R^{107}$, $R^{108}$, and $R^{109}$ are the same as those explained in $R^{105}$ and $R^{106}$. Meanwhile, illustrative example of the alkylene group of $R^{108}$ and $R^{109}$ includes a methylene group, an ethylene group, a propylene group, a butylene group, and a hexylene group.

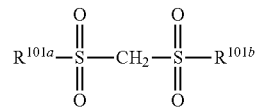

(P4)

In the above general formula, $R^{101a}$ and $R^{101b}$ represent the same as before.

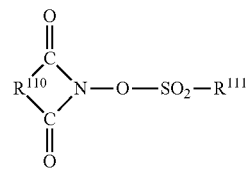

(P5)

In the above general formula, $^{110}$ represents an arylene group having 6 to 10 carbon atoms, an alkylene group having 1 to 6 carbon atoms, or an alkenylene group having 2 to 6 carbon atoms, wherein part or all of the hydrogen atoms of these groups may be further substituted by a linear or branched alkyl or alkoxy group having 1 to 4 carbon atoms, a nitro group, an acetyl group, or a phenyl group. $R^{111}$ represents a linear, branched, or substituted alkyl, alkenyl, or alkoxyalkyl group having 1 to 8 carbon atoms, a phenyl group, or a naphthyl group, wherein part or all of the hydrogen atoms in these groups may be further substituted by an alkyl or alkoxy group having 1 to 4 carbon atoms; or a phenyl group optionally substituted by an alkyl or alkoxy group having 1 to 4 carbon atoms, a nitro group, or an acetyl group; or a heteroaromatic group having 3 to 5 carbon atoms; or a chlorine atom or a fluorine atom.

Here, illustrative example of $R^{110}$ includes, as the arylene group, a 1,2-phenylene group and 1,8-naphthylene group; as the alkylene group, a methylene group, an ethylene group, a trimethylene group, a tetramethylene group, a phenylethylene group, and a norbornane-2,3-diyl group; and as the alkenylene group, a 1,2-vinylene group, a 1-phenyl-1,2-vinylene group, and a 5-norbornene-2,3-diyl group. In $R^{111}$, the alkyl group represents the same as those of $R^{101a}$ to $R^{101c}$, while illustrative example of the alkenyl group includes a vinyl group, a 1-propenyl group, an allyl group, a 1-butenyl group, a 3-butenyl group, an isoprenyl group, a 1-pentenyl group, a 3-pentenyl group, a 4-pentenyl group, a dimethylallyl group, a 1-hexenyl group, a 3-hexenyl group, a 5-hexenyl group, a 1-heptenyl group, a 3-heptenyl group, a 6-heptenyl group, and a 7-octenyl group; illustrative example of the alkoxyalkyl group includes a methoxymethyl group, an ethoxymethyl group, a propoxymethyl group, a butoxymethyl group, a pentyloxymethyl group, a hexyloxymethyl group, a heptyloxymethyl group, a methoxyethyl group, an ethoxyethyl group, a propoxyethyl group, a butoxyethyl group, a pentyloxyethyl group, a hexyloxyethyl group, a methoxypropyl group, an ethoxypropyl group, a propoxypropyl group, a butoxypropyl group, a methoxybutyl group, an ethoxybutyl group, a propoxybutyl group, a methoxypentyl group, an ethoxypentyl group, a methoxyhexyl group, and a methoxyheptyl group.

Meanwhile, illustrative example of the optionally substituted alkyl group having 1 to 4 carbon atoms includes a methyl group, an ethyl group, a propyl group, an isopropyl group, a n-butyl group, an isobutyl group, and a tert-butyl group; illustrative example of the alkoxy group having 1 to 4 carbon atoms includes a methoxy group, an ethoxy group, a propoxy group, an isopropoxy group, a n-butoxy group, an isobutoxy group, and a tert-butoxy group; illustrative example of the phenyl group optionally substituted with an alkyl group having 1 to 4 carbon atoms, an alkoxy group, a nitro group, or an acetyl group includes a phenyl group, a tollyl group, a p-tert-butoxyphenyl group, a p-acetylphenyl group, and a p-nitrophenyl group; and illustrative example of the heteroaromatic group having 3 to 5 carbon atoms includes a pyridyl group and a furyl group.

With regard to the acid generator, illustrative example of the onium salt includes tetramethyl ammonium trifluoromethane sulfonate, tetramethyl ammonium nonafluorobutane sulfonate, triethyl ammonium nonafluorobutane sulfonate, pyridinium nonafluorobutane sulfonate, triethyl ammonium camphor sulfonate, pyridinium camphor sulfonate, tetra-n-butyl ammonium nonafluorobutane sulfonate, tetraphenyl ammonium nonafluorobutane sulfonate, tetramethyl ammonium p-toluene sulfonate, diphenyl iodonium trifluoromethane sulfonate, (p-tert-butoxyphenyl) phenyl iodonium trifluoromethane sulfonate, diphenyl iodonium p-toluene sulfonate, (p-tert-butoxyphenyl)phenyl iodonium p-toluene sulfonate, triphenylsulfonium trifluoromethane sulfonate, (p-tert-butoxyphenyl) diphenylsulfonium trifluoromethane sulfonate, bis(p-tert-butoxyphenyl) phenyl sulfonium trifluoromethane sulfonate, tris(p-tert-butoxyphenyl) sulfonium trifluoromethane sulfonate, triphenyl sulfonium p-toluene sulfonate, (p-tert-butoxyphenyl) diphenyl sulfonium p-toluene sulfonate, bis(p-tert-butoxyphenyl) phenyl sulfonium p-toluene sulfonate, tris(p-tert-butoxyphenyl) sulfonium p-toluene sulfonate, triphenyl sulfonium nonafluorobutane sulfonate, triphenyl sulfonium butanesulfonate, trimethyl sulfonium trifluoromethane sulfonate, trimethyl sulfonium p-toluene sulfonate, cyclohexylmethyl(2-oxocyclohexyl) sulfonium trifluoromethane sulfonate, cyclohexylmethyl(2-oxocyclohexyl) sulfonium p-toluene sulfonate, dimethylphenyl sulfonium trifluoromethane sulfonate, dimethylphenyl sulfonium p-toluene sulfonate, dicyclohexylphenyl sulfonium trifluoromethane sulfonate, dicyclohexylphenyl sulfonium p-toluene sulfonate, trinaphthyl sulfonium trifluoromethane sulfonate, (2-norbonyl)methyl(2-oxocyclohexyl) sulfonium trifluoromethane sulfonate, ethylene bis[methyl(2-oxocyclopentyl] sulfonium trifluoromethane sulfonate], 1,2'-naphthalenecarbonylmethyl tetrahydrothiophenium triflate, triethyl ammonium nonaflate, tributyl ammonium nonaflate, tetraethyl ammonium nonaflate, tetrabutyl ammonium nonaflate, triethyl ammonium bis(trifluoromethylsulfonyl)imide, and triethyl ammonium tris(perfluoroethylsulfonyl)methide.

Illustrative example of the diazomethane derivative includes bis(benzenesulfonyl) diazomethane, bis(p-toluenesulfonyl) diazomethane, bis(xylenesulfonyl) diazomethane, bis(cyclohexylsulfonyl) diazomethane, bis(cyclopentylsulfonyl) diazomethane, bis(n-butylsulfonyl) diazomethane, bis(isobutylsulfonyl) diazomethane, bis(sec-butylsulfonyl) diazomethane, bis(n-propylsulfonyl) diazomethane, bis(isopropylsulfonyl) diazomethane, bis(tert-butylsulfonyl) diazomethane, bis(n-amylsulfonyl) diazomethane, bis(isoamylsulfonyl) diazomethane, bis(sec-amylsulfonyl) diazomethane, bis(tert-amylsulfonyl) diazomethane, 1-cyclohexylsulfonyl-1-(tert-butylsulfonyl) diazomethane, 1-cyclohexylsulfonyl-1-(tert-amylsulfonyl) diazomethane, and 1-tert-amylsulfonyl-1-(tert-butylsulfonyl) diazomethane.

Illustrative example of the glyoxime derivative includes bis-O-(p-toluenesulfonyl)-α-dimethyl glyoxime, bis-O-(p-toluenesulfonyl)-α-diphenyl glyoxime, bis-O-(p-toluenesulfonyl)-α-dicyclohexyl glyoxime, bis-O-(p-toluenesulfonyl)-2,3-pentanedion glyoxime, bis-O-(p-toluenesulfonyl)-2-methyl-3,4-pentanedion glyoxime, bis-O-(n-butanesulfonyl)-α-dimethyl glyoxime, bis-O-(n-butanesulfonyl)-α-diphenyl glyoxime, bis-O-(n-butanesulfonyl)-α-dicyclohexyl glyoxime, bis-O-(n-butanesulfonyl)-2,3-pentanedion glyoxime, bis-O-(n-butanesulfonyl)-2-methyl-3,4-pentanedion glyoxime, bis-O-(methanesulfonyl)-α-dimethyl glyoxime, bis-O-(trifluoromethanesulfonyl)-α-dimethyl glyoxime, bis-O-(1,1,1-trifluoroethanesulfonyl)-α-dimethyl glyoxime, bis-O-(tert-butanesulfonyl)-α-dimethyl glyoxime, bis-O-(perfluorooctanesulfonyl)-α-dimethyl glyoxime, bis-O-(cyclohexanesulfonyl)-α-dimethyl glyoxime, bis-O-(benzenesulfonyl)-α-dimethyl glyoxime, bis-O-(p-fluorobenzenesulfonyl)-α-dimethyl glyoxime, bis-O-(p-tert-butylbenzenesulfonyl)-α-dimethyl glyoxime, bis-O-(xylenesulfonyl)-α-dimethyl glyoxime, and bis-O-(camphorsulfonyl)-α-dimethyl glyoxime.

Illustrative example of the bissulfone derivative includes bisnaphthyl sulfonyl methane, bistrifuloromethyl sulfonyl methane, bismethyl sulfonyl methane, bisethyl sulfonyl methane, bispropyl sulfonyl methane, bisisopropyl sulfonyl methane, bis-p-toluene sulfonyl methane, and bisbenzene sulfonyl methane.

Illustrative example of the β-ketosulfone derivative includes 2-cyclohexylcarbonyl-2-(p-toluenesulfonyl) propane and 2-isopropylcarbonyl-2-(p-toluenesulfonyl) propane.

Illustrative example of the disulfone derivative includes diphenyl disulfone derivatives and dicyclohexyl disulfone derivatives.

Illustrative example of the nitrobenzyl sulfonate derivative includes 2,6-dinitrobenzyl p-toluene sulfonate and 2,4-dinitrobenzyl p-toluene sulfonate.

Illustrative example of the sulfonate ester derivative includes 1,2,3-tris(methanesulfonyloxy)benzene, 1,2,3-tris(trifuoromethanesulfonyloxy)benzene, and 1,2,3-tris(p-toluenesulfonyloxy)benzene.

Illustrative example of the sulfonate ester derivative of an N-hydroxyimide compound includes N-hydroxysuccinimide methane sulfonate ester, N-hydroxysuccinimide trifuloromethane sulfonate ester, N-hydroxysuccinimide ethane sulfonate ester, N-hydroxysuccinimide 1-propane sulfonate ester, N-hydroxysuccinimide 2-propane sulfonate ester, N-hydroxysuccinimide 1-pentane sulfonate ester, N-hydroxysuccinimide 1-octane sulfonate ester, N-hydroxysuccinimide p-toluene sulfonate ester, N-hydroxysuccinimide p-methoxybenzene sulfonate ester, N-hydroxysuccinimide 2-chloroethane sulfonate ester, N-hydroxysuccinimide benzene sulfonate ester, N-hydroxysuccinimide 2,4,6-trimethylbenzene sulfonate ester, N-hydroxysuccinimide 1-naphthalene sulfonate ester, N-hydroxysuccinimide 2-naphthalene sulfonate ester, N-hydroxy-2-phenylsuccinimide methane sulfonate ester, N-hydroxymaleimide methane sulfonate ester, N-hydroxymaleimide ethane sulfonate ester, N-hydroxy-2-phenylmaleimide methane sulfonate ester, N-hydroxygultarimide methane sulfonate ester, N-hydroxygultarimide benzene sulfonate ester, N-hydroxyphthalimide methane sulfonate ester, N-hydroxyphthalimide benzene sulfonate ester, N-hydroxyphthalimide trifluoromethane sulfonate ester, N-hydroxyphthalimide p-toluene sulfonate ester, N-hydroxynaphthalimide methane sulfonate ester, N-hydroxynaphthalimide benzene sulfonate ester, N-hydroxy-5-norbornene-2,3-dicarboxyimide methane sulfonate ester, N-hydroxy-5-norbornene-2,3-dicarboxyimide trifluoromethane sulfonate ester, and N-hydroxy-5-norbornene-2,3-dicarboxyimide p-toluene sulfonate ester.

Among them, especially preferably used acid generators are as follows: onium salts such as triphenyl sulfonium trifluoromethane sulfonate, (p-tert-butoxyphenyl) diphenyl sulfonium trifluoromethane sulfonate, tris(p-tert-butoxyphenyl) sulfonium trifluoromethane sulfonate, triphenyl sulfonium p-toluene sulfonate, (p-tert-butoxyphenyl) diphenyl sulfonium p-toluene sulfonate, tris(p-tert-butoxyphenyl) sulfonium p-toluene sulfonate, trinaphthyl sulfonium trifluoromethane sulfonate, cyclohexyl methyl (2-oxocyclohexyl) sulfonium trifluoromethane sulfonate, (2-norbornyl) methyl (2-oxocyclohexyl) sulfonium trifluoromethane sulfonate, and 1,2'-naphthalenecarbonylmethyl tetrahydrothiophenium triflate; diazomethane derivatives such as bis(benzenesulfonyl) diazomethane, bis(p-toluenesulfonyl) diazomethane, bis(cyclohexylsulfonyl) diazomethane, bis(n-butylsulfonyl) diazomethane, bis(isobutylsulfonyl) diazomethane, bis(sec-butylsulfonyl) diazomethane, bis(n-propylsulfonyl) diazomethane, bis(isopropylsulfonyl) diazomethane, and bis (tert-butylsulfonyl) diazomethane; glyoxime derivatives such as bis-O-(p-toluenesulfonyl)-α-dimethyl glyoxime and bis-O-(n-butanesulfonyl)-α-dimethyl glyoxime; bissulfone derivatives such as bisnaphthyl sulfonyl methane; and sulfonate ester derivatives of an N-hydroxyimide compound such as N-hydroxysuccinimide methane sulfonate ester, N-hydroxysuccinimide trifluoromethane sulfonate ester, N-hydroxysuccinimide 1-propane sulfonate ester, N-hydroxysuccinimide 2-propane sulfonate ester, N-hydroxysuccinimide 1-pentane sulfonate ester, N-hydroxysuccinimide p-toluene sulfonate ester, N-hydroxynaphthalimide methane sulfonate ester, and N-hydroxynaphthalimide benzene sulfonate ester.

Meanwhile, the acid generator mentioned above can be used singly or as a combination of two or more of them. Addition amount of the acid generator is preferably in the range of 0.05 to 50 parts by mass, while more preferably in the range of 0.1 to 10 parts by mass, relative to 100 parts by mass of the base resin. When the addition amount is 0.05 or more parts by mass, a risk of insufficient crosslinking reaction due to small amount of acid generation can be reduced; and when the addition amount is 50 or less parts by mass, a risk of causing a mixing phenomenon due to migration of the acid to the upper resist layers can be avoided.

[(D) Component]

The resist underlayer film composition of the present invention may be blended with (D) surfactant in order to improve applicability thereof in spin coating. Illustrative example of the usable surfactant includes those described in the paragraphs [0142] to [0147] of Japanese Patent Laid-Open Publication No. 2009-269953.

[(E) Component]

The resist underlayer film composition of the present invention may also be blended with (E) crosslinking agent in order to enhance the curability and further suppress the intermixing with the upper layer films. There is no particular restriction in the crosslinking agent, so that heretofore known crosslinking agents with various types may be widely used. Illustrative example thereof includes a melamine-type crosslinking agent, a glycoluril-type crosslinking agent, a benzoguanamine-type crosslinking agent, a urea-type crosslinking agent, a β-hydroxyalkylamide-type crosslinking agent, an isocyanurate-type crosslinking agent, an aziridine-type crosslinking agent, an oxazoline-type crosslinking agent, and an epoxy-type crosslinking agent.

Specific example of the melamine-type crosslinking agent includes hexamethoxymethylated melamine, hexabutoxymethylated melamine, as well as an alkoxy- and/or hydroxy-substituted compound thereof and partial self-condensed compound thereof. Specific example of the glycoluril-type crosslinking agent includes tetramethoxymethylated glycoluril, tetrabutoxymethylated glycoluril, as well as an alkoxy- and/or hydroxy-substituted compound thereof and partial self-condensed compound thereof. Specific example of the benzoguanamine-type crosslinking agent includes tetramethoxymethylated benzoguanamine, tetrabutoxymethylated benzoguanamine, as well as an alkoxy- and/or hydroxy-substituted compound thereof and partial self-condensed compound thereof. Specific example of the urea-type crosslinking agent includes dimethoxymethylated dimethoxy ethylene urea, as well as an alkoxy- and/or hydroxy-substituted compound thereof and partial self-condensed compound thereof. Specific example of the β-hydroxyalkylamide-type crosslinking agent includes N,N,N',N'-tetra(2-hydroxyethyl)adipic amide. Specific example of the isocyanurate-type crosslinking agent includes triglycidyl isocyanurate and triallyl isocyanurate. Specific example of the aziridine-type crosslinking agent includes 4,4'-bis(ethyleneiminocarbonylamino) diphenylmethane and 2,2-bishydroxymethylbutanol-tris[3-(1-aziridinyl)propionate]. Specific example of the oxazoline-type crosslinking agent includes 2,2'-isopropylidene bis(4-benzyl-2-oxazoline), 2,2'-isopropylidene bis(4-phenyl-2-oxazoline), 2,2'-methylene bis 4,5-diphenyl-2-oxazoline, 2,2'-methylene bis-4-phenyl-2-oxazoline, 2,2'-methylene bis-4-tert-butyl-2-oxazoline, 2,2'-bis(2-oxazoline), 1,3-phenylene bis(2-oxazoline), 1,4-phenylene bis(2-oxazoline), and 2-isopropenyl oxazoline copolymer. Specific example of the epoxy-type crosslinking agent includes diglycidyl ether, ethyleneglycol diglycidyl ether, 1,4-butanediol diglycidyl ether, 1,4-cyclohexane dimethanol diglycidyl ether, poly(methacrylate diglycidyl), trimethylolethane triglycidyl ether, trimethylolpropane triglycidyl ether, and pentaerythritol tetraglycidyl ether.

[(F) Component]

The resist underlayer film composition of the present invention may be blended with (F) plasticizer in order to further improve the planarization and gap-filing characteristics. There is no particular restriction in the plasticizer, so that heretofore known plasticizers of various types may be widely used. Illustrative example thereof includes low molecular weight compounds such as phthalate esters, adipate esters, phosphate esters, trimellitate esters, and citrate esters, as well as polymers such as polyethers, polyesters, and polyacetals described in Japanese Patent Laid-Open Publication No. 2013-253227.

[(G) Component]

The resist underlayer film composition of the present invention may be blended with (G) pigment in order to further improve the resolution upon patterning of the multilayer lithography. There is no particular restriction in the pigment so far as it is the compound having an appropriate absorbance in the irradiation wavelength, so that various heretofore known compounds can be widely used. Illustrative example thereof includes benzenes, naphthalenes, anthracenes, phenanthrenes, pyrenes, isocyanuric acids, and triazines.

It is preferable that the resist underlayer film composition of the present invention can give the resist underlayer film exhibiting the resistance to the ammonia-containing hydrogen peroxide aqueous solution. The resist underlayer film composition as mentioned above can form the resist underlayer film which is excellent in the resistance to the basic hydrogen peroxide aqueous solution, so that this composition can also be used in the wet etching process using the basic hydrogen peroxide aqueous solution.

The basic hydrogen peroxide aqueous solution is generally used in cleaning of a semiconductor wafer. Especially, a mixture of 5 parts by mass of deionized water, 1 parts by mass of 29% by mass of aqueous ammonia solution, and 1 parts by mass of 30% by mass of hydrogen peroxide aqueous solution is called as SC1 (Standard Clean-1); and this mixture becomes a standard chemical solution for rinsing to remove organic impurities and microparticles on the wafer surface. In addition, by the basic hydrogen peroxide aqueous solution, delamination or etching processing is possible not only for some metals and metal compounds but also for a silicon-containing resist intermediate film that is designed for wet delamination. The composition of the basic hydrogen peroxide aqueous solution is not particularly restricted; however, typically this is a mixture of deionized water, hydrogen peroxide, and ammonia. In this case, concentration of hydrogen peroxide is preferably in the range of 0.1 to 10% by mass, while more preferably in the range of 0.2 to 5% by mass; and concentration of ammonia is preferably in the range of 0.1 to 10% by mass, while more preferably in the range of 0.2 to 5% by mass. The temperature in the processing is preferably in the range of 0 to 90° C., while more preferably in the range of 20 to 80° C.

Meanwhile, the test of the resistance of the resist underlayer film to the basic hydrogen peroxide aqueous solution will be explained. At first, under the coating conditions to be mentioned later, onto a silicon wafer which is cut to the size of 3 cm square the resist underlayer film composition is applied so as to give the film thickness of about 100 nm. Thereafter, this wafer piece is soaked in the 1.0% by mass hydrogen peroxide aqueous solution containing 0.5% by mass of ammonia at 70° C. for 5 minutes, and then, this is rinsed with deionized water; thereafter, whether or not the resist underlayer film is delaminated from the wafer can be examined visually. When part or all of the resist underlayer film is delaminated thereby exposing the silicon wafer surface, the resist underlayer film subjected to the test is judged to be insufficient in the resistance to the basic hydrogen peroxide aqueous solution.

Namely, in the resist underlayer film formed by the resist underlayer film composition of the present invention, it is preferable that delamination of the resist underlayer film be not observed upon soaking the silicon substrate formed with this resist underlayer film in the 1.0% by mass hydrogen peroxide aqueous solution containing 0.5% by mass of ammonia at 70° C. for 5 minutes.

Meanwhile, in the present invention, thickness of the resist underlayer film can be arbitrarily chosen; however, the thickness is preferably in the range of 30 to 20,000 nm, while especially preferably in the range of 50 to 15,000 nm. In the case of the resist underlayer film for a three-layer resist process, a silicon-containing resist intermediate film may be formed on the resist underlayer film, and on the intermediate film, the resist upper layer film not containing a silicon may be formed. In the case of the resist underlayer film for a two-layer resist process, a resist upper layer film containing a silicon, or a resist upper layer film not containing a silicon may be formed on the resist underlayer film.

(Method for Forming the Resist Underlayer Film)

In the present invention the method for forming the resist underlayer film is provided, wherein the resist underlayer film composition mentioned above is applied onto the substrate to be processed; and then, the resist underlayer film composition is subjected to the heat treatment in the temperature range of 100° C. or more and 500° C. or less, and for a period of in the range of 10 to 600 seconds to form a cured film.

In the method of the present invention for forming the resist underlayer film, the substrate to be processed is coated with the resist underlayer film composition by using a spin coating method or the like; and then, after the solvent is evaporated, baking is carried out in order to prevent mixing with the resist upper layer film and the resist intermediate film, or to facilitate the crosslinking reaction. By using the spin coating method or the like in the way as mentioned above, the excellent gap-filling characteristic can be obtained.

The baking is carried out in the temperature range of 100° C. or more and 500° C. or less, preferably in the range of 100° C. or more and 300° C. or less, while more preferably in the range of 150° C. or more and 280° C. or less, and for a period of in the range of 10 to 600 seconds, while preferably in the range of 10 to 300 seconds. When the baking temperature and time are appropriately controlled within the ranges mentioned above, the planarization and gap-filling characteristics as well as curing characteristic suitable for the use can be obtained. When the baking temperature is 100° C. or more, sufficient cure can be obtained, so that there is no risk of mixing with the upper layer film or with the intermediate film. When the baking temperature is 300° C. or less, thermal decomposition of the base resin is not significant, so that there is no risk of decrease in the film thickness or to cause uneven film surface.

In the method of the present invention for forming the resist underlayer film, as the substrate to be processed, it is preferable also to use the substrate having the structural body with the height of 30 nm or more, or having the step. The method of the present invention for forming the resist underlayer film is especially useful for forming the planarized organic film without voids on the substrate having the structural body with the height of 30 nm or more, or having the step.

(Patterning Process)

In the present invention, the patterning process using the resist underlayer film composition mentioned above is provided. The patterning process of the present invention can be suitably used in multilayer resist processes such as a silicon-containing two-layer resist process, a three-layer resist process using a silicon-containing intermediate film, a four-layer resist process using a silicon-containing intermediate film and an organic antireflective film, or a two-layer resist process not containing a silicon.

Namely, the present invention provides a patterning process, wherein the patterning process is to form a pattern on a substrate to be processed as a two-layer resist process and comprises steps of:

(I-1) forming a resist underlayer film on the substrate to be processed by using the resist underlayer film composition,
(I-2) forming a resist upper layer film on the resist underlayer film by using a photoresist composition,
(I-3) forming a pattern on the resist upper layer film by developing the resist upper layer film by using a developer after the resist upper layer film is pattern-exposed, and
(I-4) transcribing the pattern to the resist underlayer film by dry etching using as a mask the resist upper layer film formed with the pattern.

In addition, the present invention provides a patterning process, wherein the patterning process is to form a pattern on a substrate to be processed as a three-layer resist process and comprises steps of:

(II-1) forming a resist underlayer film on the substrate to be processed by using the resist underlayer film composition,
(II-2) forming a resist intermediate film on the resist underlayer film,
(II-3) forming a resist upper layer film on the resist intermediate film by using a photoresist composition,
(II-4) forming a pattern on the resist upper layer film by developing the resist upper layer film by using a developer after the resist upper layer film is pattern-exposed,
(II-5) transcribing the pattern to the resist intermediate film by dry etching using as a mask the resist upper layer film formed with the pattern, and
(II-6) transcribing the pattern to the resist underlayer film by dry etching using as a mask the resist intermediate film transcribed with the pattern.

In addition, the present invention provides a patterning process, wherein the patterning process is to form a pattern on a substrate to be processed as a four-layer resist process and comprises steps of:

(III-1) forming a resist underlayer film on the substrate to be processed by using the resist underlayer film composition,
(III-2) forming an inorganic hard mask intermediate film selected from a silicon oxide film, a silicon nitride film, and a silicon oxide nitride film on the resist underlayer film,
(III-3) forming an organic antireflective film on the inorganic hard mask intermediate film,
(III-4) forming a resist upper layer film on the organic antireflective film by using a photoresist composition, (III-5) forming a pattern on the resist upper layer film by developing the resist upper layer film by using a developer after the resist upper layer film is pattern-exposed, (III-6) transcribing the pattern to the organic antireflective film and the inorganic hard mask intermediate film by dry etching using as a mask the resist upper layer film formed with the pattern, and (III-7) transcribing the pattern to the resist underlayer film by dry etching using as a mask the inorganic hard mask intermediate film transcribed with the pattern.

Hereunder, the patterning process of the present invention will be explained with regard to the three-layer resist process using a resist intermediate film containing a silicon atom (silicon-containing resist intermediate film) as an example; however, the present invention is not limited to this.

In this case, a resist underlayer film is formed on a substrate to be processed by using the resist underlayer film composition; on this resist underlayer film, a resist intermediate film is formed by using a resist intermediate film composition containing a silicon atom; further on the resist intermediate film, a resist upper layer film is formed by using a photoresist composition to form a multilayer resist film; after a pattern circuit region of the resist upper layer film is exposed to a light (pattern exposure), a pattern is formed on the resist upper layer film by development using a developer; the pattern is transcribed by etching the resist intermediate film by using as a mask the resist upper layer film formed with the pattern; the pattern is transcribed by etching the resist underlayer film by using as a mask the resist intermediate film transcribed with the pattern; and further, the pattern is formed on the substrate to be processed by processing the substrate to be processed by using as a mask the resist underlayer film transcribed with the pattern.

The resist underlayer film in the three-layer resist process can be formed in the way that the resist underlayer film composition is applied onto the substrate to be processed by using a spin coating method or the like, and then, after the solvent is evaporated, baking is carried out in order to prevent the mixing with the resist upper layer film and with the resist intermediate film, or to facilitate a crosslinking reaction. When the composition is applied by a spin coating method or the like, the excellent gap-filling characteristic can be obtained.

The baking is carried out in the temperature range of 100° C. or more and 500° C. or less, preferably in the range of 100° C. or more and 300° C. or less, while more preferably in the range of 150° C. or more and 280° C. or less, and for a period of in the range of 10 to 600 seconds, while preferably in the range of 10 to 300 seconds. When the baking temperature and time are appropriately controlled within the ranges mentioned above, the planarization and gap-filling characteristics as well as curing characteristic suitable for the use can be obtained. When the baking temperature is 100° C. or more, sufficient cure can be obtained, so that there is no risk of mixing with the upper layer film or with the intermediate film. When the baking temperature is 300° C. or less, thermal decomposition of the base resin is not significant, so that there is no risk of decrease in the film thickness or to cause uneven film surface.

The resist intermediate film containing a silicon atom exhibits a resistance to etching by an oxygen gas or a hydrogen gas. Accordingly, etching of the resist underlayer film by using the resist intermediate film as a mask is carried out preferably by using an etching gas mainly comprising an oxygen gas or a hydrogen gas.

For the silicon-containing resist intermediate film in the three-layer resist process, a polysilsesquioxane-based intermediate film can be suitably used. The polysilsesquioxane-based intermediate film can be readily provided with an antireflective effect, so that a reflected light during pattern exposure of the resist upper layer film can be suppressed; and thus, this has an advantage of excellent resolution. Especially, for the exposure to a 193 nm light beam, the resist underlayer film formed of the composition containing large amount of an aromatic group has a high k-value thereby leading to increase in the substrate reflection; however, because the reflection can be suppressed by the resist intermediate film, the substrate reflection can be suppressed to 0.5% or less. For the resist intermediate film having an antireflective effect, the polysilsesquioxane crosslinkable with an acid or a heat having an anthracene pendant is preferably used for exposure to a 248 nm or 157 nm light beam, while the polysilsesquioxane crosslinkable by an acid or a heat having a pendant of a phenyl group or a light-absorbing group having a silicon-silicon bond is preferably used for exposure to a 193 nm light beam.

In this case, formation of the silicon-containing resist intermediate film by a spin coating method is more advantageous than a CVD method in view of convenience and cost.

With regard to the resist upper layer film in the three-layer resist process, either a positive type or a negative type may be used, wherein the same type as the photoresist composition usually used may be used. When the monolayer resist upper layer film is formed by the photoresist composition mentioned above, similarly to the case of forming the resist underlayer film, the spin coating method is preferably used. After the photoresist composition is applied by the spin coating method, a pre-bake is carried out, wherein preferably the temperature thereof is in the range of 60 to 180° C. and the time thereof is in the range of 10 to 300 seconds. Thereafter, by carrying out the exposure to a light in a conventional way, followed by the post exposure bake (PEB), and then by the development, the resist pattern is obtained. Meanwhile, there is no particular restriction in thickness of the resist upper layer film; however, the thickness is preferably in the range of 30 to 500 nm, especially in the range of 50 to 400 nm.

The exposure lights to be used are high energy beams with the wavelength of 300 nm or less; and specific example thereof includes excimer laser beams of 248 nm, 193 nm, and 157 nm; soft X-ray beams of 3 to 20 nm; electronic beams; and X-ray beams.

Next, etching is carried out by using the resist pattern thus obtained as a mask. Etching of the resist intermediate film in the three-layer resist process is carried out with a freon-based gas by using the resist pattern as a mask. Next, the resist underlayer film is processed by etching using as a mask the pattern of the resist intermediate film with an oxygen gas or a hydrogen gas.

Etching of the substrate to be processed in the next step may be carried out by a conventional method, for example, an etching with a gas mainly composed of a freon-based gas when the substrate is $SiO_2$, SiN, or a silica-based insulating film with a low dielectric constant, or an etching with a gas mainly composed of a chlorine-based gas or a bromine-based gas when the substrate is p-Si, Al, or W. When the substrate processing is carried out by etching with a freon-based gas, the resist intermediate film (silicon-containing resist intermediate film) in the three-layer resist process is delaminated simultaneously with the substrate processing. When the substrate is etched with a chlorine-based gas or a bromine-based gas, delamination of the silicon-containing resist intermediate film needs to be carried out separately by dry etching with a freon-based gas after processing of the substrate.

Meanwhile, with regard to the substrate to be processed, a layer to be processed is formed on the substrate. There is no particular restriction in the substrate, wherein a material different from the layer to be processed, such as Si, α-Si, p-Si, $SiO_2$, SiN, SiON, W, TiN, and Al, may be used. With regard to the layer to be processed, various low-k films such as Si, $SiO_2$, SiON, SiN, p-Si, α-Si, W, TiN, W—Si, Al, Cu, and Al—Si, as well as stopper films of them, and the like, may be used, wherein the layer is formed with the thickness of usually in the range of 50 to 10,000 nm, especially in the range of 100 to 5,000 nm.

Meanwhile, when the patterning process of the present invention is used, in addition to general manufacturing processes as mentioned above, various special manufacturing processes can be constructed; and thus, the patterning process of the present invention has a high value in industry.

Firstly, with regard to delamination of the silicon-containing resist intermediate film, generally, delamination by the dry etching is imperative as mentioned above; however, in the patterning process of the present invention, because the resist underlayer film has the resistance to the basic hydrogen peroxide aqueous solution, wet delamination of only the silicon-containing resist intermediate film by using the basic hydrogen peroxide aqueous solution can also be chosen. Namely, in the patterning process of the three-layer resist process of the present invention, a step of removing the resist intermediate film transcribed with the pattern by the wet etching using the basic hydrogen peroxide aqueous solution may be further added after the step of (II-6) mentioned above.

Further, in the case that the substrate to be processed is W, TiN or the like, when the patterning process of the present invention is used, the wet etching processing of the substrate by using the basic hydrogen peroxide aqueous solution can also be chosen. Namely, in the patterning process of the two-layer, three-layer, four-layer resist processes of the present invention, a step of transcribing the pattern to the substrate to be processed by the wet etching using the basic hydrogen peroxide aqueous solution by using as a mask the resist underlayer film transcribed with the pattern may be further added after the step of (I-4), the step of (II-6), or the step of (III-7) mentioned above.

In one example of this case, firstly, the resist underlayer film is formed on the substrate to be processed, and if necessary, on it the resist intermediate film is formed, and then, the resist upper layer film is formed. Next, the resist upper layer film is patterned with a conventional method, and then, the pattern is transcribed to the resist underlayer film by etching. Finally, the substrate to be processed can be patterned by the wet etching using the resist underlayer film as a mask.

In addition, in the patterning process of the two-layer, three-layer, and four-layer resist processes of the present invention, a patterning step of the substrate to be processed by ion implantation using as a mask the resist underlayer film transcribed with the pattern may be added after the step of (I-4), the step of (II-6), or the step of (III-7). In this case, after the pattern processing step by the ion implantation of the substrate to be processed, a step of removing the resist intermediate film transcribed with the pattern may be further added, wherein this removal is carried out by the wet etching using the basic hydrogen peroxide aqueous solution.

The patterning process of the present invention is also suitable for processing of the substrate having the structural body with the height of 30 nm or more, or having the step. Hereunder, one example of such process will be explained.

Firstly, the resist underlayer film is formed on the substrate having steps so as to carry out gap-filling and planarization; and then, after the resist intermediate film is formed if necessary, the resist upper layer film is formed. Next, the resist upper layer film is patterned with a conventional method, and then, the pattern is transcribed to the resist underlayer film by etching. Next, the substrate can be pattern-processed by the ion implantation using the resist underlayer film as a mask. Delamination of the remained resist intermediate film can be carried out by choosing the dry etching or the wet etching as appropriate. Finally, the resist underlayer film can be removed by the dry etching.

At this time, it is preferable to use the resist underlayer film having the dry etching rate faster than the dry etching rate of the resist upper layer film. When the resist underlayer film composition to form the film like this is used (namely, when the dry etching rate of the resist underlayer film to be formed is fast), even the resist underlayer film in the spot where the removal thereof is generally difficult, such as a corner of the steps of the substrate, can be removed without residues by the dry etching; and thus, the composition as mentioned above is further preferable.

In addition, in the patterning process of the present invention, at least, a resist underlayer film is formed on a substrate to be processed by using the resist underlayer film composition; on the resist underlayer film, an inorganic hard mask intermediate film selected from a silicon oxide film, a silicon nitride film, and a silicon oxide nitride film is formed; further on the inorganic hard mask intermediate film, a resist upper layer film is formed by using a photoresist composition; after a pattern circuit region of the resist upper layer film is exposed to a light, a pattern is formed on the resist upper layer film by development using a developer; the pattern is transcribed by etching the inorganic hard mask intermediate film by using as a mask the resist upper layer film formed with the pattern; the pattern is transcribed by etching the resist underlayer film by using as a mask the inorganic hard mask intermediate film transcribed with the pattern; and the pattern is formed on the substrate to be processed by processing the substrate to be processed by using as a mask the resist underlayer film transcribed with the pattern.

In the case that the inorganic hard mask intermediate film is formed on the resist underlayer film as mentioned above, a silicon oxide film, a silicon nitride film, or a silicon oxide nitride film (SiON film) is formed by a CVD method, an ALD method, or the like. The method for forming the nitride film is described in Japanese Patent Laid-Open Publication No. 2002-334869 and International Patent Laid-Open Publication No. 2004/066377. Film thickness of the inorganic hard mask is in the range of 5 to 200 nm, while more preferably in the range of 10 to 100 nm. Especially, the SiON film, which has a high effect as the antireflective film, is used most preferably.

In addition, the present invention can be suitably used in the four-layer resist process using an organic antireflective film. In this case, at least, a resist underlayer film is formed on a substrate to be processed by using the resist underlayer film composition; on the resist underlayer film, an inorganic hard mask intermediate film selected from a silicon oxide film, a silicon nitride film, and a silicon oxide nitride film is formed; on the inorganic hard mask intermediate film, an organic antireflective film is formed; on the organic antireflective film, a resist upper layer film is formed by using a photoresist composition; after a pattern circuit region of the resist upper layer film is exposed to a light, a pattern is formed on the resist upper layer film by development using a developer; the pattern is transcribed by etching the organic antireflective film and the inorganic hard mask intermediate film by using as a mask the resist upper layer film formed with the pattern; the pattern is transcribed by etching the resist underlayer film by using as a mask the inorganic hard mask intermediate film transcribed with the pattern; and the pattern is formed on the substrate to be processed by processing the substrate to be processed by using as a mask the resist underlayer film transcribed with the pattern.

It may be allowed to form the photoresist film as the resist upper layer film on the resist intermediate film; or alternatively, the organic antireflective film (BARC) may be formed on the resist intermediate film by spin coating followed by forming the photoresist film on it. When a SiON film is used as the resist intermediate film, because of two antireflective films of the SiON film and the BARC film, the reflection can be suppressed even in the immersion exposure with high NA of more than 1.0. Formation of the BARC film has an additional merit, i.e., the effect to decrease footing of the photoresist pattern immediately above the SiON film.

One example of the three-layer resist process will be specifically explained as follows by using FIG. 1.

In the case of the three-layer resist process, as depicted in FIG. 1(A), after the resist underlayer film 3 is formed on the layer to be processed 2 that is laminated on the substrate 1, the resist intermediate film 4 is formed, and then, on it the resist upper layer film 5 is formed.

Next, as depicted in FIG. 1(B), the prescribed portion 6 of the resist upper layer film is exposed to a light, and then, PEB (post-exposure bake) and development are carried out to form the resist pattern 5a (FIG. 1(C)). By using as a mask the resist pattern 5a thus obtained, the resist intermediate film 4 is processed by etching using a CF-based gas to form the resist intermediate film pattern 4a (FIG. 1(D)). After the resist pattern 5a is removed, by using as a mask the resist intermediate film pattern 4a thus obtained, the resist underlayer film 3 is processed by an oxygen-based plasma etching or a hydrogen-based plasma etching to form the resist underlayer film pattern 3a (FIG. 1(E)). Further, after the resist intermediate film pattern 4a is removed, by using as a mask the resist underlayer film pattern 3a, the layer to be processed 2 is processed by etching to form the pattern 2a (FIG. 1(F)).

When the inorganic hard mask intermediate film is used, the resist intermediate film 4 is the inorganic hard mask intermediate film; and when the BARC film is formed, the BARC layer is formed between the resist intermediate film 4 and the resist upper layer film 5. The BARC film may be etched continuously prior to etching of the resist intermediate film 4; or alternatively, after etching only the BARC film, the resist intermediate film 4 may be etched with changing the etching equipment or the like.

EXAMPLE

Hereunder, the present invention will be specifically explained by showing Synthesis Examples, Examples, and Comparative Examples; however, the present invention is not restricted by these descriptions.

Meanwhile, measurement of the molecular weight was done by the method described as follows. Namely, the weight average molecular weight (Mw) and the number average molecular weight (Mn) were obtained on the basis of polystyrene equivalent by a gel permeation chromatography (GPC) using an eluent of tetrahydrofuran; and then, the dispersibility (Mw/Mn) was obtained from these values.

In the Synthesis Examples described below, the epoxy compounds (E-X1) to (E-X4) shown below were used,

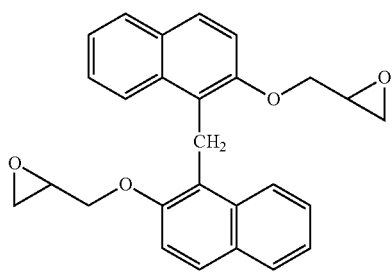
(E-X1)

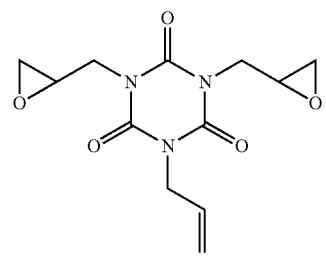
(E-X2)

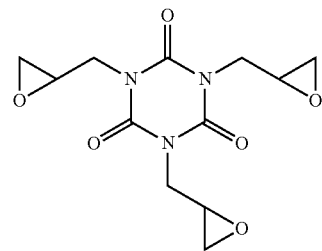
(E-X3)

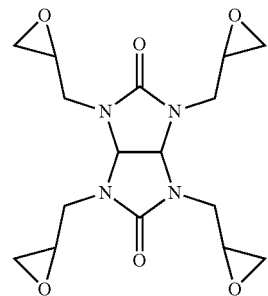
(E-X4)

In the Synthesis Examples described below, the carboxylic acid compounds (C-X1) to (C-X3) shown below were used,

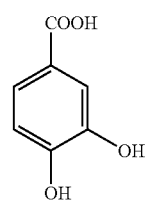
(C-X1)

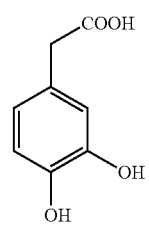
(C-X2)

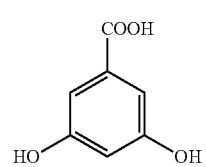
(C-X3)

Synthesis Example 1

Synthesis of Compound (X-1)]

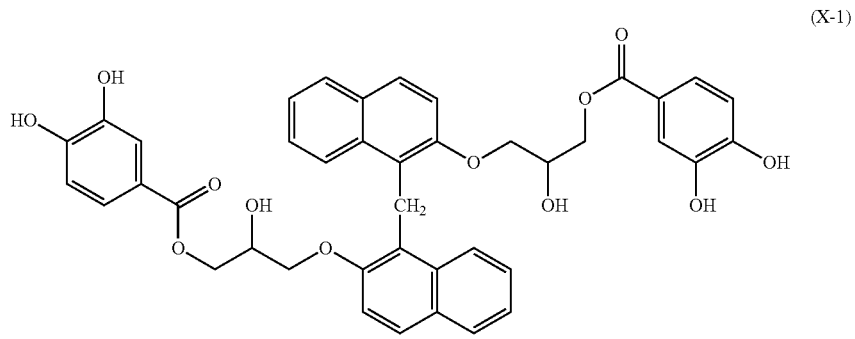 [SMILES: O=C(OCC(O)COc1ccc2ccccc2c1Cc1c(OCC(O)COC(=O)c2ccc(O)c(O)c2)ccc2ccccc12)c1ccc(O)c(O)c1]

(X-1)

After 57.2 g of the epoxy compound (E-X1), 42.8 g of the carboxylic acid compound (C-X1), and 300 g of 2-methoxy-1-propanol were made to a uniform solution at the liquid temperature of 100° C. under a nitrogen atmosphere, 10.0 g of benzyl triethyl ammonium chloride was added to this solution; and the resulting mixture was stirred at the liquid temperature of 120° C. for 12 hours. After the reaction solution was cooled to room temperature, 1,000 g of methyl isobutyl ketone was added to it, and then, the organic phase was washed with 200 g of pure water for 5 times. The organic phase was evaporated to dryness under reduced pressure to obtain the compound (X-1). From the GPC measurement, the weight average molecular weight (Mw) of 780 and the dispersibility (Mw/Mn) of 1.04 were obtained.

Synthesis Examples 2 to 9

Syntheses of Compounds (X-2) to (X-9)

The procedure as same as Synthesis Example 1 was repeated except that the epoxy compound and the carboxylic acid compound described in Tables 1 and 2 were used. In this way, the compounds (X-2) to (X-9) described in Tables 1 and 2 were obtained as the reaction products. The weight average molecular weights (Mw) and dispersibilities (Mw/Mn) of these compounds were obtained; and these values are summarized in Table 3.

TABLE 1

| Synthesis Example | Epoxy compound | Carboxylic acid compound | Carboxylic acid compound | Product |
|---|---|---|---|---|
| 1 | E-X1: 57.2 g | C-X1: 42.8 g | | (X-1) |
| 2 | E-X2: 47.7 g | C-X1: 52.3 g | | |

TABLE 1-continued
| Synthesis Example | Epoxy compound | Carboxylic acid compound | Carboxylic acid compound | Product |
|---|---|---|---|---|
| 3 | E-X3: 39.1 g | C-X1: 60.9 g | | 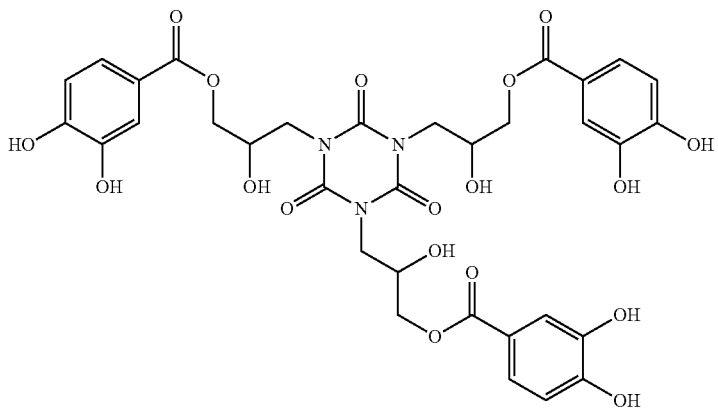 [SMILES: O=C(OCC(O)Cn1c(=O)n(CC(O)COC(=O)c2ccc(O)c(O)c2)c(=O)n(CC(O)COC(=O)c2ccc(O)c(O)c2)c1=O)c1ccc(O)c(O)c1] (X-3) |
| 4 | E-X4: 37.3 g | C-X1: 62.7 g | | 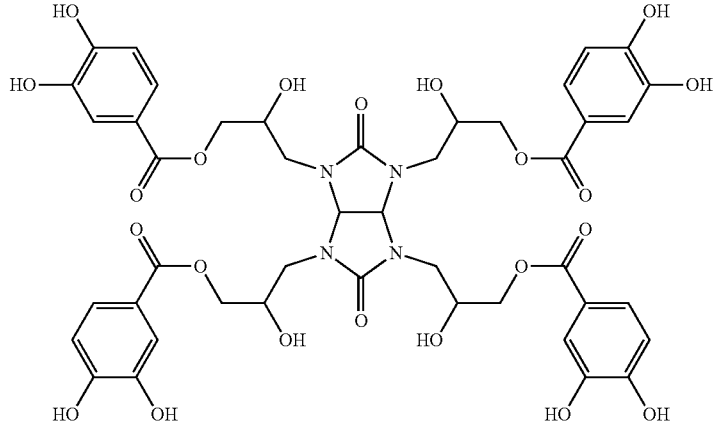 [SMILES: O=C(OCC(O)CN1C(=O)N(CC(O)COC(=O)c2ccc(O)c(O)c2)C2C1N(CC(O)COC(=O)c1ccc(O)c(O)c1)C(=O)N2CC(O)COC(=O)c1ccc(O)c(O)c1)c1ccc(O)c(O)c1] (X-4) |
| 5 | E-X1: 55.1 g | C-X2: 44.9 g | | 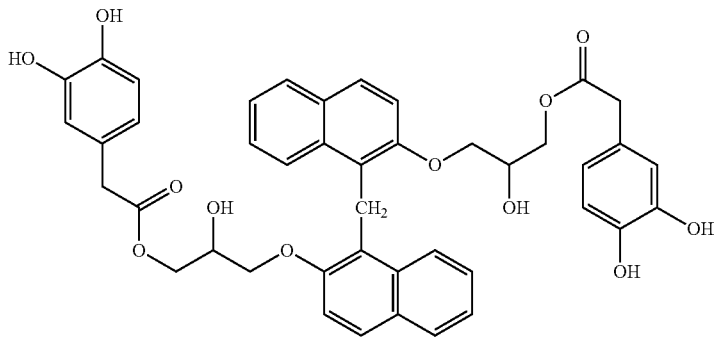 [SMILES: O=C(Cc1ccc(O)c(O)c1)OCC(O)COc1ccc2ccccc2c1Cc1c(OCC(O)COC(=O)Cc2ccc(O)c(O)c2)ccc2ccccc12] (X-5) |

TABLE 1-continued
| Synthesis Example | Epoxy compound | Carboxylic acid compound | Carboxylic acid compound | Product |
|---|---|---|---|---|
| 6 | E-X2: 45.5 g | C-X2: 54.5 g | | 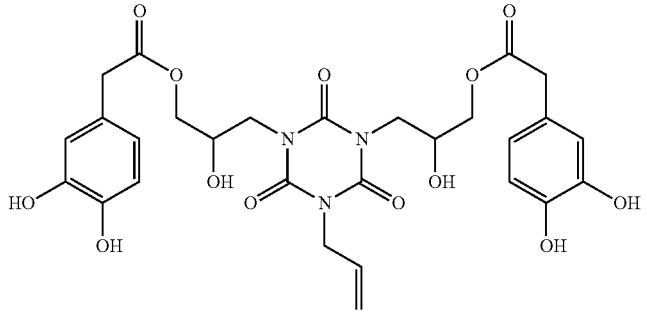 [SMILES: C=CCn1c(=O)n(CC(O)COC(=O)Cc2ccc(O)c(O)c2)c(=O)n(CC(O)COC(=O)Cc2ccc(O)c(O)c2)c1=O] (X-6) |
| 7 | E-X3: 37.1 g | C-X2: 62.9 g | | 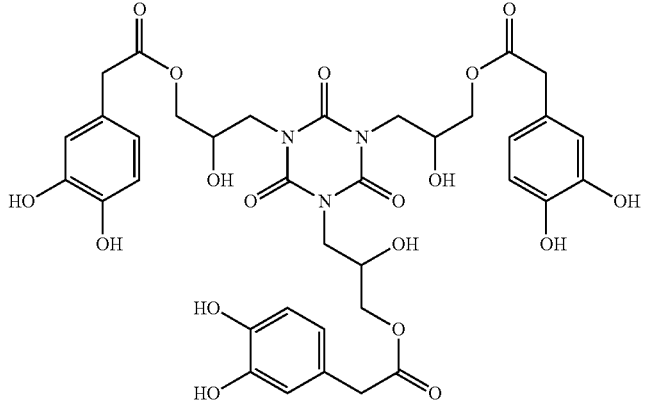 [SMILES: O=C(Cc1ccc(O)c(O)c1)OCC(O)Cn1c(=O)n(CC(O)COC(=O)Cc2ccc(O)c(O)c2)c(=O)n(CC(O)COC(=O)Cc2ccc(O)c(O)c2)c1=O] (X-7) |
TABLE 2
| Synthesis Example | Epoxy compound | Carboxylic acid compound | Carboxylic acid compound | Product |
|---|---|---|---|---|
| 8 | E-X4: 35.3 g | C-X2: 64.7 g | | 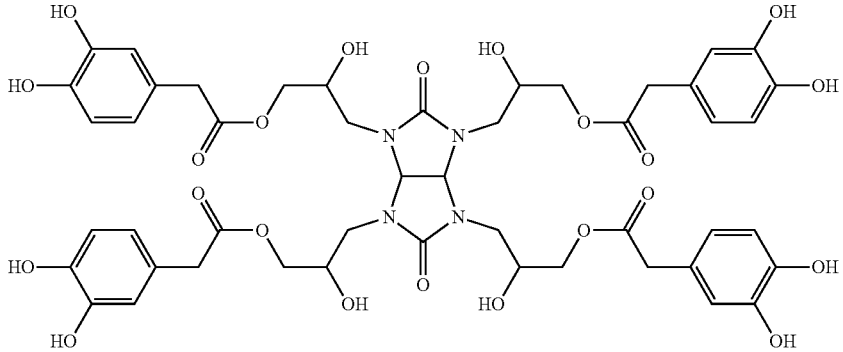 [SMILES: O=C(Cc1ccc(O)c(O)c1)OCC(O)CN1C(=O)N(CC(O)COC(=O)Cc2ccc(O)c(O)c2)C2C1N(CC(O)COC(=O)Cc1ccc(O)c(O)c1)C(=O)N2CC(O)COC(=O)Cc1ccc(O)c(O)c1] (X-8) |

TABLE 2-continued

| Synthesis Example | Epoxy compound | Carboxylic acid compound | Carboxylic acid compound | Product |
|---|---|---|---|---|
| 9 | E-X2: 47.7 g | C-X1: 26.2 g | C-X3: 26.2 g | (structures shown: 25%, 50%, 25%) (X-9) |

TABLE 3

| Synthesis Example | Compound | Mw (Calculated) | Mw (GPC) | Mw/Mn |
|---|---|---|---|---|
| 1 | (X-1) | 720 | 778 | 1.04 |
| 2 | (X-2) | 590 | 607 | 1.03 |
| 3 | (X-3) | 760 | 798 | 1.05 |
| 4 | (X-4) | 983 | 1052 | 1.07 |
| 5 | (X-5) | 748 | 793 | 1.06 |
| 6 | (X-6) | 618 | 636 | 1.03 |
| 7 | (X-7) | 802 | 842 | 1.05 |
| 8 | (X-8) | 1039 | 1132 | 1.09 |
| 9 | (X-9) | 590 | 607 | 1.03 |

For Synthesis Examples hereunder, the compounds (P-X1) to (P-X4) shown below were used,

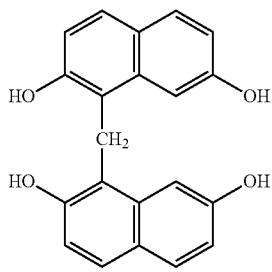
(P-X1)

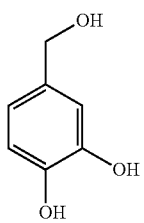
(P-X2)

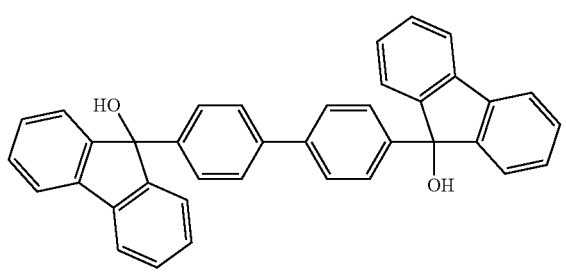
(P-X3)

(P-X4)

Synthesis Example 10

Synthesis of Compound (X-10)

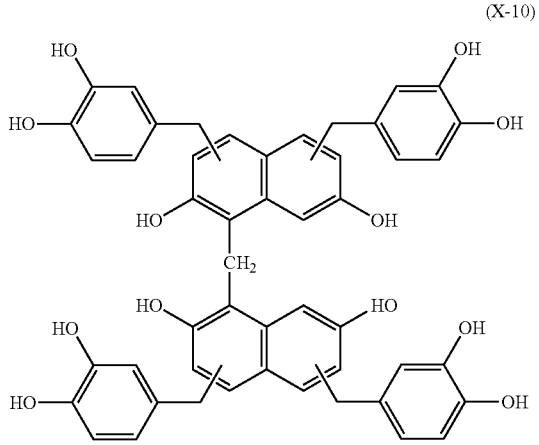
(X-10)

After 83.1 g of the naphthol compound (P-X1), 140.1 g of 3,4-dihydroxy benzyl alcohol (P-X2), and 1,000 g of 2-methoxy-1-propanol were made to a uniform solution at the liquid temperature of 80° C. under a nitrogen atmosphere, 30 g of 2-methoxy-1-propanol solution containing 20% of p-toluenesulfonic acid was gradually added to it; and then, the resulting mixture was stirred at the liquid temperature of 110° C. for 12 hours. After the reaction solution was cooled to room temperature, 2,000 g of methyl isobutyl ketone (MIBK) was added to it, and then, the organic phase was washed with 800 g of pure water for 5 times. The organic phase was evaporated to dryness under reduced pressure; and then, after 800 mL of tetrahydrofuran (THF) was added to the dried residue, 4,000 mL of hexane was added to the resulting solution to cause precipitation. The crystals precipitated were collected by filtration and then dried under reduced pressure to obtain the compound (X-10). From the GPC measurement, the weight average molecular weight (Mw) of 1,132 and the dispersibility (Mw/Mn) of 1.38 were obtained. From $^1$H-NMR, the introduction rate of 3,4-dihydroxy benzyl alcohol was calculated to be 4.0 molecules relative to one molecule of (P-X1).

Synthesis Example 11

Synthesis of Compound (X-11)

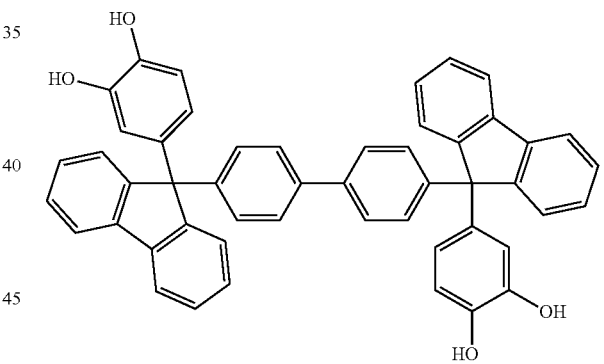
(X-11)

After 50.0 g of the biphenyl derivative (P-X3), 32.1 g of catechol (P-X4), and 500 mL of 1,2-dichloroethane were made to a uniform solution at the liquid temperature of 50° C. under a nitrogen atmosphere, 15 mL of methanesulfonic acid was gradually added to it; and then, the reaction was carried out at the liquid temperature of 50° C. for 4 hours. After the reaction solution was diluted by 1,000 mL of MIBK, insoluble matters were removed by filtration. The filtrate was transferred to a separatory funnel, and then washed by phase separation using 300 mL of ultrapure water for 7 times. After the organic phase was concentrated under reduced pressure, recrystallization was carried out by using methanol to obtain a biphenyl derivative. From $^1$H-NMR, it was confirmed that this biphenyl derivative is the compound (X-11). The purity of this compound obtained from the GPC measurement was 98.0%.

Comparative Synthesis Example 1

Synthesis of Compound (R-1)

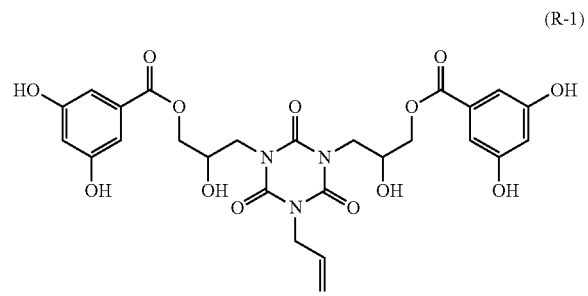 [SMILES: C=CCn1c(=O)n(CC(O)COC(=O)c2cc(O)cc(O)c2)c(=O)n(CC(O)COC(=O)c2cc(O)cc(O)c2)c1=O]

After 57.7 g of the epoxy compound (E-X2), 52.3 g of the carboxylic acid compound (C-X3), and 300 g of 2-methoxy-1-propanol were made to a uniform solution at the liquid temperature of 100° C. under a nitrogen atmosphere, 10.0 g of benzyl triethyl ammonium chloride was added to this solution; and then, the resulting mixture was stirred at the liquid temperature of 120° C. for 12 hours. After the reaction solution was cooled to room temperature, 1,000 g of methyl isobutyl ketone was added to it, and then, the organic phase was washed with 200 g of pure water for 5 times. The organic phase was evaporated to dryness under reduced pressure to obtain the compound (R-1). From the GPC measurement, the weight average molecular weight (Mw) of 601 and the dispersibility (Mw/Mn) of 1.02 were obtained.

Synthesis Example 12

Synthesis of Polymer (A2-1)

PGMEA (23.3 g) was stirred with heating at 80° C. under a nitrogen atmosphere. To this were added simultaneously and separately a mixture of 25.8 g of glycidyl methacrylate, 12.0 g of (2-phenoxyethyl)acrylic acid, 12.9 g of tricyclodecanyl acrylate, and 46.7 g of PGMEA, and a mixture of 4.45 g of dimethyl 2,2-azobis(2-methylpropionate) and 46.7 g of PGMEA during a period of 2 hours. After the resulting mixture was further stirred with heating for 16 hours, it was cooled to 60° C. After 200 g of heptane was added to it, the resulting mixture was cooled to room temperature, and then, it was allowed to stand for 2 hours. After the upper phase was removed by separation, 100 g of PGMEA was added; and then, heptane was removed by distillation under vacuum to obtain the PGMEA solution of the intended polymer (A2-1),

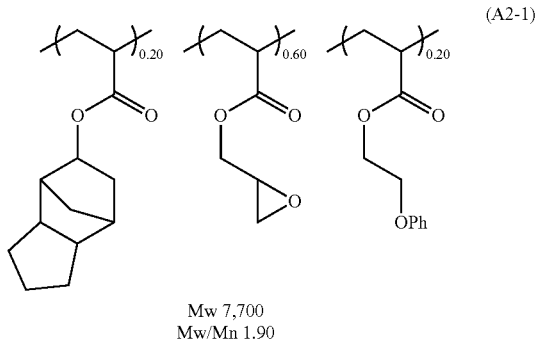

Mw 7,700
Mw/Mn 1.90

Synthesis Example 13

Synthesis of Polymer (A2-2)

PGMEA (23.3 g) was stirred with heating at 80° C. under a nitrogen atmosphere. To this were added simultaneously and separately a mixture of 28.5 g of N-(butoxymethyl)acrylamide, 12.0 g of (2-phenoxyethyl)acrylic acid, 12.9 g of tricyclodecanyl acrylate, and 46.7 g of PGMEA, and a mixture of 4.45 g of dimethyl 2,2-azobis(2-methylpropionate) and 46.7 g of PGMEA during a period of 2 hours. After the resulting mixture was further stirred with heating for 16 hours, it was cooled to 60° C. After 200 g of heptane was added to it, the resulting solution was cooled to room temperature, and then, it was allowed to stand for 2 hours. After the upper phase was removed by separation, 100 g of PGMEA was added; and then, heptane was removed by distillation under vacuum to obtain the PGMEA solution of the intended polymer (A2-2),

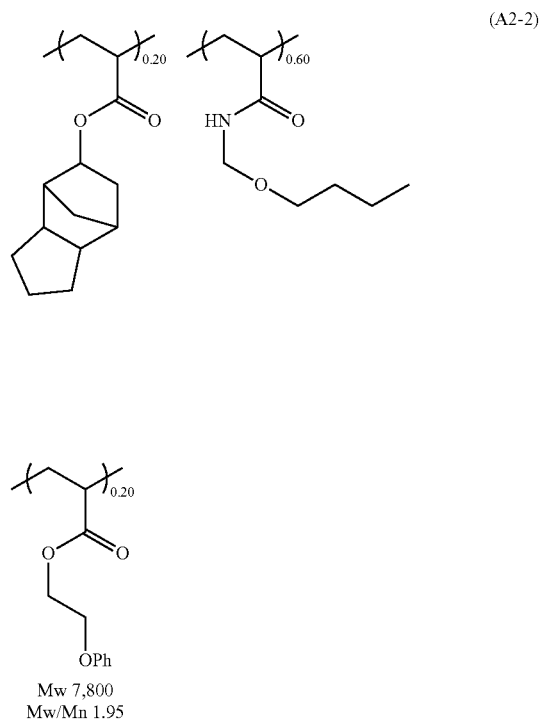

Mw 7,800
Mw/Mn 1.95

Preparation of Resist Underlayer Film Compositions (UL-1 to UL-13 and Comparative UL-1 to UL-3)

The compound (X-1) to (X-11), (R-1), the polymer (A2-1) to (A2-2), the acid generator (C1), and the crosslinking agent (E1) were dissolved into a solvent containing 0.05% by mass of the surfactant PF-6320 (manufactured by OMNOVA Solutions, Inc.; this surfactant was purified by the applicant of the present invention) with the ratio of these substances shown in Table 4; and the resulting mixture was filtrated through a 0.1-μm filter made of a fluorinated resin to obtain the resist underlayer film composition (UL-1 to UL-13 and Comparative UL-1 to UL-3). Meanwhile, in Table 4, PGMEA designates propylene glycol monomethyl ether acetate.

TABLE 4

| Resist underlayer film composition | Compound (parts by mass) | Polymer (parts by mass) | Acid generator (parts by mass) | Crosslinking agent (parts by mass) | Solvent (parts by mass) |
|---|---|---|---|---|---|
| UL-1 | X-1 (20) | A2-1 (80) | C1 (1) | — | PGMEA (1500) |
| UL-2 | X-2 (20) | A2-1 (80) | C1 (1) | — | PGMEA (1500) |
| UL-3 | X-3 (20) | A2-1 (80) | C1 (1) | — | PGMEA (1500) |
| UL-4 | X-4 (20) | A2-1 (80) | C1 (1) | — | PGMEA (1500) |
| UL-5 | X-5 (20) | A2-1 (80) | C1 (1) | — | PGMEA (1500) |
| UL-6 | X-6 (20) | A2-1 (80) | C1 (1) | — | PGMEA (1500) |
| UL-7 | X-7 (20) | A2-1 (80) | C1 (1) | — | PGMEA (1500) |
| UL-8 | X-8 (20) | A2-1 (80) | C1 (1) | — | PGMEA (1500) |
| UL-9 | X-9 (20) | A2-1 (80) | C1 (1) | — | PGMEA (1500) |
| UL-10 | X-10 (20) | A2-1 (80) | C1 (1) | — | PGMEA (1500) |
| UL-11 | X-11 (20) | A2-1 (80) | C1 (1) | — | PGMEA (1500) |
| UL-12 | X-2 (100) | — | C1 (1) | E1 (25) | PGMEA (1500) |
| UL-13 | X-2 (20) | A2-2 (80) | C1 (1) | — | PGMEA (1500) |
| Comp. UL-1 | R-1 (20) | A2-2 (80) | C1 (1) | — | PGMEA (1500) |
| Comp. UL-2 | R-1 (100) | — | C1 (1) | E1 (25) | PGMEA (1500) |
| Comp. UL-3 | — | A2-1 (100) | C1 (1) | — | PGMEA (1500) |

In Table 4, details of the acid generator (C1) and the crosslinking agent (E1) are as follows,

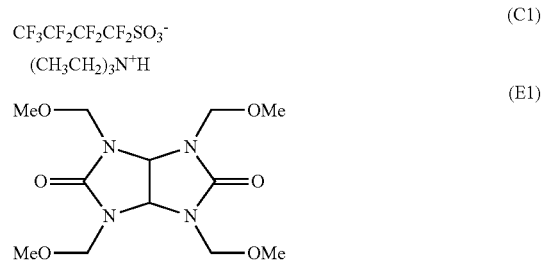

Measurements of Solvent Resistance and Optical Constants (Examples 1-1 to 1-13 and Comparative Examples 1-1 to 1-3)

Each of the resist underlayer film compositions prepared above (UL-1 to UL-13 and Comparative UL-1 to UL-3) was applied onto the silicon substrate; and after it was burnt for 60 seconds at the temperature shown in Table 5, the film thickness thereof was measured. Thereafter, PGMEA solvent was dispensed on it; and then, this was allowed to stand for 30 seconds, followed by spin drying and evaporation of the PGMEA solvent by baking at 100° C. for 60 seconds. Then, the film thickness was measured again; and the solvent resistance was evaluated from the difference in the film thickness before and after the PGMEA treatment. Further, the optical constants (refractive index "n" and extinction coefficient "k") of the resist underlayer film obtained after film formation, measured at 193 nm by a spectroscopic ellipsometer with variable angle of incidence (VASE; manufactured by J.A. Woollam Co., Inc.), are also shown in Table 5 below.

TABLE 5

| | Resist underlayer film composition | Film thickness after formation: a (Å) | Film thickness after solvent treatment: b (Å) | b/a × 100 (%) | Burning Temp. | n/k |
|---|---|---|---|---|---|---|
| Example 1-1 | UL-1 | 2022 | 2022 | 100 | 240° C. | 1.64/0.20 |
| Example 1-2 | UL-2 | 2039 | 2035 | 100 | 240° C. | 1.69/0.25 |
| Example 1-3 | UL-3 | 2042 | 2041 | 100 | 240° C. | 1.69/0.25 |
| Example 1-4 | UL-4 | 2005 | 1999 | 100 | 240° C. | 1.68/0.26 |
| Example 1-5 | UL-5 | 2018 | 2018 | 100 | 240° C. | 1.64/0.20 |
| Example 1-6 | UL-6 | 2030 | 2027 | 100 | 240° C. | 1.69/0.25 |
| Example 1-7 | UL-7 | 2035 | 2034 | 100 | 240° C. | 1.69/0.25 |
| Example 1-8 | UL-8 | 2001 | 1996 | 100 | 240° C. | 1.68/0.26 |
| Example 1-9 | UL-9 | 2033 | 2030 | 100 | 240° C. | 1.69/0.25 |
| Example 1-10 | UL-10 | 2010 | 2009 | 100 | 240° C. | 1.64/0.20 |
| Example 1-11 | UL-11 | 2012 | 2012 | 100 | 240° C. | 1.63/0.24 |
| Example 1-12 | UL-12 | 2002 | 1982 | 99 | 240° C. | 1.72/0.41 |
| Example 1-13 | UL-13 | 2034 | 2030 | 100 | 240° C. | 1.69/0.25 |
| Comp. Example 1-1 | Comp. UL-1 | 2030 | 2027 | 100 | 240° C. | 1.70/0.25 |
| Comp. Example 1-2 | Comp. UL-2 | 1997 | 1977 | 99 | 240° C. | 1.73/0.41 |
| Comp. Example 1-3 | Comp. UL-3 | 1998 | 1995 | 100 | 240° C. | 1.70/0.30 |

In the patterning process of the present invention, it was found that all the resist underlayer film compositions are excellent in the film-formability, hardly show a decrease in the film thickness by treatment with the solvent, and give the films having an excellent solvent resistance. With regard to the optical constants, when the n-value is approximately in the range of 1.5 to 1.9 and the k-value is approximately in the range of 0.1 to 0.5, the reflected light from the substrate can be significantly suppressed, so that the film like this can be used as the underlayer film for the photoresist patterning, though depending on the film thickness, the upper layer film, and the like. In all of the above Examples the optical constants are within the suitable ranges; and thus, it was found that they can be used for the photoresist patterning as the resist underlayer film.

Dry Etching Test in $N_2/H_2$-based gas system
(Examples 2-1 to 2-13 and Comparative Examples 2-1 to 2-4)

With regard to the resist underlayer film formed in the way as mentioned above and the resist upper layer film formed in the way as described below, the dry etching test by the $N_2/H_2$-based gas system was carried out.

The resist upper layer film composition used for patterning (photoresist for ArF) was prepared as follows: the polymer (resin) shown by the ArF monolayer resist polymer 1, the acid generator PAG 1, and the basic compound amine 1 were dissolved into the solvent containing 0.1% by mass of FC-4430 (manufactured by Sumitomo 3M Limited) with the ratio shown in Table 6; and then, the resulting solution was filtrated through a 0.1-μm filter made of a fluorinated resin.

TABLE 6

| Resist upper layer film composition | Polymer (parts by mass) | Acid generator (parts by mass) | Basic compound (parts by mass) | Solvent (parts by mass) |
|---|---|---|---|---|
| PR-1 | ArF monolayer resist polymer 1 (100) | PAG 1 (6.6) | amine 1 (0.8) | PGMEA (2,500) |

The ArF monolayer resist polymer 1, the PAG 1, and the amine 1, which were used herein, are shown below,

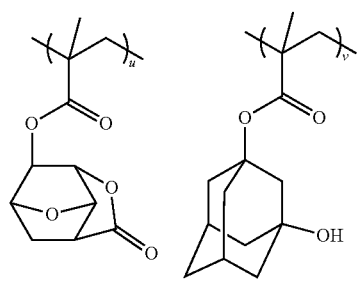

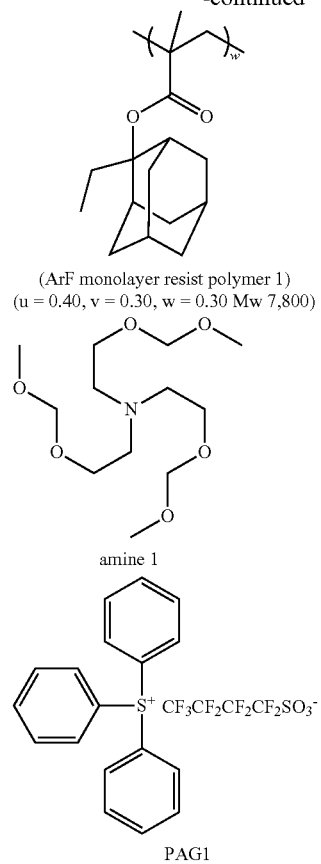

(ArF monolayer resist polymer 1)
(u = 0.40, v = 0.30, w = 0.30 Mw 7,800)

amine 1

PAG1

The resist upper layer film composition obtained above (PR-1) was applied onto the silicon substrate and baked at 105° C. for 60 seconds to obtain the photoresist film having the thickness of about 100 nm.

The dry etching test by the $N_2/H_2$-based gas system was carried out under the following condition.

Etching Condition:

| Chamber pressure | 2.7 Pa |
|---|---|
| RF power | 1,000 W |
| $N_2$ gas flow rate | 500 mL/minute |
| $H_2$ gas flow rate | 30 mL/minute |
| Period | 20 seconds |

The difference in the film thickness between before and after the dry etching was measured with the etching equipment (Telius; manufactured by Tokyo Electron, Ltd.), and then, this difference was divided with the etching period to obtain the dry etching rate. The results thereof are summarized in Table 7.

TABLE 7

| | Composition | Etching rate (Å/s) |
|---|---|---|
| Example 2-1 | UL-1 | 28 |
| Example 2-2 | UL-2 | 31 |
| Example 2-3 | UL-3 | 31 |
| Example 2-4 | UL-4 | 31 |
| Example 2-5 | UL-5 | 28 |
| Example 2-6 | UL-6 | 31 |

TABLE 7-continued

| | Composition | Etching rate (Å/s) |
|---|---|---|
| Example 2-7 | UL-7 | 31 |
| Example 2-8 | UL-8 | 31 |
| Example 2-9 | UL-9 | 31 |
| Example 2-10 | UL-10 | 27 |
| Example 2-11 | UL-11 | 25 |
| Example 2-12 | UL-12 | 62 |
| Example 2-13 | UL-13 | 31 |
| Comp. Example 2-1 | Comp. UL-1 | 31 |
| Comp. Example 2-2 | Comp. UL-2 | 62 |
| Comp. Example 2-3 | Comp. UL-3 | 29 |
| Comp. Example 2-4 | PR-1 | 24 |

From the above results, in the resist underlayer film compositions of the present invention (UL-1 to UL-13), it was found that all the resist underlayer films are faster in the dry etching rate as compared with the resist upper layer films (Comparative Examples 2-4). Therefore, the resist underlayer film composition of the present invention is suitable especially in the manufacturing process including removal of the resist underlayer film by the dry etching after processing of the substrate because the residue after the removal of the resist underlayer film can be reduced.

Evaluation of the Gap-Filling Characteristic
(Examples 3-1 to 3-13 and Comparative Examples 3-1 to 3-3)

Figure 2:
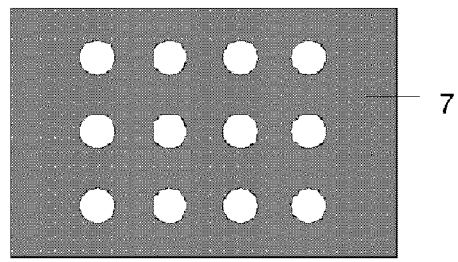
FIG. 2 is an explanatory drawing of the evaluation method of the gap-filling characteristic in Examples and Comparative Examples.
Figure 2:
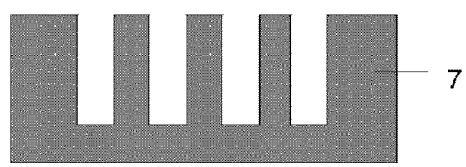
Figure 2:
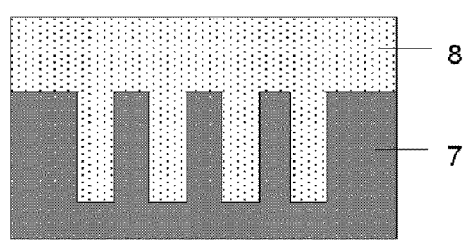

Each of the resist underlayer film compositions mentioned above was applied onto the SiO$_2$ wafer substrate having a dense hole pattern (hole diameter: 0.16 µm, hole depth: 0.50 µm, and distance between the centers of neighboring two holes: 0.32 µm), and then, it was burnet at the temperature described in Table 8 for the period of 60 seconds to form the resist underlayer film. The substrate used is the underlayment substrate 7 (SiO$_2$ wafer substrate) having the dense hole pattern as depicted in FIG. 2(G) (bird's eye view) and FIG. 2(H) (cross section view). The shape of the cross section of each wafer substrate was observed with a scanning electron microscope (SEM) so as to confirm whether or not inside the hole is filled with the resist underlayer film without any void. The results thereof are summarized in Table 8. When the resist underlayer film composition that is poor in the gap-filling characteristic is used, the voids are formed inside the holes in this evaluation. When the resist underlayer film composition that is excellent in the gap-filling characteristic is used, the resist underlayer film 8 is filled inside the holes without forming the voids as illustrated in FIG. 2(I) in this evaluation.

TABLE 8

| | Resist underlayer film composition | Burning temp. | Void |
|---|---|---|---|
| Example 3-1 | UL-1 | 240° C. | Not formed |
| Example 3-2 | UL-2 | 240° C. | Not formed |
| Example 3-3 | UL-3 | 240° C. | Not formed |
| Example 3-4 | UL-4 | 240° C. | Not formed |
| Example 3-5 | UL-5 | 240° C. | Not formed |
| Example 3-6 | UL-6 | 240° C. | Not formed |
| Example 3-7 | UL-7 | 240° C. | Not formed |
| Example 3-8 | UL-8 | 240° C. | Not formed |
| Example 3-9 | UL-9 | 240° C. | Not formed |
| Example 3-10 | UL-10 | 240° C. | Not formed |
| Example 3-11 | UL-11 | 240° C. | Not formed |
| Example 3-12 | UL-12 | 240° C. | Not formed |
| Example 3-13 | UL-13 | 240° C. | Not formed |

TABLE 8-continued

| | Resist underlayer film composition | Burning temp. | Void |
|---|---|---|---|
| Comp. Example 3-1 | Comp. UL-1 | 240° C. | Not formed |
| Comp. Example 3-2 | Comp. UL-2 | 240° C. | Not formed |
| Comp. Example 3-3 | Comp. UL-3 | 240° C. | Not formed |

From the above results, it was found that the resist underlayer film compositions of Examples (UL-1 to UL-13) can fill the hole pattern without forming the voids thereby having excellent gap-filling characteristic.

Evaluation of the Planarization Characteristic
(Examples 4-1 to 4-13 and Comparative Examples 4-1 to 4-3)

Figure 3:
FIG. 3 is an explanatory drawing of the evaluation method of the planarization characteristic in Examples and Comparative Examples.
Figure 3:
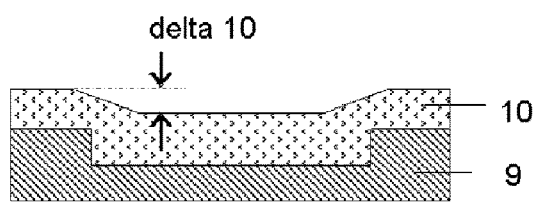

Each of the resist underlayer film compositions was applied onto the underlayment substrate 9 (SiO$_2$ wafer substrate) having a giant isolated trench pattern (FIG. 3(J), trench width: 10 µm, and trench depth: 0.1 µm) and then, it was burnt under the condition described in Table 9. Then, the difference in the film thickness between the trench portion and the non-trench portion of the resist underlayer film 10 (delta 10 in FIG. 3(K)) was observed with a scanning electron microscope (SEM). The results are summarized in Table 9. In this evaluation, it can be said that as the difference in the film thickness is smaller, the planarization characteristic is better.

TABLE 9

| | Resist underlayer film composition | Burning condition | Difference in film thickness (nm) |
|---|---|---|---|
| Example 4-1 | UL-1 | 240° C. × 60 sec. | 45 |
| Example 4-2 | UL-2 | 240° C. × 60 sec. | 50 |
| Example 4-3 | UL-3 | 240° C. × 60 sec. | 50 |
| Example 4-4 | UL-4 | 240° C. × 60 sec. | 50 |
| Example 4-5 | UL-5 | 240° C. × 60 sec. | 45 |
| Example 4-6 | UL-6 | 240° C. × 60 sec. | 50 |
| Example 4-7 | UL-7 | 240° C. × 60 sec. | 50 |
| Example 4-8 | UL-8 | 240° C. × 60 sec. | 50 |
| Example 4-9 | UL-9 | 240° C. × 60 sec. | 50 |
| Example 4-10 | UL-10 | 240° C. × 60 sec. | 45 |
| Example 4-11 | UL-11 | 240° C. × 60 sec. | 50 |
| Example 4-12 | UL-12 | 240° C. × 60 sec. | 50 |
| Example 4-13 | UL-13 | 240° C. × 60 sec. | 50 |
| Comp. Example 4-1 | Comp. UL-1 | 240° C. × 60 sec. | 55 |
| Comp. Example 4-2 | Comp. UL-2 | 240° C. × 60 sec. | 55 |
| Comp. Example 4-3 | Comp. UL-3 | 240° C. × 60 sec. | 60 |

From the above results, it was found that the resist underlayer film compositions of Examples (UL-1 to UL-13) have smaller difference between the trench portion and the non-trench portion in the thickness of the resist underlayer film as compared with the resist underlayer film composition of the Comparative Example (Comparative UL-3), and thus, they are excellent in the planarization characteristic.

Evaluation of Resistance to the Basic Hydrogen Peroxide Aqueous Solution (Examples 5-1 to 5-13 and Comparative Examples 5-1 to 5-3)

The resist underlayer film composition was applied onto the silicon wafer cut to the size of 3-cm square, and then, it was burnt with the condition described in Table 10 so as to form the film with the thickness of about 100 nm. This wafer piece was soaked in the 1.0% by mass hydrogen peroxide aqueous solution containing 0.5% by mass of ammonia at 70° C. for 5 minutes. And then, after this was rinsed with deionized water, whether or not the resist underlayer film was delaminated from the wafer was visually checked. When, part or all of the resist underlayer film is delaminated thereby resulting in exposure of the silicon wafer surface, it is judged that the resist underlayer film tested has insufficient resistance to the basic hydrogen peroxide aqueous solution. These results are summarized in Table 10.

TABLE 10

|  | Resist underlayer film composition | Burning condition | Test result (70° C. × 5 min.) |
|---|---|---|---|
| Example 5-1 | UL-1 | 240° C. × 60 sec. | No delamination |
| Example 5-2 | UL-2 | 240° C. × 60 sec. | No delamination |
| Example 5-3 | UL-3 | 240° C. × 60 sec. | No delamination |
| Example 5-4 | UL-4 | 240° C. × 60 sec. | No delamination |
| Example 5-5 | UL-5 | 240° C. × 60 sec. | No delamination |
| Example 5-6 | UL-6 | 240° C. × 60 sec. | No delamination |
| Example 5-7 | UL-7 | 240° C. × 60 sec. | No delamination |
| Example 5-8 | UL-8 | 240° C. × 60 sec. | No delamination |
| Example 5-9 | UL-9 | 240° C. × 60 sec. | No delamination |
| Example 5-10 | UL-10 | 240° C. × 60 sec. | No delamination |
| Example 5-11 | UL-11 | 240° C. × 60 sec. | No delamination |
| Example 5-12 | UL-12 | 240° C. × 60 sec. | No delamination |
| Example 5-13 | UL-13 | 240° C. × 60 sec. | No delamination |
| Comp. Example 5-1 | Comp. UL-1 | 240° C. × 60 sec. | Total delamination |
| Comp. Example 5-2 | Comp. UL-2 | 240° C. × 60 sec. | Total delamination |
| Comp. Example 5-3 | Comp. UL-3 | 240° C. × 60 sec. | Total delamination |

From the above results, it was found that the resist underlayer film compositions of Examples (UL-1 to UL-13) are superior to the resist underlayer film compositions of Comparative Examples (Comparative UL-1 to UL-3) in the resistance to the basic hydrogen peroxide aqueous solution.

mentioned before (PR-1) was applied onto the resist underlayer film thus formed, and then, it was baked at 105° C. for 60 seconds to form the photoresist film having the film thickness of about 200 nm.

Next, the photoresist film thus formed was exposed to a light by using the ArF immersion exposure instrument (NSR-S610C; manufactured by Nikon Corp, NA: 1.30, σ: 0.98/0.65, 35° dipole s-polarized illumination, and 6% half tone phase shift mask). Then, after the photoresist film thus exposed was baked at 100° C. for 60 seconds (PEB), it was developed for 30 seconds by using an aqueous 2.38% by mass of tetramethyl ammonium hydroxide (TMAH) solution to obtain the 160 nm 1:1 positive lines-and-spaces (L/S) photoresist pattern.

Next, the resist underlayer film was etched by dry etching using the etching equipment (Telius; manufactured by Tokyo Electron, Ltd.) by using the photoresist pattern as a mask to form the resist underlayer film pattern. The etching condition is described below.

Transcription condition of the photoresist pattern to the resist underlayer film:

| Chamber pressure | 2.7 Pa |
|---|---|
| RF power | 1,000 W |
| $N_2$ gas flow rate | 500 mL/minute |
| $H_2$ gas flow rate | 30 mL/minute |
| Period | 40 seconds |

Formation of the resist underlayer film pattern was confirmed by the top-down SEM view of the wafer after etching of the underlayer film. Next, the wafer was cut to the width of 2 cm; and this wafer piece was soaked in the aqueous 1.0% by mass hydrogen peroxide aqueous solution containing 0.5% by mass of ammonia for 5 minutes at 70° C., rinsed with deionized water and dried, and then observed by using an optical microscope so as to evaluate whether or not the delamination of the resist underlayer film pattern took place. The evaluation results are summarized in Table 11.

TABLE 11

|  | Resist Underlayer Film composition | Burning condition | Resist Underlayer film pattern | Delamination |
|---|---|---|---|---|
| Example 6-1 | UL-1 | 240° C. × 60 sec. | Formable | No delamination |
| Example 6-2 | UL-2 | 240° C. × 60 sec. | Formable | No delamination |
| Example 6-3 | UL-3 | 240° C. × 60 sec. | Formable | No delamination |
| Example 6-4 | UL-4 | 240° C. × 60 sec. | Formable | No delamination |
| Example 6-5 | UL-5 | 240° C. × 60 sec. | Formable | No delamination |
| Example 6-6 | UL-6 | 240° C. × 60 sec. | Formable | No delamination |
| Example 6-7 | UL-7 | 240° C. × 60 sec. | Formable | No delamination |
| Example 6-8 | UL-8 | 240° C. × 60 sec. | Formable | No delamination |
| Example 6-9 | UL-9 | 240° C. × 60 sec. | Formable | No delamination |
| Example 6-10 | UL-10 | 240° C. × 60 sec. | Formable | No delamination |
| Example 6-11 | UL-11 | 240° C. × 60 sec. | Formable | No delamination |
| Example 6-12 | UL-12 | 240° C. × 60 sec. | Formable | No delamination |
| Example 6-13 | UL-13 | 240° C. × 60 sec. | Formable | No delamination |
| Comp. Example 6-1 | Comp. UL-1 | 240° C. × 60 sec. | Formable | Delaminated |
| Comp. Example 6-2 | Comp. UL-2 | 240° C. × 60 sec. | Formable | Delaminated |
| Comp. Example 6-3 | Comp. UL-3 | 240° C. × 60 sec. | Formable | Delaminated |

Evaluation of Patterning (Examples 6-1 to 6-13 and Comparative Examples 6-1 to 6-3)

Each of the resist underlayer film compositions was applied onto the Si wafer substrate, and then, it was burnt with the condition described in Table 11 to form the resist underlayer film. The resist upper layer film composition From the above results, it was found that in all the resist underlayer film compositions of the present invention (Examples 6-1 to 6-13), the upper layer resist pattern is satisfactorily transcribed to the resist underlayer film so that the resist underlayer film composition of the present invention can be suitably used in the fine lithography by the multilayer resist method. In addition, it could be confirmed that the formed resist underlayer film pattern is excellent in the resistance to the basic hydrogen peroxide aqueous solution. Therefore, the resist underlayer film composition and patterning process of the present invention are useful especially because they enable to manufacture a semiconductor device by fine processing in which the multilayer resist method and the chemical etching method using a chemical such as the basic hydrogen peroxide aqueous solution are combined.

From the above, the resist underlayer film composition, the patterning process, and the method for forming the resist underlayer film of the present invention can be suitably used in the multilayer resist process for the fine patterning in the semiconductor device manufacturing, and especially these can also be used in the multilayer resist process including the wet etching process, so that these are extremely useful in industry.

It must be noted here that the present invention is not limited to the embodiments as described above. The foregoing embodiments are mere examples; any form having substantially the same composition as the technical idea described in claims of the present invention and showing similar effects is included in the technical scope of the present invention.

EXPLANATIONS OF LETTERS OR NUMERALS

1: Substrate, 2: layer to be processed,
2a: pattern formed on the substrate,
3: resist underlayer film, 3a: resist underlayer film pattern,
4: resist intermediate film,
4a: resist intermediate film pattern,
5: resist upper layer film, 5a: resist pattern,
6: prescribed portion,
7: underlayment substrate having dense hole pattern,
8: resist underlayer film,
9: underlayment substrate having giant isolated trench pattern,
10: resist underlayer film,
delta 10: difference in film thickness of the resist underlayer film between the trench portion and the non-trench portion.

What is claimed is:

1. A resist underlayer film composition, wherein the resist underlayer film composition is used for a multilayer resist method, the composition comprising:
   (A1) one, or two or more, of a compound represented by following general formula (X); and
   (B) an organic solvent,

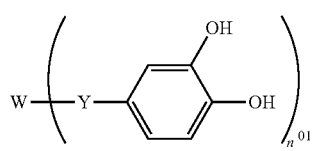

(X)

wherein "$n^{01}$" represents an integer of 1 to 10; when "$n^{01}$" is 2, W represents a sulfinyl group, a sulfonyl group, an ether group, or a divalent organic group having 2 to 50 carbon atoms;

when "$n^{01}$" is an integer other than 2, W represents an $n^{01}$-valent organic group having 2 to 50 carbon atoms; and Y represents a methylene group, —OCH$_2$CH(OH) CH$_2$OC(=O) —, —CH$_2$CH(OH)CH$_2$OC(=O) —, —OCH$_2$CH(OH)CH$_2$OC(=O)CH$_2$— or —CH$_2$CH(OH)CH$_2$OC(=O)CH$_2$—.

2. The resist underlayer film composition according to claim 1,
   wherein W in the general formula (X) represents a divalent to pentavalent heterocyclic ring group having 3 to 10 carbon atoms.

3. The resist underlayer film composition according to claim 1,
   wherein the resist underlayer film composition further comprises:
   (A2) a polymer (1A) comprising one, or two or more, of a repeating unit represented by following general formula (1),

(1)

wherein $R^{01}$ represents a hydrogen atom or a methyl group; and $R^{02}$ represents a group selected from following formulae (1-1) to (1-3),

(1-1)

(1-2)

(1-3)

wherein dotted lines represent a bonding hand.

4. The resist underlayer film composition according to claim 3, wherein the polymer (1A) further comprises one, or two or more, of a repeating unit represented by following general formula (2),

(2)

wherein $R^{01}$ represents the same as before; $A^1$ represents a single bond, —CO$_2$—, or a divalent connecting group having 2 to 10 carbon atoms and including —CO$_2$—;

and Ar$^1$ represents a substituted or unsubstituted aryl group having 6 to 20 carbon atoms.

5. The resist underlayer film composition according to claim 3,
wherein the polymer (1A) further comprises one, or two or more, of a repeating unit represented by following general formula (3),

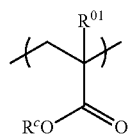

(3)

wherein R$^{01}$ represents the same as before; and R$^c$ represents a monovalent group having 3 to 20 carbon atoms and having an alicyclic structure.

6. The resist underlayer film composition according to claim 3,
wherein a weight average molecular weight of the polymer (1A) is in a range of 1,000 to 20,000.

7. The resist underlayer film composition according to claim 1,
wherein the resist underlayer film composition further comprises one or more additives out of (C) an acid generator, (D) a surfactant, (E) a crosslinking agent, (F) a plasticizer, and (G) a pigment.

8. The resist underlayer film composition according to claim 1,
wherein the resist underlayer film composition is the resist underlayer film composition which gives a resist underlayer film having a resistance to an ammonia-containing hydrogen peroxide aqueous solution.

9. The resist underlayer film composition according to claim 8,
wherein the resist underlayer film is the resist underlayer film which does not show any peel-off of its own when a silicon substrate formed with the resist underlayer film is soaked into a 1.0% by mass hydrogen peroxide aqueous solution containing 0.5% by mass of ammonia at 70° C. for 5 minutes.

10. A patterning process, wherein the patterning process is to form a pattern on a substrate to be processed and comprises:
(I-1) forming a resist underlayer film on the substrate to be processed by using the resist underlayer film composition according to claim 1,
(I-2) forming a resist upper layer film on the resist underlayer film by using a photoresist composition,
(I-3) forming a pattern on the resist upper layer film by developing the resist upper layer film by using a developer after the resist upper layer film is pattern-exposed, and
(I-4) transcribing the pattern to the resist underlayer film by dry etching using as a mask the resist upper layer film formed with the pattern.

11. A patterning process, wherein the patterning process is to form a pattern on a substrate to be processed and comprises:
(II-1) forming a resist underlayer film on the substrate to be processed by using the resist underlayer film composition according to claim 1,
(II-2) forming a resist intermediate film on the resist underlayer film,
(II-3) forming a resist upper layer film on the resist intermediate film by using a photoresist composition,
(II-4) forming a pattern on the resist upper layer film by developing the resist upper layer film by using a developer after the resist upper layer film is pattern-exposed,
(II-5) transcribing the pattern to the resist intermediate film by dry etching using as a mask the resist upper layer film formed with the pattern, and
(II-6) transcribing the pattern to the resist underlayer film by dry etching using as a mask the resist intermediate film transcribed with the pattern.

12. A patterning process, wherein the patterning process is to form a pattern on a substrate to be processed and comprises:
(III-1) forming a resist underlayer film on the substrate to be processed by using the resist underlayer film composition according to claim 1,
(III-2) forming an inorganic hard mask intermediate film selected from a silicon oxide film, a silicon nitride film, and a silicon oxide nitride film on the resist underlayer film,
(III-3) forming an organic antireflective film on the inorganic hard mask intermediate film,
(III-4) forming a resist upper layer film on the organic antireflective film by using a photoresist composition,
(III-5) forming a pattern on the resist upper layer film by developing the resist upper layer film by using a developer after the resist upper layer film is pattern-exposed,
(III-6) transcribing the pattern to the organic antireflective film and the inorganic hard mask intermediate film by dry etching using as a mask the resist upper layer film formed with the pattern, and
(III-7) transcribing the pattern to the resist underlayer film by dry etching using as a mask the inorganic hard mask intermediate film transcribed with the pattern.

13. The patterning process according to claim 11, wherein after the (II-6) step, the patterning process further has a step in which the resist intermediate film transcribed with the pattern is removed by wet etching using a basic hydrogen peroxide aqueous solution.

14. The patterning process according to claim 10, wherein after the (I-4) step, the (II-6) step, or the (III-7) step, the patterning process further has a step in which the pattern is transcribed to the substrate to be processed by wet etching using a basic hydrogen peroxide aqueous solution and the resist underlayer film transcribed with the pattern as a mask.

15. The patterning process according to claim 10, wherein after the (I-4) step, the (II-6) step, or the (III-7) step, the patterning process further has a step in which the substrate to be processed is pattern-processed by an ion implantation using as a mask the resist underlayer film transcribed with the pattern.

16. The patterning process according to claim 15, wherein after the step of the patterning process of the substrate to be processed by the ion implantation, the patterning process further has a step in which the resist intermediate film transcribed with the pattern is removed by wet etching using a basic hydrogen peroxide aqueous solution.

17. The patterning process according to claim 10, wherein the resist underlayer film composition having a dry etching rate faster than a dry etching rate of the resist upper layer film is used.

18. The patterning process according to claim 10, wherein the resist underlayer film is formed by applying the resist underlayer film composition onto the substrate to be processed followed by heat-treatment thereof in a temperature range of 100° C. or more and 500° C. or less, and for a period of in a range of 10 to 600 seconds.

19. The patterning process according to claim 10, wherein as the substrate to be processed, a substrate having a structural body with a height of 30 nm or more, or having a step is used.

20. A method for forming a resist underlayer film, wherein the resist underlayer film composition according to claim 1 is applied onto a substrate to be processed, and then, the resist underlayer film composition is subjected to heat-treatment in a temperature range of 100° C. or more and 500° C. or less, and for a period of in a range of 10 to 600 seconds to form a cured film.

21. The method for forming a resist underlayer film according to claim 20, wherein as the substrate to be processed, a substrate having a structural body with a height of 30 nm or more, or having a step is used.

* * * * *